United States Patent [19]
Seyferth et al.

[11] Patent Number: 5,969,073
[45] Date of Patent: Oct. 19, 1999

[54] GROUP 4 METAL-CONTAINING ORGANOSILICON DENDRIMERS AND METHOD FOR SYNTHESIZING ORGANOSILICON DENRIMERS

[75] Inventors: Dietmar Seyferth, Lexington, Mass.; Ralf Wyrwa, Oelknitz, Germany

[73] Assignee: Massachusetts Institute of Technology, Cambridge, Mass.

[21] Appl. No.: 08/814,273

[22] Filed: Apr. 10, 1997

Related U.S. Application Data

[63] Continuation-in-part of application No. 08/611,495, Mar. 5, 1996, abandoned, which is a continuation-in-part of application No. 08/621,290, Mar. 22, 1996, abandoned.

[51] Int. Cl.$^6$ ................................................. C08G 79/00
[52] U.S. Cl. ................................. 528/9; 528/15; 525/475
[58] Field of Search .......................... 528/15, 9; 525/475

[56] References Cited

U.S. PATENT DOCUMENTS

| | | | |
|---|---|---|---|
| 5,177,162 | 1/1993 | Matsuura et al. | 526/70 |
| 5,276,110 | 1/1994 | Zhou et al. | 525/479 |
| 5,486,632 | 1/1996 | Devore et al. | 556/11 |
| 5,491,246 | 2/1996 | Rosen et al. | 556/7 |
| 5,512,693 | 4/1996 | Rosen et al. | 556/7 |
| 5,539,068 | 7/1996 | Devore et al. | 526/126 |
| 5,677,410 | 10/1997 | Mager et al. | 528/15 |
| 5,679,755 | 10/1997 | Mager et al. | 528/35 |

FOREIGN PATENT DOCUMENTS

| | | | |
|---|---|---|---|
| A 0 230 707 | 8/1987 | European Pat. Off. | C08F 10/00 |
| A 0 293 815 | 12/1988 | European Pat. Off. | C08F 4/60 |
| A 0 350 170 | 1/1990 | European Pat. Off. | C08F 10/00 |
| A 0 372 414 | 6/1990 | European Pat. Off. | C07F 17/00 |
| A 0 593 875 | 4/1994 | European Pat. Off. | C08F 8/00 |

OTHER PUBLICATIONS

Lon J. Mathias et al., "Hyperbranched Poly(siloxysilanes)," *J. Am. Chem. Soc.*, vol. 113, pp. 4043–4044, 1991.

Slawomir Rubinsztain, "Synthesis and Characterization of New Poly(siloxysilanes)," *J. Inorg. Organomet. Polymers*, vol. 4, pp. 61–73, 1994.

Dietmar Seyferth et al., "Synthesis of an Organosilicon Dendrimer Containing 324 Si–H Bonds," *Organometallics*, vol. 13, pp. 2682–2690, 1994.

Roovers et al., "Regular Star Polymers with 64 and 128 Arms, Models for Polymeric Micelles," *Macromolecules*, vol. 26, pp. 4324–4331, 1993.

Roovers et al., "Synthesis of Carbosilane Dendrimers and Its Application on the Preparation of 32 Arms and 64 Arms Star Polymers," *Polymer Preprints*, Preprints, vol. 33, pp. 182–183, 1992.

Zhou et al., "Synthesis of Novel Carbosilane Dendritic Macromolecules," *Macromolecules*, vol. 26, pp. 963–968, 1993.

Zhou et al., "Synthesis and Properties of Regular Star Polybutadienes with 32 Arms," *Rubber Chemistry and Technology*, vol. 65, pp. 303–314, 1992.

Thaver, "Metallocene Catalysts Initiate New Era in Polymer Synthesis," *Chem. & Eng. News*, pp. 15–20, Sep. 11, 1995.

Tomalia et al., "Starburst Dendrimers: Molecular–Level Control of Size, Shape, Surface Chemistry, Topology, and Flexibility from Atoms to " *Angew. Chem., Int. Ed. Engl.*, vol. 29, pp. 138–175, 1990.

Seyferth, "Polycarbosilanes: An Overview," *Inorg, Organomet, Polymers*, eds. M. Zeldin et al., American Chemical Society, Washington, DC., 1988, pp. 21–42.

Curry, "The Synthesis and Polymerization of Organosilanes Containing Vinyl and Hydrogen Joined to the same Silicon Atom," *J. Am. Chem. Soc.*, vol. 78, pp. 1686–1689, 1956.

van der Made et al., "Silane Dendrimers," *J. Chem. Soc., Chem. Commun.*, pp. 1400–1401, 1992.

Uchida et al., "General Strategy for the Systematic Synthesis of Oligosiloxanes, Silicone Dendrimers," *J. Am. Chem. Soc.*, vol. 112, pp. 7077–7079, 1990.

Morikawa et al., "Synthesis and Characterization of New Polysiloxane Starburst Polymers," *Macromolecules*, vol. 24, pp. 3469–3474, 1991.

Alonso, et al., "Organometallic Silicon Dendrimers," *J. Chem. Soc., Chem. Commun.* pp. 2575–2576, 1994.

Knapen et al., "Homogeneous catalysts based on silane dendrimers functionalized with arylnickel(II) complexes," *Nature*, vol. 372, pp. 659–663, 1994.

Roovers et al., "Synthesis of Carbosilane Dendrimers and its Application on the Preparation of 32 Arms and 64 Arms Star" *Abstracts of Papers of the American Chemical Society*, vol. 203, P200–POLY, 1992.

Muzafarov et al., "Organosilicon Dendrimers: Volume–Growing Polyallylcarbosilanes," *Polymer Science*, vol. 35, pp. 1575–1580, 1993.

Hackh's Chemical Dictionary, 1972 ed. p. 611.

*Primary Examiner*—Melvyn I. Marquis
*Attorney, Agent, or Firm*—Wolf, Greenfield & Sacks, P.C.

[57] ABSTRACT

Group 4 metal-containing organosilicon dendrimers are described. Also described are methods for synthesizing the dendrimers. The dendrimers can be useful in several applications including as olefin polymerization and copolymerization catalysts and as silane polymerization catalysts.

76 Claims, 4 Drawing Sheets

GROUP 4 METAL-CONTAINING ORGANOSILICON DENDRIMERS AND METHOD FOR SYNTHESIZING ORGANOSILICON DENRIMERS

This application is a continuation-in-part of commonly-owned, co-pending U.S. patent application Ser. No. 08/611,495, filed Mar. 5, 1996 and a continuation-in-part of U.S. patent application Ser. No. 08/621/290, filed Mar. 22, 1996 both abandoned.

The United States Government has rights in this invention pursuant to Contract No. CHE 9221212 awarded by the National Science Foundation.

BACKGROUND OF THE INVENTION

1. Field of the Invention

The invention relates to Group 4 metal-containing organosilicon dendrimers, methods of preparation thereof, and methods of use thereof.

2. Description of the Prior Art

Dendrimers are chemical compounds characterized by a regular, highly branched structure as shown schematically in FIG. 1. Dendrimer 10 of FIG. 1 is a second generation dendrimer, denoted by a generation number, $G_n$, equal to $G_2$. Dendrimer 10 includes an initiator core 12 from which branches, whose number is denoted by $N_n$ and characterized by length l, emanate. Four main branches ($N_1=4$) emanate directly from initiator core 12 and form four primary branch points 14 from each of which three new branches ($N_1=3$) emanate and form secondary branch points 16 as the next generation polymer is produced. Branches that emanate from branch points 16 terminate in end groups 20.

Dendrimers are ideally monodisperse, i.e., they consist of single, identical species, all of which have the same composition and molecular weight. Dendrimers can be characterized by a range of molecular weights, ranging from relatively low oligomeric molecular weight, to relatively high polymeric molecular weights. Dendrimer molecular weights can depend on several factors including length of the arms, the extent of arm branching, the functionality of the branching groups in the arms, the length of connecting groups between branching sites and the functionality of the dendrimer core. Typically, dendrimers are soluble in organic solvents and their solubility in a particular solvent can be optimized by the choice of appropriate functional groups for the end groups. However, end groups may be chosen so as to result in water solubility. Dendrimers of intermediate generation number, $G_n$, typically with n in the range of from about 1 to about 10, depending upon the dendrimer system, are characterized by an uncongested periphery with empty space between neighboring end groups. As such, intermediate generation number dendrimers have high surface areas and a relatively large proportion of unoccupied dendrimer interior volume.

Dendrimers can be synthesized using a "divergent procedure", according to which dendrimers are grown outward by repetitive chemical steps using a multifunctional central core molecule as the starting material. According to this approach, successive hydrosilylation and vinylation, or alternatively, allylation, steps are performed on the polyfunctional core, which can be a tetravinylsilane or tetrallylsilane to form the dendrimeric structure. The divergent procedure is reliable and effective, provided that appropriate reaction conditions are maintained until that point in the synthesis when steric congestion at the dendrimer periphery hinders further dendrimer growth. However, the divergent procedure is multistep, relatively expensive and, hence, may not ideally suited for large scale commercial applications.

Alternatively, a "convergent procedure" can be used to synthesize dendrimers by preparing segments of the dendrimer first and then attaching the segments to a central core molecule. However, the convergent procedure is also multistep, relatively expensive and, hence, may not be ideally suited for large scale commercial applications.

A third approach for dendrimer synthesis is a "cascade procedure". According to this approach, a single monomer is used in a single type of reaction to prepare the dendrimer. Generally, a cascade procedure begins with a monomer containing two different reactive functions, x and y, more specifically, one x function and two or more y functions. The x and y functions are selected so that x can react with y, but not with itself. The reaction between x and y is initiated so that branching growth occurs to produce a dendrimer. The structure of the dendrimers produced according to a cascade procedure will not be as regular a structure as that of dendrimers synthesized according to a divergent or convergent procedure. Dendrimers produced using the cascade procedure will be polydisperse rather than monodisperse and have been referred to as "hyperbranched" materials. Typically, the cascade procedure is relatively inexpensive and well-suited to large scale commercial applications.

A type of organosilicon dendrimers, carbosilane dendrimers, and their preparation are described in Seyferth et al., Organometallics, 13 (1994) 2682–2690. A typical dendrimer prepared in the foregoing study is shown in FIG. 2.

Thus, it would be highly desirable to exploit the foregoing dendrimer characteristics, including relatively high surface area and relatively high porosity, for applications including catalysis by preparation of dendrimers having end or interior group substituents with a desired chemical activity. Moreover, it would be highly desirable to exploit the foregoing desirable cascade procedure characteristics for the synthesis of organosilicon dendrimers.

SUMMARY OF THE INVENTION

Many of the foregoing needs are met by an organosilicon dendrimer with one or more dendrimer arms containing a Group 4 metal such as Ti, Zr, or Hf or mixtures thereof. The invention provides dendrimers with Group 4 metal-containing end or interior group substituents, methods for making the dendrimers and polymerization methods that use the Group 4 metal-containing dendrimers as catalysts.

According to one aspect of the invention, a method for synthesizing such a dendrimer including a Group 4 metal substituent is provided. The method includes steps of (a) providing a core molecule containing one or more reactive functional groups; (b) providing a silicon hydride with an appropriate reactive functionality such as a silicon-halogen bond; (c) providing a hydrosilylation catalyst; (d) reacting the silicon hydride with the core molecule in the presence of the hydrosilylation catalyst to produce an intermediate organosilicon dendrimer; (e) reacting the intermediate organosilicon dendrimer to introduce an unsaturated organic functional group; (f) repeating steps (b), (c), (d), and (e) n times using the intermediate organosilicon dendrimer as formed in step (e) as the core molecule to produce a $G_n$ generation organosilicon dendrimer wherein n is an integer in the range of from about 1 to about 10 and $G_n$ is the generation number; and (g) reacting the $G_n$ generation organosilicon dendrimer with a Group 4 metal-containing reagent to form an organosilicon dendrimer including a Group 4 metal.

Another aspect of the invention provides a method for polymerizing an olefin including steps of contacting olefin monomers with an organosilicon dendrimer catalyst including a Group 4 metal, such as Ti, Zr, or Hf, or mixtures thereof, so that the olefin monomers are polymerized to form a polyolefin.

Yet another aspect of the invention is a dehydrogenative condensation polymerization of silane monomers, $RSiH_3$, to form a polysilane using the dendrimers of the invention as a catalyst.

In yet another aspect of the invention, such a cascade procedure includes steps of providing starting monomers including a Si—H bond and at least two functional groups that each include a terminal $=CH_2$ bond, inducing a hydrosilylation reaction to consume the monomers, thereby producing an intermediate organosilicon dendrimer and reacting the intermediate organosilicon dendrimer with a Group 4 metal-containing reagent to form a Group 4 metal-containing organosilicon dendrimer.

In still another aspect of the invention, a core-based cascade procedure for synthesizing a Group 4 transition metal-containing organosilicon dendrimer is provided. According to the method, a core molecule such as, but not limited to, $Si[(CH_2)_nCH=CH_2]_4$ with n=0–20; $RSi[(CH_2)_nCH=CH_2]_3$ where n=0–20 and R is an alkyl, aryl, halogen, alkoxy or aryloxy group or the like; $Si[C_6H_4(CH_2)_nCH=CH_2]_4$ where n=0–20 and $C_6H_4$ is para-phenylene or meta-phenylene or the like; and $Rsi[C_6H_4(CH_2)_nCH=CH_2]_3$ where n=0–20 and R is alkyl, aryl, halogen, alkoxy or aryloxy or the like; and $C_6H_4$ is para-phenylene or meta-phenylene or the like is the starting material. A first reagent such as, but not limited to, $HSi(CH=CH_2)_3$; $HSi(CH_2CH=CH_2)_3$; $HSi[(CH_2)_nCH=CH_2]_3$, where n=2–20; $R(H)Si(CH=CH_2)_2$; $R(H)Si(CH_2CH=CH_2)_2$; or $R(H)Si[(CH_2)_nCH=CH_2]_2$, where n=2–20, R is methyl or higer alkyl, phenyl or substituted phenyl, halogen, alkoxy, aryloxy or dialkylamino groups or the like is added to the core molecule to form an intermediate product. Additional reagent such as, but not limited to, $HSi(CH=CH_2)_3$; $HSi(CH_2CH=CH_2)_3$; $HSi[(CH_2)_nCH=CH_2]_3$, where n=2–20; $R(H)Si(CH=CH_2)_2$; or $R(H)Si(CH_2CH=CH_2)_3$; $R(H)Si[(CH_2)_nCH=CH_2]_2$, where n=2–20, R is methyl or higher alkyl, phenyl or substituted phenyl, halogen, alkoxy, aryloxy or dialkylamino groups or the like, is added to the intermediate product to form an intermediate organosilicon dendrimer. Finally, the intermediate organosilicon dendrimer is reacted with a Group 4 metal-containing reagent to form an organosilicon dendrimer including a Group 4 metal.

In a further aspect of the invention a core-based synthesis of a Group 4 metal-containing dendrimer having a desired functionality at an internal location within, rather than at the periphery of the dendrimer, is provided. The method includes steps of providing a core molecule such as $Si[(CH_2)_n CH=CH_2]_4$ where n=0–20; $RSi[(CH_2)_nCH=CH_2]_3$ where n=0–20 and R is an alkyl, aryl, halogen, alkoxy or aryloxy group. The core molecule is then reacted with a first reagent such as $[CH_2=CH(CH_2)_n]_2C_6H_5SiH$, where n=0–20 to form an intermediate product. The intermediate product is reacted with a second reagent such as $[CH_2=CH(CH_2)_n]_3$ SiH; or $[CH_2=CH(CH_2)_n]_2SiRH$, where R is alkyl and n=0–20 to form an intermediate dendrimer by the cascade procedure including reactive dendrimer arm ends. A third reagent such as $R_2SiHX$ where R is an alkyl group is then added to react with the reactive dendrimer arm ends of the intermediate dendrimer to form peripheral Si—X dendrimer arm ends wherein X is F, Cl, Br, or I. The peripheral Si—X dendrimer arm ends are reduced to form Si—H peripheral dendrimer arm ends. The Si—X dendrimer arm ends can be reduced using $LiAlH_4$ or other suitable reducing agent. The Si—H peripheral dendrimer arm ends are reacted with a reagent including a terminal olefin group to form a second intermediate dendrimer. The second intermediate dendrimer is reacted with HX, where X is $O_3SCF_3$ or Br, to form a dendrimer having a Si—X internal functionality, by cleavage of the Si—$C_6H_5$ bond. The dendrimer having a Si—X internal functionality is reduced with a reducing agent to form a dendrimer having a Si—H internal functionality. Finally, the dendrimer having a Si—H internal functionality is reacted with a Group 4 metal-containing reagent to form an organosilicon dendrimer including an internal Group 4 metal functionality.

In a further aspect of the invention, the foregoing synthesis method is modified by instead of reducing the peripheral Si—X dendrimer arm ends to form Si—H dendrimer arm ends and then reacting the Si—H dendrimer arm ends with a reagent including a terminal olefin group, the Si—X bonds are alkylated with RMgX or RLi where R is an alkyl group and X is Cl, Br or I.

In still a further aspect of the invention, the already-described core-based synthesis method for an internally functionalized dendrimer is modified by growing the core molecule out to a larger core size by reacting the core molecule with $[CH_2=CH(CH_2)_n]R_2SiH$ where R is a methyl or alkyl group and n=0–20 or $[CH_2=CH(CH_2)_n]_2$ SiH to form an intermediate product followed by reacting the intermediate product with $[CH_2=CH(CH_2)_n]_2C_6H_5SiH$ to form a second intermediate product which is further treated as has already been described.

According to another aspect of the invention a method is provided for synthesizing a carbosilane dendrimer using a cascade procedure. The method includes steps of providing starting monomers including a Si—H bond and at least two functional groups that each include a terminal $=CH_2$ bond, inducing a hydrosilylation reaction to consume the monomers, thereby producing an intermediate organosilicon dendrimer including a reactive $CH=CH_2$ group. A reagent characterized by the general formula $R_2SiHX$ where R is Me, Et, higher alkyl, or aryl or the like and X is F, Cl, Br, I and alkoxy or the like is added to the intermediate dendrimer, reducing the Si—X bond to produce a reactive Si—H bond. The reactive Si—H bond is then reacted with an organic compound including an unsaturated carbon-carbon bond such as an olefinic or acetylenic bond to form a carbosilane dendrimer.

In yet another aspect of the invention, a core-based cascade procedure for synthesizing a Group 4 transition metal-containing organosilicon dendrimer is provided. According to the method, a core molecule such as, but not limited to, $Si[(CH_2)_nCH=CH_2]_4$ with n=0–20; $RSi[(CH_2)_nCH=CH_2]_3$ where n=0–20 and R is an alkyl, aryl, halogen, alkoxy or aryloxy group or the like; $Si[C_6H_4(CH_2)_nCH=CH_2]_4$ where n=0–20 and $C_6H_4$ is para-phenylene or meta-phenylene or the like; or $RSi[C_6H_4(CH_2)_nCH=CH_2]_3$ where n=0–20 and R is alkyl, aryl, halogen, alkoxy or aryloxy or the like; and $C_6H_4$ is para-phenylene or meta-phenylene or the like is the starting material. A first reagent such as, but not limited to, $HSi(CH=CH_2)_3$; $HSi(CH_2CH=CH_2)_3$; $HSi[(CH_2)_nCH=CH_2]_3$, where n=2–20; $R(H)Si(CH=CH_2)_2$; $R(H)Si(CH_2CH=CH_2)_2$or $R(H)Si[(CH_2)_nCH=CH_2]_2$, where n=2–20, R is methyl or higher alkyl, phenyl or substituted phenyl, halogen, alkoxy, aryloxy or dialkylamino groups or the like is added to the core molecule to form an intermediate product. Additional reagent such as $HSi(CH=CH_2)_3$; $HSi(CH_2CH=CH_2)_3$;

HSi[(CH$_2$)$_n$CH=CH$_2$]$_3$, where n=2–20; R(H)Si(CH= CH$_2$)$_2$; R(H)Si(CH$_2$CH=CH$_2$)$_2$; R(H)Si[(CH$_2$)$_n$CH=CH$_2$]$_2$, where n=2–20, R is methyl or higher alkyl, phenyl or substituted phenyl, halogen, alkoxy, aryloxy or dialkylamino groups or the like and (CH$_2$=CHCH$_2$)$_2$(CH$_3$)SiH is added to the intermediate product to form an intermediate organosilicon dendrimer including a terminal CH=CH$_2$. A reagent characterized by the general formula R$_2$SiHX where R is Me, Et, higher alkyl, or aryl or the like and X is F, Cl, Br, I and alkoxy or the like and including a Si—X bond is added to the intermediate dendrimer, reducing the Si—X bond to produce a reactive Si—H bond. The reactive Si—H bond is then reacted with an organic compound including an unsaturated carbon-carbon bond such as an olefinic or acetylenic bond to form a carbosilane dendrimer.

DESCRIPTION OF PREFERRED EMBODIMENTS

Figure 1:
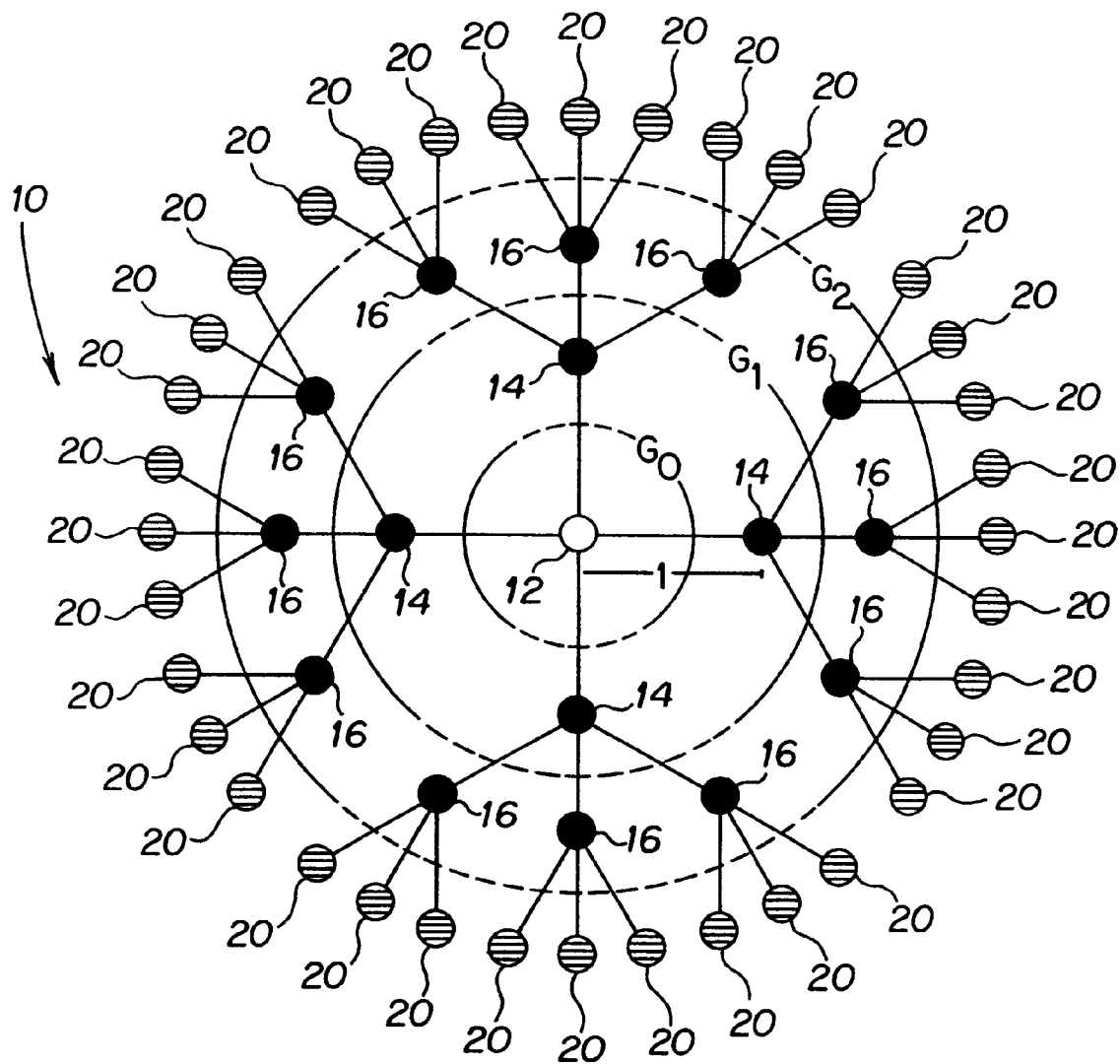
FIG. 1 is a schematic, generalized illustration of a typical dendrimer.
Figure 2:
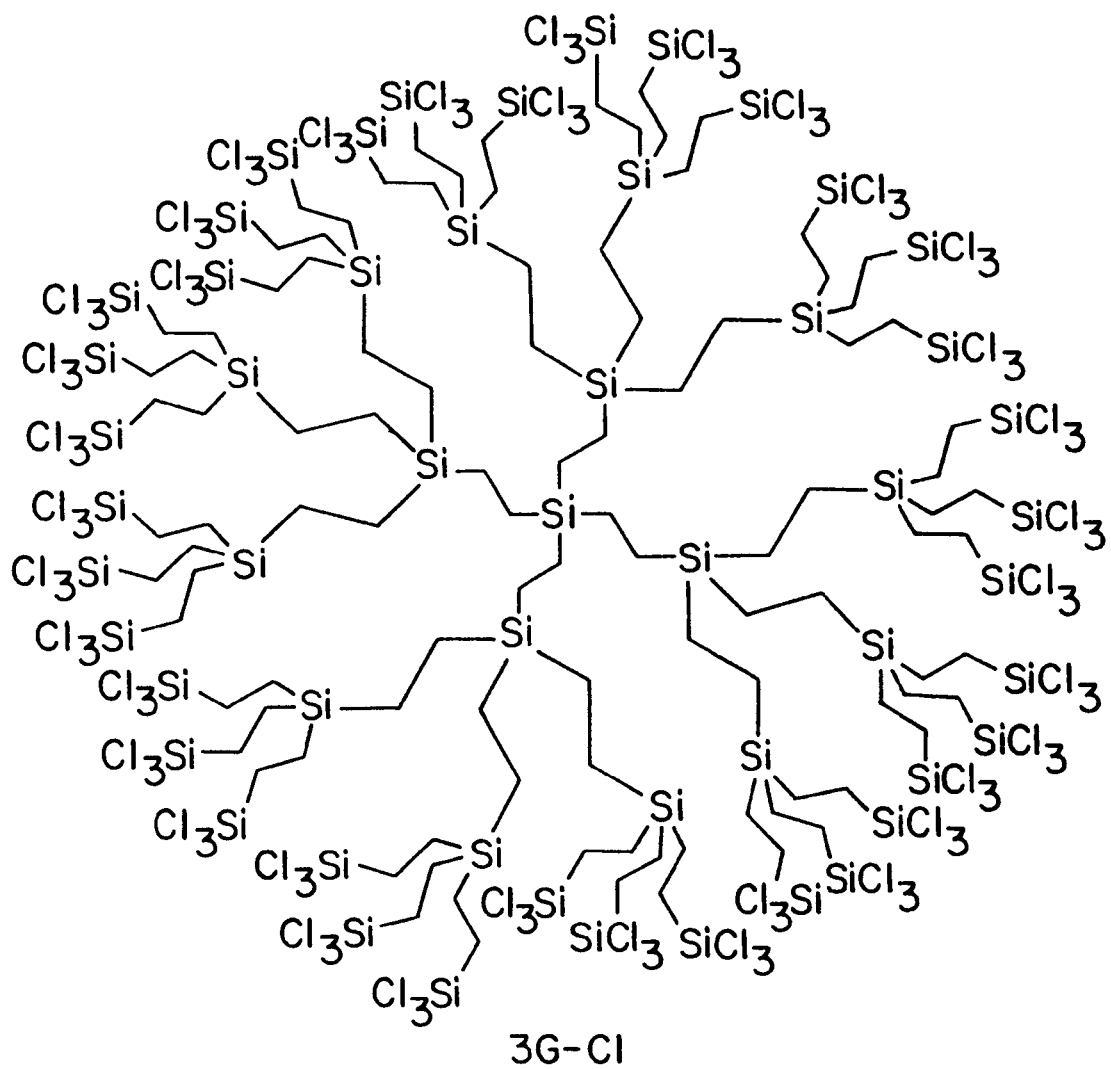
FIG. 2 is a schematic, generalized illustration of a typical dendrimer prepared according to the study described in Seyferth et al., Organometallics, 13 (1994) 2682–2690.

The Group 4 metal-containing organosilicon dendrimers can be carbosilanes or siloxanes or hybrids thereof. As used herein in the specification and claims, a "carbosilanell is an organosilicon compound with organic bridges between the silicon atoms. The bridges can be alkylene, such as —CH$_2$—, —CH$_2$CH$_2$—, —(CH$_2$)$_n$—, or substituted variants thereof; alkenylene, such as —CH=CH—, —CH=CH—CH=CH—, or substituted variants thereof; mixed alkylene/alkenylene, such as —CH$_2$CH=CHCH$_2$—; arylene, such as

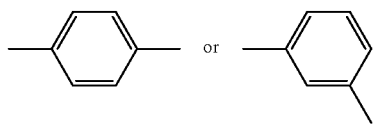

and substituted variants thereof; or heterocyclic groups such as

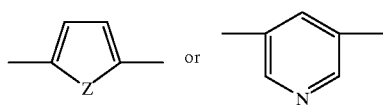

where Z is O, S, NH or NR and R is alkyl or aryl or the like. Carbosilanes are further defined and described in Seyferth, "Polycarbosilanes: An Overview", in *Inorganic and Organometallic Polymers,* (ACS Symposium Series 360), M. Zeldin et al., eds., American Chemical Society, Washington, D.C., 1988, pp. 21–42.

Organosilicon dendrimers that can be used in the present invention include, but are not limited to, the organosilicon dendrimers that will be described below. The following references are incorporated by reference. An organosilicon dendrimer or dendrimers grown from a tetraallylsilane core via successive hydrosilylation and allylation steps as described in A. W. van der Made et al., J. Chem. Soc., Chem. Commun. (1992) 1400–1401 can be used. Alternatively, an organosilicon dendrimer or dendrimers grown from a 1,3, 5-(CH$_2$=CHMe$_2$Si)$_3$C$_6$H$_3$ core via successive hydrosilylation/vinylation or allylation steps can be used. A hybrid carbosilane/siloxane dendrimer or dendrimers grown by catalyzed oligomerization of CH$_2$=CHSI(OSiMe$_2$H)$_3$ as described in L. J. Mathias et al., J. Am. Chem. Soc., 113 (1991) 4043–4044 or of HSi(OSiMe$_2$CH=CH$_2$)$_3$ as described in S. Rubinsztain, J. Inorg. Organomet. Polym., 4 (1994) 61–72 can be used. Finally, a siloxane dendrimer or dendrimers such as those described in H. Uchida et al., J. Am. Chem. Soc., 112 (1990) 7077–7079 and in A. Morikawa, et al., Macromolecules, 24 (1991) 3469–3474 can be used.

A Group 4 metal-containing organosilicon dendrimer of the present invention can be further characterized by a dendrimer arm end, i.e., that portion of the dendrimer arm farthest away from the core of the dendrimer, and the metal-containing unit can be located at the dendrimer arm end and, thus, at the periphery of the dendrimer.

Alternatively, the Group 4 metal-containing unit can be located at the dendrimer arm interior, i.e., at a position intermediate between the dendrimer core and the dendrimer periphery.

The Group 4 metal-containing unit can be a metallocene unit such as a bis(cyclopentadienyl) complex metallocene unit or substituent having the formula

wherein Z is a chalcogen, halide, alkyl, aryl, amide, alkenyl or alkynyl substituent, M is the Group 4 metal and

▶ denotes a bond connecting the metallocene unit to the dendrimer arm.

The chalcogen substituent can be an O$_2$CR, OR, O$_3$SCF$_3$, or SR group wherein R is an organic substituent such as alkyl, polyfluoroalkyl, alkenyl, or aryl. The halide substituent can be a F, Cl, Br or I ion or mixtures thereof The metallocene unit can also be of the formula

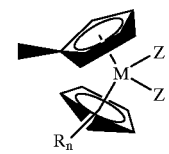

further including an R substituent wherein the number of such substituents, n, is an integer in the range of from about 1 to about 5 and R is an alkyl group such as a methyl group or an aryl group such as a phenyl or benzyl group. As used herein in the specification and claims, Me represents a methyl group and Ph represents a phenyl group.

Alternatively, the metallocene unit can be characterized by the formula

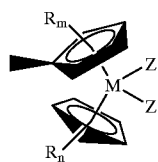

which further includes an R substituent where m, the number of such substituents, is an integer in the range of from about 1 to about 4 and R is an alkyl group such as a methyl group or an aryl group such as a phenyl or benzyl group.

The metallocene unit can also include a bridging group represented by

and have the formula

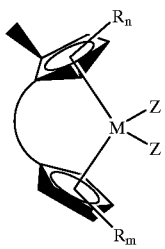

where R is an alkyl or aryl group, n=0–3 and m=0–4. The bridging group can be an organic bridge group such as $CH_2$, $CH_2CH_2$, $CH_2CH_2CH_2$, $CMe_2$, or $Me_2CCMe_2$, $CH{=}CH$, and the like. The bridging group can also be an organosilicon bridge such as $SiMe_2$, $SiMe_2CH_2SiMe_2$, $SiMe_2CH_2CH_2SiMe_2$, $Me_2SiSiMe_2$, or $Me_2SiOSiMe_2$ and the like.

The metallocene unit can also further include a functional group represented by

and have the formula

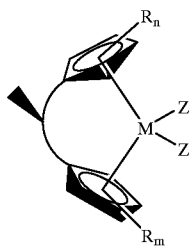

wherein

is a group bonded to the dendrimer such as $MeSiCH_2CH_2SiMe_2$, $MeSiCH_2SiMe_2$, MeSi, PhSi, $MeSiSiMe_2$, $MeSiOSiMe_2$ and the like, R is an alkyl or aryl group, m=0–4 and n=0–4.

The metallocene unit can also be characterized by the formula

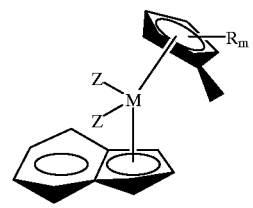

The organosilicon dendrimer of the present invention can include a monocyclopentadienyl unit metallocene unit having the formula

wherein Z is a group such as a chalcogen, halide, alkyl, aryl or amide substituent, M is the Group 4 metal, and

denotes a bond connecting the metallocene unit to the dendrimer arm and R is a group such as methyl, alkyl, or aryl and n is an integer from 0 to about 4.

The dendrimer of the present invention can include a metallocene unit characterized by the formula

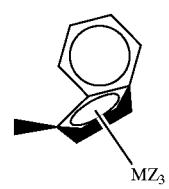

wherein Z is a chalcogen, halide, alkyl, aryl, or amide substituent, M is the Group 4 metal, and

denotes a bond connecting the metallocene unit to the dendrimer arm.

The metallocene unit also can be characterized by the formula

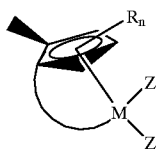

wherein Z is a chalcogen, halide, alkyl, aryl, or amide substituent, M is the Group 4 metal

◀ denotes a bond connecting the metallocene unit to the dendrimer arm, and

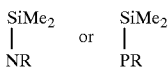

represents a

| SiMe$_2$ |     | SiMe$_2$ |
|----------|-----|----------|
| NR       | or  | PR       | group wherein R is a group such as methyl, isopropyl, t-butyl, alkyl, phenyl, or aryl and n=0–3.

The metallocene unit can have the formula

wherein Z is a chalcogen, halide, alkyl, aryl, or amide substituent, M is the Group 4 metal,

◀ denotes a bond connecting the metallocene unit to the dendrimer arm,

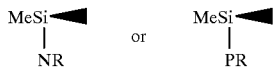

represents a

| MeSi◀ |     | MeSi◀ |
|-------|-----|-------|
| NR    | or  | PR    | group wherein R is a group such as methyl, isopropyl, t-butyl, alkyl, phenyl, or aryl.

Alternatively, the metallocene unit can be further characterized by the formula

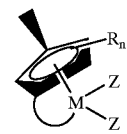

wherein Z can be a chalcogen, halide, alkyl, aryl, or amide substituent, M is a Group 4 metal,

◀ denotes a bond connecting the metallocene unit to the dendrimer arm,

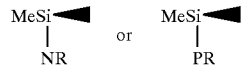

represents a group such as

| MeSi◀ |     | MeSi◀ |
|-------|-----|-------|
| NR    | or  | PR    | groups, R is a methyl, isopropyl, t-butyl, alkyl, or ary group, and n is an integer in the range of from about 0 to about 3.

The foregoing dendrimers can be chemically attached to a solid support phase such as a refractory oxide like alumina, silica or zirconia, or an insoluble polymer like cross-linked polystyrene. The solid support phase can be selected depending upon the dendrimer catalytic properties desired.

Several processes exist to prepare an organosilicon, such as a carbosilane, dendrimer intermediate of a desired generation number, $G_n$, to which the metal-containing, such as a metallocene, substituent can then be attached. In one embodiment, the carbosilane dendrimer growth chemistry is based upon a repetitive hydrosilylation/alkenylation sequence as described in Seyferth et al., Organometallics, 13 (1994) 2682–2690 where the dendrimer was grown out to the fourth generation. Alternatively, a cascade synthesis method may be used as described herein.

Hydrosilylation/Alkenylation Method

The following describes certain aspects of the present invention with respect to hydrosilylation/alkenylation methods of forming group 4 metal-containing organosilicon dendrimers.

Silicon hydrides appropriate for use in the hydrosilylation reaction include, but are not limited to, $HSiCl_3$, $CH_3SiHCl_2$ ($CH_3$), $SiHCl$, $ClCH_2(CH_3)SiHCl$, $PhSiHCl_2$, $HSi(OR)_3$, $CH_3SiH_2(OR)_2$, $(CH_3)_2SiH(OR)_2$ or $PhSiH OR)_2$, wherein R is a methyl or higher alkyl group. The hydrosilylations can be catalyzed by platinum-based catalysts such as $H_2PtCl_6 \cdot 6H_2O$, the Karstedt catalyst and other homogeneous Pt catalysts, as well as heterogeneous catalysts such as Pt on charcoal or asbestos. Other transition metal catalysts can be used, as can free radical initiators such as organic peroxides and azo compounds. The reagents used in the alkenylation step can include, but are not limited to, Grignard reagents such as $CH_2$=$CHMgBr$; or $CH_2$=$CH(CH_2)_n MgCl_3$, n=1–11; organolithium reagents such as $CH_2$=$CHLi$; or $CH_2$=$CH(CH_2)_n Li$, n=–11. Alkynyl-metal reagents such as $HC$≡$CNa$; $HC$≡$CMgBr$; or $HC$≡$C(CH_2)_n MgBr$, n=1–11 can also be used. Use of alkynyl-metal reagents for the hydrosilylation results in an alkenylene bridge rather than an alkylene bridge between the silicon atoms.

The carbosilane dendrimer prepared according to the foregoing method is then reacted with an appropriate Group 4 metallocene-containing reagent to form a carbosilane dendrimer having arms terminating in Group 4 metallocene substituents. The $G_n$ generation carbosilane dendrimer to be reacted with the Group 4 metallocene-containing reagent by a catalyzed hydrosilylation reaction can include a dendrimer arm end that terminates in a Si—H group. The Si—H containing group can be a —SiMe$_2$H, —SiMeClH, —SiMeH$_2$, —SiCl$_2$H, —SiPhClH, or SiPhH$_2$ group. The Group 4 metallocene substituent-containing reagent to be reacted with the foregoing $G_n$ generation carbosilane dendrimer can contain an unsaturated organic functional group wherein carbon is multiply bonded, such as C=C, C≡C, C=N, or C=O, that can be bonded to the metallocene reactant either directly or via other intervening atoms.

The metallocene-containing reagent can be chosen from among, but is not limited to, the reagents represented by the following formulas.

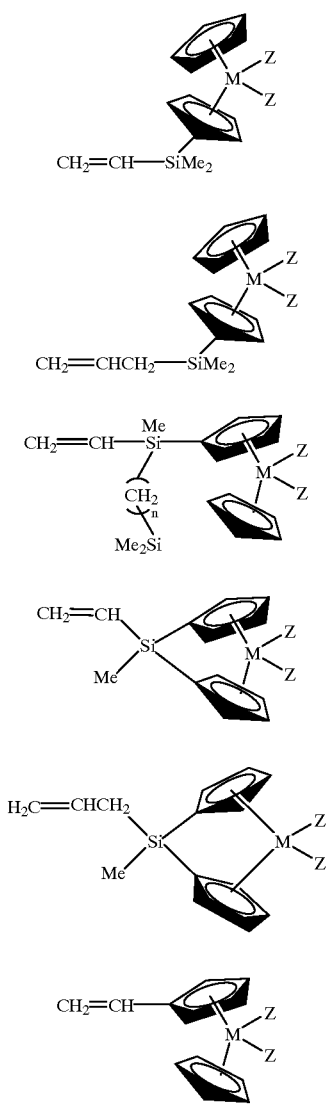

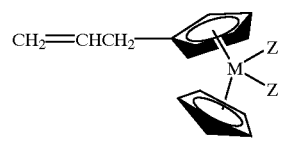

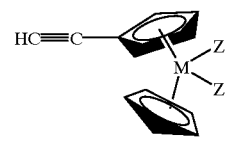

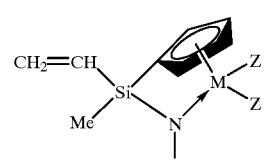

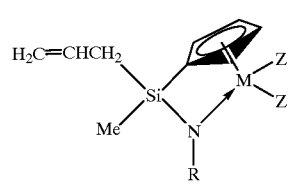

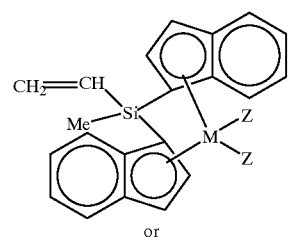

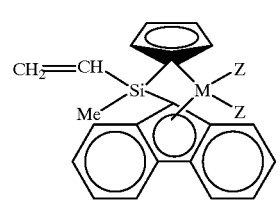

wherein Z can be a chalcogen, halide, alkyl, aryl, amide, alkenyl or alkynyl substituent, M is the Group 4 metal, R is a group such as methyl, alkyl, phenyl, or aryl, and → represents an electron pair donor bond. Z can be a halide such as F, Cl, Br or I, a chalcogen such as O, OR, S, SR, or an amide such as NR, where R as already described. Typically, the dihalide is used. Each formula is identified by a Roman numeral which will be used for reference elsewhere in the specification. In certain embodiments, the metallocene substituent-containing reagent can include a metallocene substituent such as those given by the following formulas

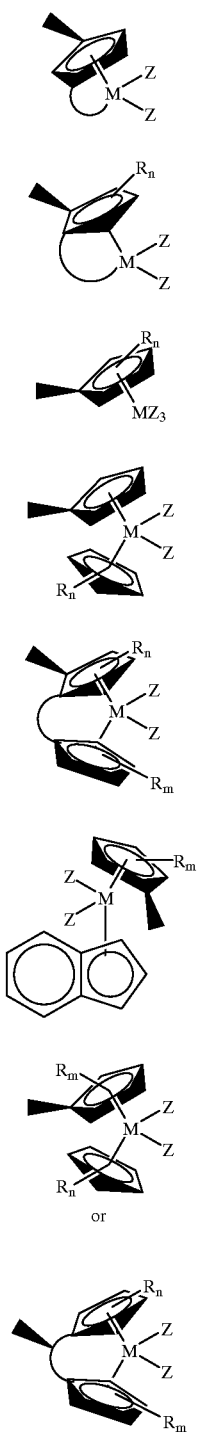

XI(c)

XI(d)

XI(e)

XI(f)

XI(g)

XI(h)

XI(i)

or

XI(j)

Alternatively, the $G_n$ generation organosilicon dendrimer arm end can terminate in a dendrimer unsaturated organic functional group and the Si—H containing functional group can be on the metal-containing reagent. The unsaturated organic functional group can be a group such as $CH_2$=CH, $CH_2$=CH($CH_2$)$_n$, $CH_2$=CHC$_6$H$_4$, HC≡C, or HC≡C($CH_2$)$_n$, where n=1–11. The metal-containing reagent Si—H group can then be reacted with the dendrimer unsaturated organic functional group by a catalyzed hydrosilylation reaction. Metallocene substituent-containing reagents can be given by formulas XII, XIII, XIV, and the like.

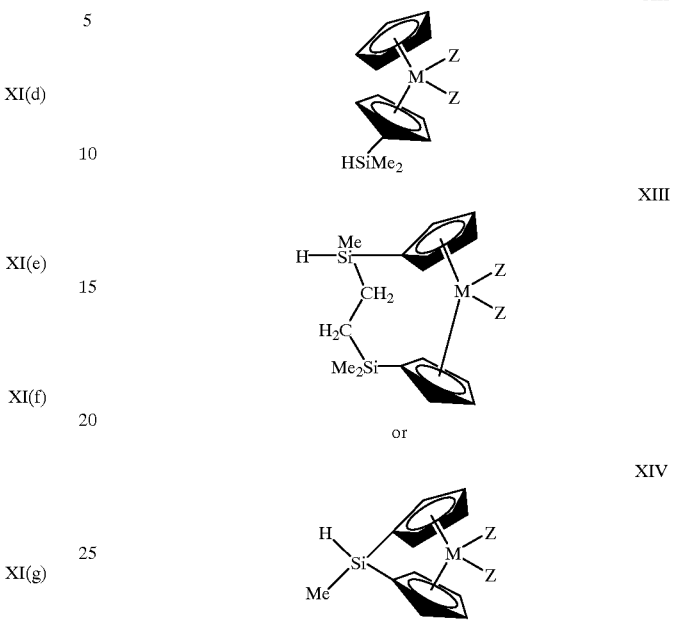

wherein Z is a chalcogen, halide, alkyl, aryl, or amide substituent, and M is the Group 4 metal.

The metallocene reagent can also be

XV wherein Z is a chalcogen, halide, alkyl, aryl, or amide substituent, M is the Group 4 metal, R is a group such as alkyl, or aryl, n=0–4, and m=0–5. Here, the metallocene is connected to the dendrimer arms by carbonyl group hydrosilylation and the linkage is through an Si—O bond via Si—H addition to the C=O bond.

A Group 4 metal-containing group, such as a metallocene substituent, can be introduced at an internal site or sites in the dendrimer. As used herein in the specification and claims, an "internal site" is a position on a dendrimer arm intermediate between the dendrimer core and the end of the dendrimer arm or dendrimer periphery. The Group 4 metal-containing group can be introduced at an internal site by introducing a reactive functionality at a dendrimer internal site and reacting the reactive functionality with the Group 4 metal-containing reagent so that the Group 4 metal is introduced at the dendrimer internal site.

For example, internal site metallocene substituent introduction can be accomplished using a silicon hydride that contains a cleavable substituent, e.g., PhSiHCl$_2$, wherein the Ph—Si bond is easily cleaved, in step (b) of the method for synthesizing the dendrimer followed by; (1) building the dendrimer out to a selected $G_n$ generation; (2) terminating the dendrimer arm or arms with an unreactive functionality, e.g., SiMe$_3$; (3) cleaving the Si—Ph bond or bonds with HX (X=Br or O$_3$SCF$_3$) and reacting the resulting product with LiAlH$_4$ (Si—Ph→Si—X→Si—H sequence); and, finally, (3) reacting the Si—H product with a CH$_2$=CH containing metallocene, as given, e.g., by formulas I, II, IV, V, VI, VII, VIII, IX, or X. Step (2) can be performed at the G$_n$ i.e., the second generation stage of dendrimer building according to step (1).

Several representative, but not limiting, reactions for preparation of a Group 4 metal-containing carbosilane dendrimer from a G$_n$ generation carbosilane dendrimer and a metallocene substituent-containing reagent are as follows. These reactions can be representative of dendrimers formed by hydrosilylation/alkenylation methods or cascade methods. For simplicity, only one arm of the multiple-armed dendrimer is shown in detail and the rest of the dendrimer is represented by ○. The Roman numerals refer generally to a metallocene reagent containing the metallocene substituent identified by the same Roman numeral as already given in the specification of this patent application.

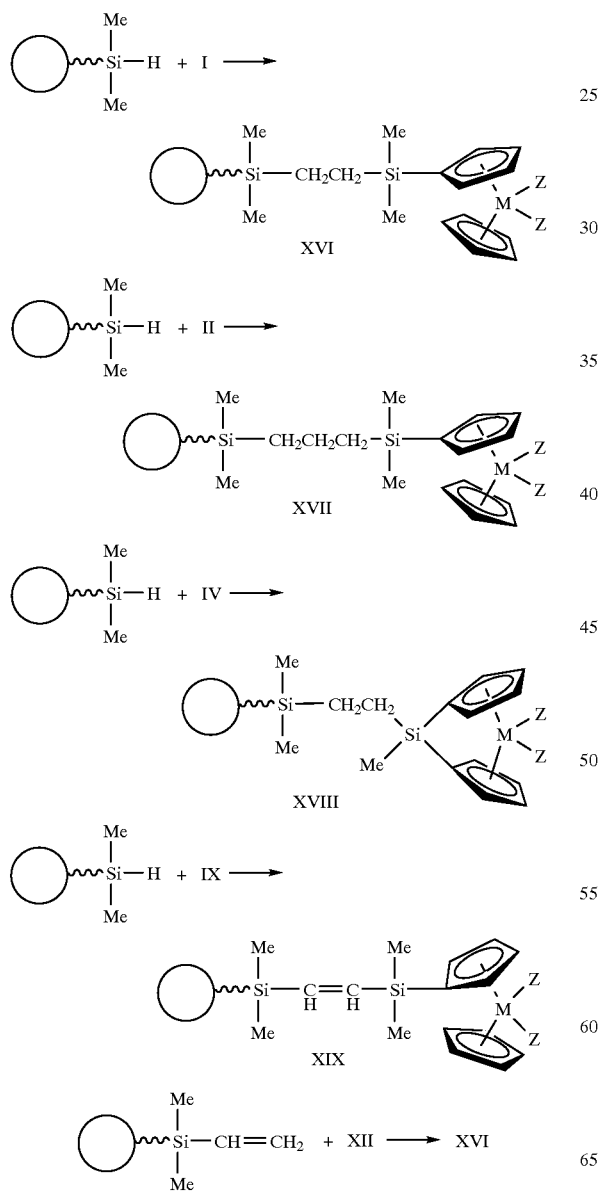

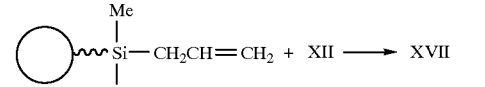

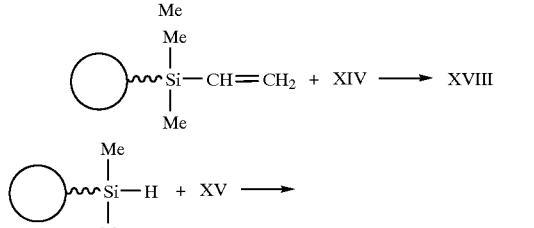

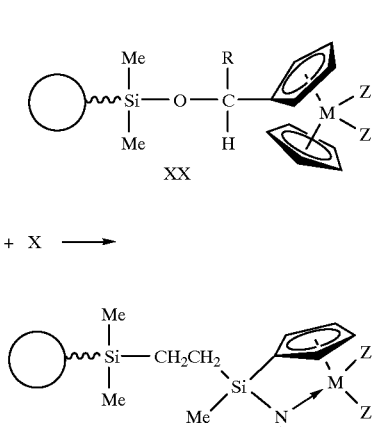

The dendrimers of the present invention can be anchored to a solid phase refractory oxide, such as alumina, silica, zirconia and the like, or to an insoluble polymer such as cross-linked polystyrene. Such anchored dendrimers can be used as anchored homogeneous catalysts.

The anchored dendrimers can be prepared by growing dendrimers from core molecules to a desired generation, G$_n$, and with some number, m, SiMe$_2$H termini at the dendrimer periphery, according to the methods already described. However, in the final step of metal-containing reagent (such as a metallocene) addition, an insufficient amount of metallocene reagent, such as a CH$_2$=CH-containing metallocene as given by formulas I–X, is reacted with the SiMe$_2$H terminated G$_n$ dendrimer. For example, using a twelve-armed G$_n$ dendrimer, only eight of the twelve arms can be reacted with the CH$_2$=CH-containing metallocene, thus leaving four SiMe$_2$H terminated arms remaining. Sufficient CH$_2$=CHSi(OEt)$_3$ can then be added in the presence of a platinum catalyst to react with the remaining dendrimer SiMe$_2$H terminated arms. Such a possible reaction sequence is shown schematically below.

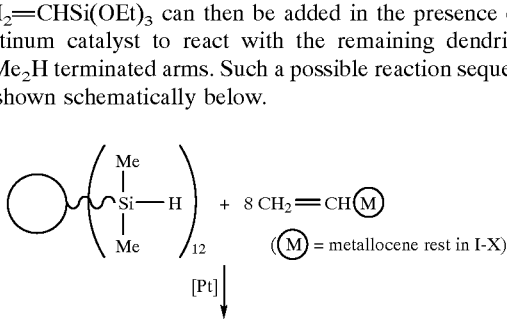

-continued

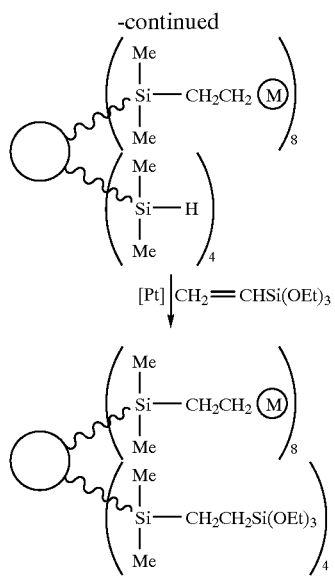

In general, anchored dendrimers include an end group that attaches chemically to the solid phase support and the end group is selected based on the surface chemistry of the solid phase support.

Figure 4:
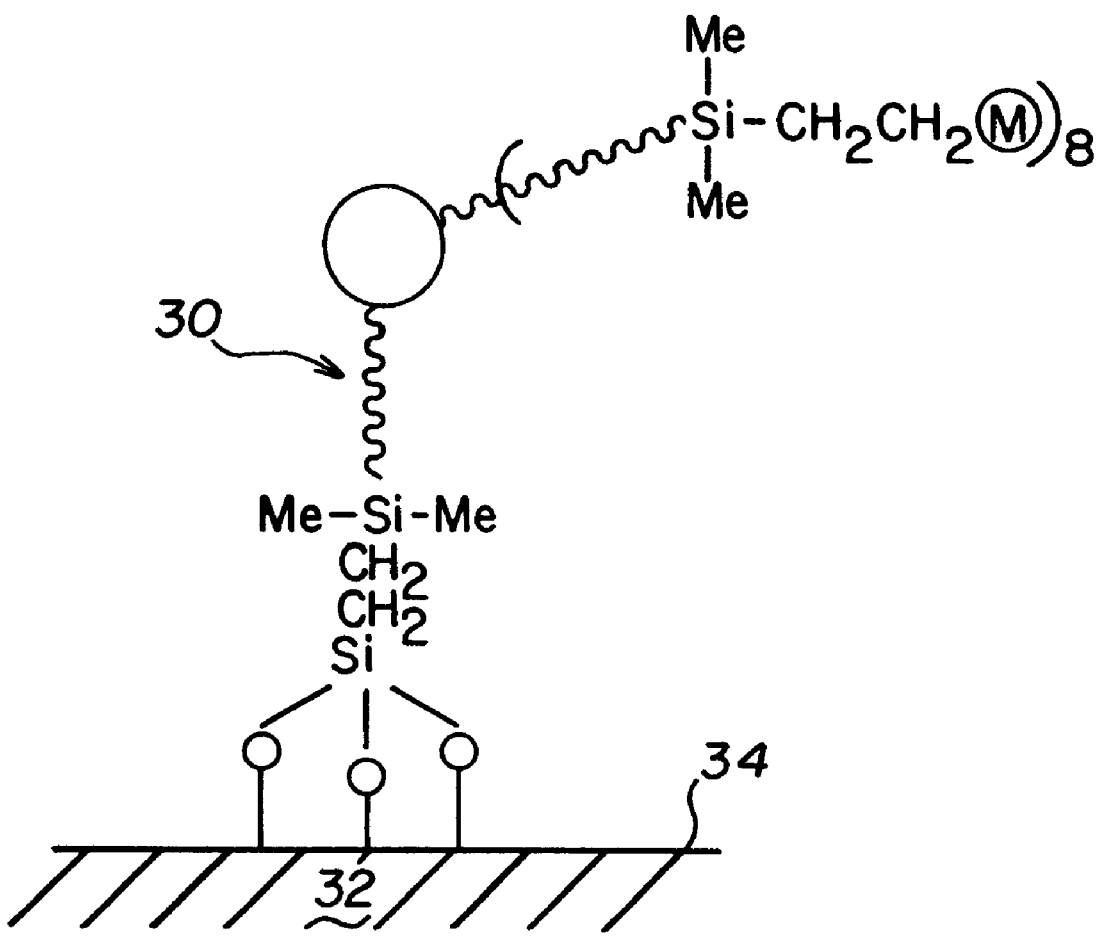
FIG. 4 is a schematic illustration of an anchored dendrimer of the invention.

The $Si(OEt)_3$ functionalities bind to hydroxyl-containing surfaces, such as, for example, those of alumina and silica, to produce an immobilized, i.e., anchored dendrimer. FIG. 4 is a schematic illustration of anchored dendrimer 30 immobilized on solid phase alumina support 32 at support surface 34. Such supported dendrimer catalysts can be used to catalyze the gas phase polymerization of olefins.

Allyltriethoxysilane can be used in place of the vinyltriethoxysilane already described to yield an anchoring dendrimer arm

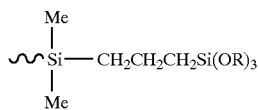

where R is an alkyl, methyl or ethyl group.

Cascade Synthesis Methods

The following describes certain aspects of the present invention with respect to using cascade synthesis methods of forming group 4 metal-containing organosilicon dendrimers.

In embodiments which use the cascade synthesis method of the invention, the starting monomers can be $HSi(CH=CH_2)_3$; $HSi(CH_2CH=CH_2)_3$; $HSi[(CH_2)_nCH=CH_2]_3$, where n=2–20; $R(H)Si(CH=CH_2)_2$; $R(H)Si(CH_2CH=CH_2)_2$; or $R(H)Si[(CH_2)_nCH=CH_2]_2$, where n=2–20, R is a methyl or higher alkyl, phenyl or substituted phenyl, halogen, alkoxy, aryloxy or a dialkylamino group.

The hydrosilylation step of the cascade synthesis can be induced by exposing the starting monomers to a catalytic reagent such as, but not limited to a transition metal catalyst such as complexes containing Pt, Pd, Rh, Ru, Ni, or Ti; organic peroxides; azo compounds; and supported transition metal catalysts such as Pt/charcoal, Pt/asbestos, and Raney Ni. Alternatively, the hydrosilylation reaction can be induced by exposing the starting monomers to ultraviolet radiation or by heating the monomers. The hydrosilylation reaction can then be allowed to proceed until substantially all of the starting monomers have been consumed. The intermediate organosilicon dendrimer produced in the cascade synthesis method can further include a dendrimer periphery and, in this embodiment, the hydrosilylation reaction can be allowed to proceed until steric congestion at the dendrimer periphery causes growth to cease.

Figure 3:
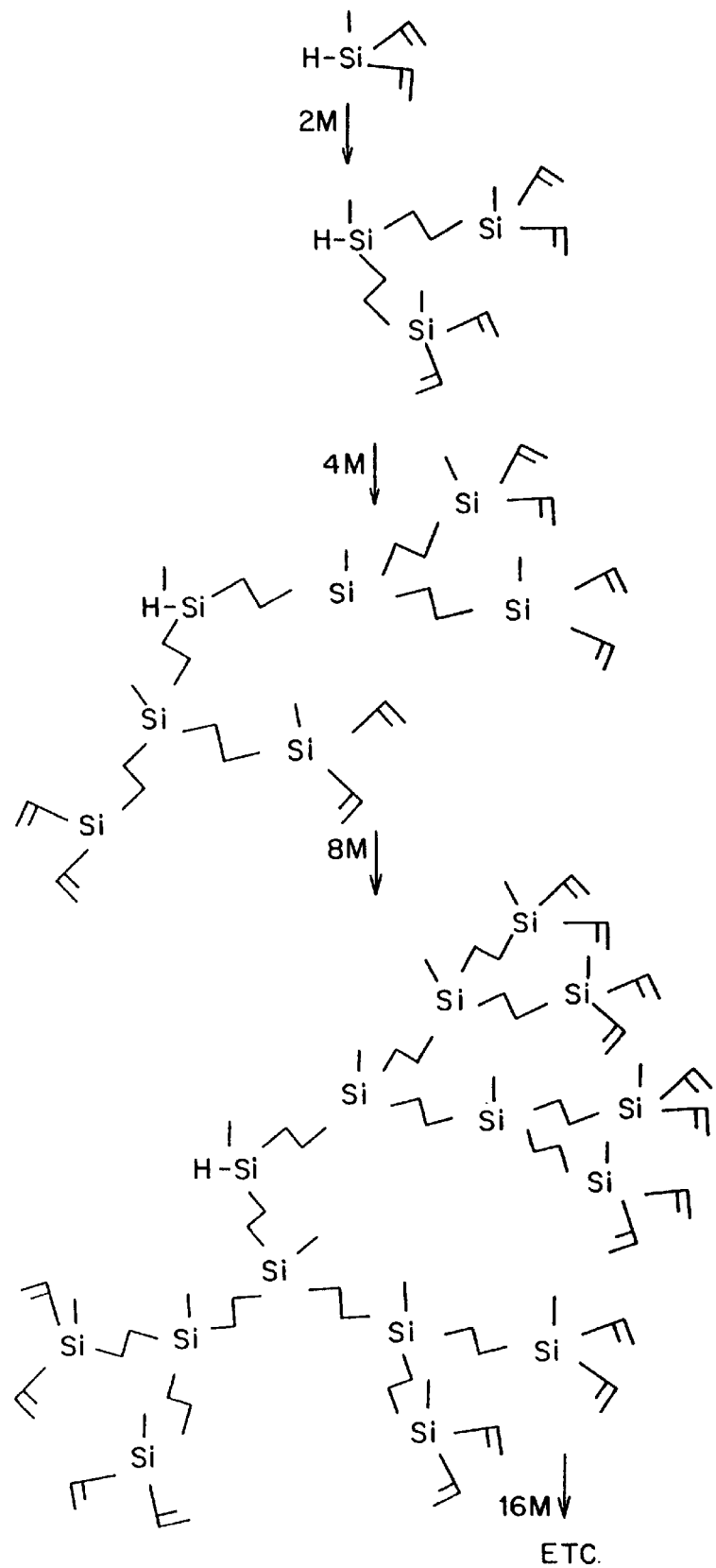
FIG. 3 is an idealized representation of cascade growth of a carbosilane dendrimer.

An idealized cascade synthesis scheme is represented pictorially in FIG. 3 where "M" represents the monomer being added at each stage of the synthesis. The growth according to this scheme is not and is not required to be regular. Even when all the monomers have been consumed, there will still be many unreacted $=CH_2$ groups in the as-synthesized dendrimer, along with still active catalyst, such as, for example, transition metal Pt catalyst. Thus, the dendrimer is a "living polymer", i.e., one capable of further growth upon addition of additional monomers to yield dendrimers of greater molecular weight.

After the hydrosilylation step of the cascade synthesis additional monomers can be provided and reacted with the intermediate organosilicon dendrimer. The additional monomers can have the same chemical composition as the starting monomers or, alternatively, have a different chemical composition than the starting monomers. Monomers of different chemical composition can be monomers such as $H(R)Si[(CH_2)_nCH=CH_2]_2$ where R is $(CH_2)_nCH=CH_2$, alkyl, aryl, halogen, alkoxy, aryloxy, or dialkylamino and n=0–20.

In an embodiment of the cascade synthesis, the intermediate organosilicon dendrimer can further include a reactive $=CH_2$ group or groups that can be deactivated in a subsequent step of the synthesis. Deactivation of the reactive $=CH_2$ group or groups can be accomplished by addition of a silicon hydride of composition $R_3SiH$ where R is alkyl, aryl, halogen, alkoxy, aryloxy, siloxy, or dialkylamino or mixtures thereof. The silicon hydride can be, but is not limited to, $Me_2SiHCl$, $MeSiHCl_2$, $HSiCl_3$, $HSi(OEt)_3$, $HSi(OMe)_3$, $HSi(NMe_2)_3$, $PhSiHCl_2$ or $HSiMe_2OSiMe_3$. The addition can be catalyzed by a transition metal or other catalyst, such as, for example, a Pt catalyst.

In another embodiment of the cascade synthesis, an intermediate organosilicon dendrimer including a reactive $CH=CH_2$ group can be prepared and reacted with a reagent of the general formula $R_2SiHX$ where R is Me, Et, higher alkyl, or aryl and X is F, Cl, Br, I or alkoxy and including a Si—X bond. The thus introduced Si—X bond is then reduced to produce a reactive Si—H bond that is then further reacted with the Group 4 metal-containing reagent to form the organosilicon dendrimer including a Group 4 metal. Reduction of the Si—X bond can be accomplished using a reducing agent, such as, for example, $LiAlH_4$. Reaction with the Group 4 metal-containing reagent can be carried out in the presence of a catalyst, such as, for example, the Karstedt catalyst, a solution of 1,3-divinyltetramethyldisiloxane-platinum complex in xylene, 2–3% Pt concentration.

The Group 4 metal-containing reagent can be a metallocene reagent having the general formula I, II, III, IV, V, VI, VII, VIII, IX, X, XI, XI(a), XI(b) or the following:

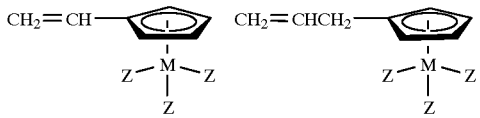

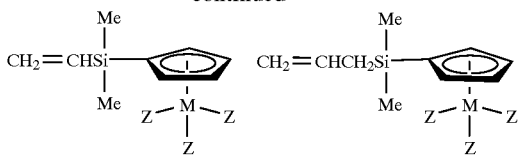

Alternatively, the Group 4 metal-containing reagent can include a metallocene substituent characterized by the formula XI(c), IX(d), XI(e), IX(f), XI(g), XI(h), XI(i) or XI(j).

The intermediate organosilicon dendrimer can contain a =CH$_2$ unit and the Group 4 metal-containing reagent can then be XII, XIII or XIV.

The Group 4 metal-containing reagent can also be XV.

The cascade synthesis method can be used to prepare an anchored dendrimer by providing an OH-containing substrate, and carrying out the hydrosilylation to produce an intermediate organosilicon dendrimer including a reactive CH=CH$_2$ group. The step of reacting the intermediate organosilicon dendrimer with the Group 4 metal-containing reagent further includes adding a reagent of the general formula R$_2$SiHX where R is Me, Et, higher alkyl, or aryl and X is F, Cl, Br, I or alkoxy and including a Si—X bond. The Si—X bond is reduced to produce a reactive Si—H bond. The reactive Si—H bond is reacted with a deficiency of the Group 4 metal-containing reagent further including a vinyl, allyl or alkynyl substituent to add to up to 90% of all available CH=CH$_2$ or CH≡CH groups to produce an intermediate product. The intermediate product is subsequently reacted with a vinyl silane or allyl silane that includes an SiX$_3$, substituent where X is OMe, OEt, Cl or NMe$_2$ to produce an anchorable organosilicon dendrimer including a Group 4 metal. The vinyl or allyl silane can be, for example, of the type CH$_2$=CHSiX$_3$ or CH$_2$=CHCH$_2$SiX$_3$ where X is as already described and can be reacted with up to 30% of the originally available CH=CH$_2$ or CH≡CH groups. The thus-prepared anchorable organosilicon dendrimer including a Group 4 metal can be anchored to the OH-containing substrate, such as, for example, by reaction with the SiX$_3$ groups. In the core-based cascade synthesis method, the Group 4 metal-containing reagent can include a Si—H bond and be chosen from among, but is not limited to, the already-described Group 4 metal-containing reagents.

For example, a carbosilane dendrimer can be prepared using a core-based cascade synthesis starting with a Si[(CH$_2$)$_n$CH=CH$_2$]$_4$, n=0–20, core molecule and slowly adding four (4) molar equivalents of (CH$_2$=CHCH$_2$)$_2$(CH$_3$)SiH to one of Si(CH=CH$_2$)$_4$ in the presence of the Karstedt catalyst. A high yield of Si[CH$_2$CH$_2$Si(CH$_3$)(CH$_2$CH=CH$_2$)$_2$]$_4$ is obtained. Further slow addition of eight (8) molar equivalents of (CH$_2$=CHCH$_2$)$_2$(CH$_3$)SiH to this product gave a viscous oil dendrimer of molecular weight 2113 as determined by gel permeation chromatography (GPC) using a polystyrene standard.

Starting with such a tetrafunctional core molecule will give a more symmetrical dendrimer than when the monomer is used in the absence of such a core molecule. However, this dendrimer product will still be less regular than a dendrimer grown by the divergent procedure.

A carbosilane dendrimer can also be grown out from a Si[(CH$_2$)$_n$CH=CH$_2$]$_4$ core molecule in the presence of the Karstedt catalyst to give such a cascade dendrimer.

In the core-based cascade synthesis method, the intermediate organosilicon dendrimer can be reacted with a reagent of the general formula R$_2$SiHX where R is Me, Et, higher alkyl, or aryl and X is F, Cl, Br, I or alkoxy and including a Si—X bond. The Si—X bond can be reduced to produce a reactive Si—H bond which can be subsequently reacted with the Group 4 metal-containing reagent to form the organosilicon dendrimer including a Group 4 metal.

The core-based cascade synthesis method, like the cascade method, can be used to produce a Group 4 metal-containing dendrimer anchored to a solid phase refractory oxide, such as alumina, silica, zirconia and the like, or to an insoluble polymer such as poly(vinyl alcohol). Such anchored dendrimers can be used as catalysts, such as, for example, in polymerization of olefins.

In an embodiment of the core-based cascade synthesis, an OH-containing substrate is provided and the intermediate organosilicon dendrimer is reacted with a reagent such as HSiX$_3$ or HSiRX$_2$ where X is Cl, Br, I, OMe, OEt, Oalkyl, Oaryl, or NMe$_2$ and R is Me, Ph, alkyl, or aryl to produce an anchorable dendrimer. The anchorable dendrimer can be exposed to the OH-containing substrate so that said anchorable dendrimer becomes anchored to the substrate.

In the core-based cascade method for synthesizing a Group 4 transition metal-containing organosilicon dendrimer including a desired functionality positioned at an internal site on a dendrimer arm, four (4) molar equivalents of the first reagent can be used. The reagent reacted with the reactive Si—H peripheral dendrimer arm ends can be of the type RCH=CH$_2$ where R is alkyl, aryl or Me$_3$Si. Suitable Group 4 metal-containing reagents for producing a functionality at an internal location on a dendrimer arm have already been described in other embodiments of the invention.

In an embodiment of the core-based method for synthesizing a Group 4 transition metal-containing organosilicon dendrimer including growing the core molecule out to a larger size, four (4) molar equivalents of [CH$_2$=CH(CH$_2$)$_n$]R$_2$SiH where R is methyl or alkyl and n=0–20 can be reacted with the core molecule to form an intermediate product. The intermediate product subsequently can be reacted with four (4) molar equivalents of [CH$_2$=CH(CH$_2$)$_n$]$_2$C$_6$H$_5$SiH where n=0–20 to form a second intermediate product.

Uses of Group 4 Metal-Containing Organosilicon Dendrimers

The Group 4 metal-containing organosilicon dendrimers of the present invention can be used in olefin polymerization or copolymerization methods wherein one or more olefin monomers are contacted with the organosilicon dendrimer catalyst in solution or in gas phase so that the olefin monomers are polymerized or copolymerized to form a polyolefin.

The monomers can be ethylene and a co-catalyst such as methylalumoxane (MAO), B(C$_6$F$_5$)$_3$, a Ph$_3$C$^+$ salt of the (C$_6$F$_5$)$_4$ B$^-$ anion, or an organic ammonium salt of the (C$_6$Fr3)$_4$B$^-$ aninon can be provided. Other salts of anions of very low nucleophilicity also can be used.

The monomers can be α-olefins, such as propylene, 1-butene, styrene, and higher α-olefins, cyclic olefins such as cyclopentene, or norbornene, 1,3-dienes such as 1,3-butadiene or isoprene, and a co-catalyst such as methylalumoxane (MAO), B(C$_6$F$_5$)$_3$, a Ph$_3$C$^+$ salt of the (C$_6$F$_5$)$_4$B$^-$ anion, or an organic ammonium salt of the (C$_6$F$_5$)$_4$B$^-$ anion can be provided.

The Group 4 metal-containing organosilicon dendrimers of the present invention can also be used as catalysts for dehydrogenative condensation of silane monomers to form a polysilane as shown in the equation below.

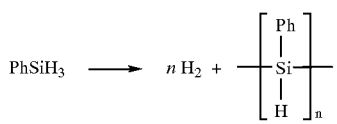

The homo- and copolymerizations can be completed at a temperature between −60° C. and 120° C., preferably between −10° C. and 60° C. using aliphatic or cycloaliphatic hydrocarbon solvents such as hexane or cyclohexane. More preferably, an aromatic hydrocarbon solvent such as toluene is used. Additionally, the polymerization can be done in the gas phase.

The metallocene concentration is in the range of $10^{-3}$ to $10^{-8}$ mol/ml solvent, preferably in the range of $10^{-4}$ to $10^{-6}$ mol/ml solvent. The cocatalyst concentration is in the range of $10^{-3}$ to $10^{-1}$ mol/ml, preferably in the range of $10^{-2}$ to $10^{-1}$ mol/ml.

The desired reactions can be carried out in solution suspension, or bulk, using pressures in the range of 0.1 bar to 50 bar, or preferably between 0.5 bar to 10 bar, whereby the homopolymerizations of cyclic olefins are done under normal pressure.

In order further to illustrate the present invention, the following examples are provided. The particular compounds, processes and conditions utilized in the examples are meant to be illustrative of the present invention and are not limited thereto.

EXAMPLES

The following Examples 1–27 are provided to show how metallocene complexes and Group 4 metal-containing carbosilane dendrimers were prepared, characterized, and used as polymerization catalysts.

In the examples 1–27, the general dendrimer synthesis procedure as described in Seyferth et al., Organometallics, 13 (1994) 2682–2690 was followed. Typically, the core molecule was tetravinylsilane, $(CH_2=CH)_4Si$ and successive dendrimer generations were built up from this core molecule by successive platinum-catalyzed hydrosilylations of all Si—CH=CH$_2$ functions with HSiCl$_3$ or CH$_3$SiHCl$_2$ and vinylation of the Si—Cl functions thus introduced with vinylmagnesium bromide, $CH_2$=CHMgBr, in tetrahydrofuran (THF). The manner according to which the final hydrosilylation was accomplished was selected according to whether a Si—H function or an unsaturated organic function was the desired terminus for the arms of the dendrimer to be reacted with the metallocene reagent. To obtain a Si—H terminus, the final hydrosilylation was effected with Me$_2$SiHCl and the terminal Si—Cl bonds were then reduced with LiAlH$_4$. To obtain a Si—CH=CH$_2$ or Si—CH$_2$CH=CH$_2$ terminus, the final hydrosilylation was effected with Me$_2$SiHCl and the terminal Si—Cl bonds were vinylated with $CH_2$=CHMgBr or $CH_2$=CHCH$_2$MgCl.

All reactions were carried out under an inert atmosphere, either nitrogen or argon. Solvents were purified before use according to methods well known to one skilled in the art. The Karstedt catalyst (a solution of 1,3-divinyltetramethyldisiloxane-platinum complex in xylene, 2–3% Pt concentration) was purchased from Aldrich Chemical Co, Milwaukee, Wis.

Materials used to filter solutions include Florisil®, an activated magnesium silicate purchased from Aldrich Chemical Co., and Celite® (Celite 545®), a diatomaceous earth purchased from Fisher Scientific Co.

The following Examples 1–8 describe preparation of titanocene, zirconocene and hafnocene complexes.

The following Examples 28–41 are provided to show how carbosilane dendrimers were prepared, characterized, and used as polymerization catalysts using the cascade or core-based synthesis methods of the invention.

In the examples that follow, all reactions were carried out in flame-dried glassware in an inert atmosphere such as argon or nitrogen. All solvents were dried prior to use, with standard procedures well known to one skilled in the art.

Starting monomers were prepared using standard Grignard vinylation and allylation of CH$_3$SiHCl$_2$ and HSiCl$_3$. The Karstedt catalyst solution was purchased from Sigma Aldrich, Milwaukee, Wis.

Molecular weights were determined in benzene or toluene solution by vapor pressure osmometry (VPO).

Example 1

Preparation of Me$_2$(CH$_2$—CH)SiC$_5$H$_4$(C$_5$H$_5$)TiCl$_2$

A 250 mL Schienk flask equipped with a magnetic stirbar, a reflux condenser and a rubber septum was charged with 60 mL of THF and 3.30 g (22 mmol) of Me$_2$(CH$_2$=CH)SiC$_5$H$_5$. To this solution was added at −40° C., slowly by syringe, 13.74 mL of a 1.6 M solution of n-BuLi (22 mmol) in hexane. After it had been stirred at room temperature for 20 minutes, the resulting solution of Me$_2$(CH$_2$=CH)SiC$_5$H$_4$Li was cooled to −10° C. and 4.82 g (22 mmol) of C$_5$H$_5$TiCl$_3$ in 30 mL of THF was added slowly. The reaction mixture was stirred at room temperature for 12 h and at reflux for another 2 h. Subsequently, the volatiles were removed at reduced pressure and the residue was dissolved in a mixture of 30 mL of toluene and 15 mL of CH$_2$Cl$_2$. The solution was filtered through Celite™. The product crystallized when the filtrate was stored at −30° C. for 12 h. The product was isolated as purple crystals, washed with two 5 mL portions of hexane and dried in vacuum; yield, 5.86 g (80%); melting point 145–146° C. Anal. Calcd. for C$_{14}$H$_{18}$Cl$_2$SiTi:C, 50.47; H, 5.44. Found: C, 51.05; H, 5.54. The $^1$H, $^{13}$C and $^{29}$Si NMR spectra were in agreement with the indicated structure.

Example 2

Preparation of Me$_2$HSiC$_5$H$_4$(C$_5$H$_5$)TiCl$_2$

The same procedure as already described in Example 1 was used to react 2.83 g (22.8 mmol) of Me$_2$HSiC$_5$H$_5$ in 50 mL of THF and an equimolar amount of n-BuLi in hexane to generate the lithium cyclopentadienide reagent. The lithium cyclopentadienide reagent was then reacted with 5.0 g (22.8 nmol) of C$_5$H$_5$TiCl$_3$. Once the reaction was complete, the solvents were removed at reduced pressure and the residue was taken up in benzene and filtered through Celite™. The residue obtained on removal of the benzene was recrystallized from hexane/toluene.

Example 3

Preparation of Me$_2$HSiC$_5$H$_5$(C$_5$H$_5$)TiCl$_2$

Substantially the same procedure as described in foregoing Example 1 was used to react 6.65 mmol of Me$_2$(CH$_2$=CH)SiC$_5$H$_4$Li from 6.65 mmol each of n-BuLi and Me$_2$(CH$_2$=CH)SiC$_5$H$_5$ and 2.2 g (6.65 mmol) of C$_5$Me$_5$ZrCl$_3$ in 30 mL of THF. After the volatiles were removed at reduced pressure, the residue was taken up in 30 mL of toluene. The toluene solution was filtered through Celite™ and then evaporated in vacuum. The solid residue was washed with two 5 mL portions of cold hexane and recrystallized from hexane, giving 1.61 g (54%) of white crystals, melting point 121–122° C. Anal. Calcd. for $C_{19}H_{28}Cl_2SiZr$: C, 51.08; H, 6.32. Found: C, 51.24; H, 6.41. The $^1H$, $^{13}C$ and $^{29}Si$ NMR spectra of the product were in agreement with the indicated structure.

Example 4

Preparation of $Me_2(CH=CH)SiC_5H_5(C_5H_5)ZrCl_2$

The apparatus already described in the foregoing Example 1 was charged with 10.0 g of ZrCl, and 90 mL of $CH_2Cl_2$ to form a solution to which was added slowly at 0° C. by syringe 6.4 mL (43 mmol) of dimethyl sulfide. The resulting solution was stirred for 30 min and then 5.94 g (43 mmol) of $Me_2SiC_5H_5$ was added slowly. After the mixture was stirred at room temperature for 1 h, the volatiles were removed at reduced pressure and the residue was dissolved in 60 mL of THF. To this solution 6.70 g (43 mmol) of $Me_2(CH_2=CH)SiC_5H_4Li$ in 50 mL of THF at −20° C. was added. The reaction mixture was stirred at room temperature for 12 h and for another 2 h at 50° C., then was concentrated to 20 mL. Toluene (40 mL) was added and the solution was filtered through Celite™. After removal of most of the solvents at reduced pressure, 50 mL of hexane was added. The resulting crystalline residue was washed with 5 mL of cold hexane and recrystallized from hexane to give 9.4 g (58%) of white crystals, melting point 116–117° C. Anal. Calcd. for $C_{14}H_{18}Cl_2SiZr$: C, 44.86; H, 4.82. Found: C, 43.74; H 4.91. The $^1H$, $^{13}C$ and $^{29}Si$ NMR spectra were in agreement with the indicated structure.

Example 5

Preparation of $(\mu\text{-}Me(CH_2=CH)Si)(C_5H_4)_2ZrCl_2$

The same apparatus as already described in Example 1 was charged with 5.0 g (25.0 mmol) of $Me(CH_2=CH)Si(C_5H_5)$, and 60 mL of THF to form a solution. This solution was cooled to −40° C. and 19.9 mL of 2.5 $\underline{M}$ n-BuLi (49.8 mmol) in hexane was added slowly by syringe. The resulting mixture was stirred for 1 h at room temperature, then cooled to −10° C. and 5.81 g (24.9 mmol) of $ZrCl_4$ was added. The reaction mixture was stirred for 48 h at room temperature. Subsequently, the THF was removed at reduced pressure, and the residue was taken up in 100 mL of $CH_2Cl_2$. This solution was filtered through Celite™. The filtrate was concentrated to 40 mL and stored at −30° C. for 12 h. The crystalline solid that formed was washed with two 5 mL portions of cold $CH_2Cl_2$ and dried in vacuo. The yield was 3.3. g (37%) and the melting point was 239–240° C. Anal. Calcd. for $C_{13}H_{14}Cl_2SiZr$: C, 43.32; H, 3.91. Found: C, 43.14; H 3.97. $^1H$ NMR ($CDCl_3$): δ 0.78 (s, 3H, $SiCH_3$), 6.0 (m, 4H, $C_5H_4$), 6.26–6.54 (m, 3 H, $CH_2=CH$), 6.92–6.99 (m, 4H, $C_5H_4$). $^{13}C\{^1H\}$ NMR($CDCl_3$): $δ_c$ −6.30 ($SiCH_3$), 107.89 ($C_5H_4$), 114.29 ($C_5H_4$), 115.12 ($C_5H_4$), 127.68 ($C_5H_4$), 129.51 ($C_5H_4$), 130.19 ($\underline{C}H_2=CH$), 138.45 ($CH_2=\underline{C}H$). For NMR measurements, Si atoms are numbered from the dendrimer core to the dendrimer periphery and that number indicated by a superscript to the right of its chemical symbol.

Example 6

Preparation of $(Me_2HSi_5CH_4)(Me_3SiC_5H_4)TiCl_2$

Using the same apparatus as described in the foregoing Example 1, 5.3 mL of a solution of 2.5 $\underline{M}$ n-BuLi in hexane (13.33 mmol) was added to a solution of 1.66 g (13.33 mmol) of $Me_2HSiC_5H_5$ in 30 mL of THF. The mixture was stirred at room temperature for 20 min. Subsequently, a solution of 3.88 g (13.33 mmol) of $Me_3SiC_5H_4TiCl_3$ in 20 mL of THF was added slowly at −20° C. The resulting red reaction mixture was stirred for 12 h at room temperature. Removal of THF at reduced pressure was followed by solution of the residue in benzene and filtration through Celite™. Evaporation of the filtrate left a red solid that was recrystallized from hexane/toluene to give orange crystals (2.8 g, 55%). Anal. Calcd. for $C_{15}H_{24}C_{12}SiTi$: C, 47.50; H, 6.38. Found: C, 47.56; H, 6.55. $^1H$ NMR ($C_6D_6$): δ 0.25–0.40 (m, 15H, $SiCH_3$), 4.48–4.65 (m, 1 H, SiH), 5.85–6.02 (m, 4H, $C_5H_4$), 6.38–6.52 (m, 4H, $C_5H_4$). For the NMR analysis, Si atoms are numbered from the core outward toward the periphery of the dendrimer and that number indicated by a superscript to the right of its chemical symbol.

Example 7

Preparation of $(Me_2(CH_2=CH)SiC_5H_4)(C_5H_4)HfCl_2$

A 250 mL schlenk flask equipped with a magnetic stir bar and a rubber septum was charged with 50 mL of $CH_2Cl_2$ and 8.0 g (25.0 mmol) of $HfCl_4$. To this solution, 3.7 mL (50.0 mmol) of $SMe_2$ was added slowly by syringe at 0° C. After further stirring for 30 min, 8.88 g (25.0 mmol) of $(n-C_4H_9)_3SnC_5H_5$ was slowly added. The resulting mixture was stirred for 12 h at room temperature. The solution was concentrated to 20 mL and 30 mL of n-hexane was added. The remaining solid was filtered and washed twice with 20 mL of n-hexane. Then, the solid was dissolved in 80 mL of THF. After removing the THF at reduced pressure, 8.7 g (17.6 mmol) of $C_5H_5HfCl_3(THF)_2$ remained. 8.5 g (17.2 mmol) of $C_5H_5HfCl_3(THF)_2$ was dissolved in 60 mL of THF. A solution of 17.2 mmol of $LiC_5H_4SiMe_2Vi$, where "Vi" indicates a vinyl functional group, in 50 mL of THF was added at −20° C. The resulting mixture was stirred for 15 h at room temperature. All volatiles were removed at reduced pressure at room temperature. The residue was dissolved in 80 mL of toluene and filtered through Celite™. The solution was concentrated to 25 mL and kept for 12 h at −30° C. The crystals obtained were filtered at −10° C. and washed with 10 mL of cold toluene. The resulting white crystals were dried in vacuum. A yield of 3.83 g (48.0%) with melting point 108–110° C. was obtained. Anal. Calcd. for $C_{14}H_{18}Cl_2HfSi$: C, 36.26; H, 3.91. Found: C, 34.85; H, 3.99. $^1H$ NMR ($CDCl_3$): δ 0.360 (s, 6H, $SiCH_3$), 5.700–6.320 (m, 3 $CH_2=CH$) 6.337 (m, 5H, $C_5H_5$), 6.443 (m, 2H, $C_5H_4$), 6.621 (m, 2H, $C_5H_4$). $^{13}C\{^1H\}$ NMR ($CDCl_3$): δ −2.03 (s, $SiCH_3$), 114.66 (s, $C_5H_5$), 116.52 (s, $C_5H_4$), 121.30 (s, $C_5H_4$), 124.25 (s, $C_5H_4$), 133.02 (s,$\underline{C}H_2=CH$), 137.97 (s, $CH_2=\underline{C}H$). $^{29}Si\{^1H\}$ NMR ($CDCl_3$) $δ_{Si}$ −14.6 (s, Si ($C_5H_4$)). For the NMR analysis, Si atoms are numbered from the core outward toward the periphery of the dendrimer and that number indicated by a superscript to the right of its chemical symbol.

Example 8

Preparation of $(Me_2(CH_2=CHCH_2)SiC_5H_4)(C_5H_4)TiCl_2$

A 250 mL Schlenk flask equipped with a magnetic stir bar and a rubber septum was charged with 100 mL of THF and 5.87 g (35.7 mmol) of $Me_2(CH_2=CHCH_2)SiC_5H_5$. To this solution was added at −40° C., slowly by syringe, 14.3 mL of a 2.5 M solution of n-BuLi (35.7 mmol) in hexane. After it had been stirred at room temperature for 20 minutes, the resulting solution of $Me_2(CH_2=CHCH_2)SiC_5H_4Li$ was cooled to $-10°$ C. and 7.84 g (35.7 mmol) of $C_5H_5TiCl_3$ in 60 mL of THF was added slowly. The reaction mixture was stirred at room temperature for 12 h. Subsequently, the volatiles were removed at reduced pressure and the residue was dissolved in 50 mL of $CH_2Cl_2$. The solution was filtered through Celite™ and the $CH_2CL_2$ was removed at reduced pressure. The crystallized product was washed with 30 ML of hexane. The orange crystals were collected and dried in vacuum. A yield of 11.6 g (93.5%) with melting point 148–149° C. was obtained. The $^1H$, $^{13}C$ and $^{29}Si$ NMR spectra were in agreement with the indicated structure.

The following Examples 9–20 describe the synthesis of dendrimers with Group 4 metallocene termini.

Example 9

Preparation of Si
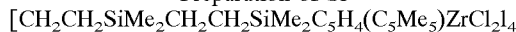
[$CH_2CH_2SiMe_2CH_2CH_2SiMe_2C_5H_4(C_5Me_5)ZrCl_2$]$_4$ A 20 mL Schlenk flask was charged with 0.4024 g (0.9 mmol) of $Me_2(CH_2=CH)SiC_5H_4(C_5Me_5)ZrCl_2$, 0.847 g (0.225 mmol) of Si $(CH_2CH_2SiMe_2H)_4$, 1 mL of THF and 20 μL of the Karstedt catalyst solution. The reaction mixture was stirred at 50° C. for 12 h. Then, 2 mL of THF were added and the solution was filtered through Celite. Volatiles were removed from the filtrate at reduced pressure, leaving a light yellow oil that was heated at 60 ° C. in high vacuum for several hours. A light yellow, waxy residue remained, 0.463 g (95%). Anal. Calcd. for $C_{92}H_{156}Cl_8Si_9Zr_4$: C, 51.07; H, 7.27. Found: C, 51.28; H, 7.46. $^1H$ NMR ($CDCl_3$): δ 0.103 (s, 6H, $Si^2CH_3$), 0.20–0.60 (m, 14H,$Si^3CH_3$, $SiCH_2$), 2.00 (s, 15H, $C_5(CH_3)_5$), 6.092 (m, 2H, $C_5H_4$), 6.432 (m, 2H, $C_5H_4$). $^{13}C$ {$^1H$} NMR ($CDCl_3$): δ$_c$ –4.38 ($Si^2CH_3$), –2.83 ($Si^3CH_3$), 2.25 ($Si^1\underline{C}H_2CH_2Si^2$), 6.49 ($Si^2CH_2\underline{C}H_2CH_2Si^3$), 12.46 ($C_5(\underline{C}H_3)_5$), 114.94 ($C_5H_4$), 124.13 ($\underline{C}_5(\underline{C}H_3)_5$, 125.28 ($C_5H_4$), 128.75 ($C_5H_4$), $^{29}Si$ {$^1H$} NMR ($CDCl_3$): δ –3.83 ($Si^3$), 5.21 ($\underline{Si}^2$), 8.77 ($Si^1$). For the NMR analysis, Si atoms are numbered from the core outward toward the periphery of the dendrimer and that number indicated by a superscript to the right of its chemical symbol.

Example 10

Preparation of $Si[CH_2CH_2SiMe_2CH_2CH_2SiMe_2C_{54}$
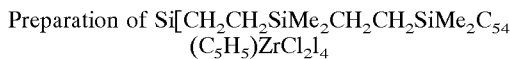
$(C_5H_5)ZrCl_2$]$_4$ The same procedure as already set forth in the foregoing Example 7 was used in the reaction of 0.5684 g (1.51 mmol) of $Me_2(CH_2=CH)SiC_5H_4(C_5H_5)ZrCl_2$ and 0.1423 g (0.377 mmol) of Si $(CH_2CH_2SiMe_2H)_4$ in 2 mL of THF in the presence of 30 μL of the Karstedt catalyst solution. The product (0.710 g, approximately 100%) was a white solid of melting point 135–136° C. Anal. Calcd. for $C_{72}H_{116}Cl_8Si_9Zr_4$: C, 45.93; H, 6.21. Found: C, 45.43; H, 6.39. $^1H$ NMR ($CDCL_3$): δ –0.094 (s, 6H, $Si^2CH_3$), 0.20–0.62 (m, 14H, $Si^3CH_3$, $SICH_2$), 6.43 (s, 5H, $C_5H_5$), 6.52 (m, 2H, $C_5H_4$), 6.68 (m, 2H, $C_5H_4$). $^{13}c$ {$^1H$} NMR ($CDCl_3$): δ –4.34 ($Si^2CH_3$), –2.81 ($Si^3$ $CH_3$), 2.51 ($Si^2\underline{C}H_2$), 6.44 ($Si^2\underline{C}H_2CH_2Si^3$), 6.59 ($Si^1CH_2\underline{C}H_2$) 8.94 ($Si_2CH_2\underline{C}H_2Si^3$), 115.84 ($C_5H_5$) 117.08 ($C_5H_4$), 125.21 ($C_5H_5$ 125.73 ($C_5H_4$) $^{29}Si$ {$^1H$} NMR ($CDCl_3$): δ –3.81 ($Si^3$), 5.43 ($Si^2$), 8.79 ($Si^1$). For the NMR analysis, Si atoms are numbered from the core outward toward the periphery of the dendrimer and that number indicated by a superscript to the right of its chemical symbol.

Example 11

Preparation of Si
[$CH_2CH_2SiMe_2C_2HCH_2SiMe_2C_5H_4(C_5H_5)TiCl_2$]$_4$ The same procedure as already described in the foregoing Example 7 was used in the reaction of 0.4987 g (0.0374 mmol) of Si $(CH_2CH_2SiMe_2H)_4$ in 2 mL of THF in the presence of 40 μL of the Karstedt catalyst solution. After the mixture had been stirred at 50° C. for 4 h, removal of volatiles at reduced pressure left a red solid of melting point 118–120° C.; 0.639 g (approximately 100%). Anal. Calcd. for $C_{72}H_{116}Cl_8Si_9Ti_4$: C, 50.58; H, 6.85. Found: C, 50.38; H, 6.82. $^1H$ NMR ($CDCl_3$): δ –0.095 (s, 6H, $Si^2CH_3$), 0.20–0.65 (m, 14H, $Si^3CH_3$, $SiCH_2$), 6.53 (s, 5H, $C_5H_5$), 6.605 (m, 2H, $C_5H_4$), 6.84 (m,2H, $C_5H_4$). $^{13}C$ ($^1H$) NMR ($CDCl_3$): δ –4.34 ($Si^2CH_3$), 2.72 ($Si^3CH^3$), 2.62 ($Si^1CH_2$), 6.64 ($Si^2\underline{C}H_2Si^3$), 6.70 ($Si^1CH_2\underline{C}CH_2$, 8.96 ($Si^2CH_2\underline{C}H_2Si^3$), 120.14 ($C^5H^5$), 121.14 ($C^5H^4$), 132.02 ($C^5H^4$) $^{29}Si$ {$^1H$} NMR ($CDCl^3$): δ$_{Si}$ –2.73 ($Si^3$), 5.39 ($Si^2$), 8.84 ($Si^1$). For the NMR analysis, Si atoms are numbered from the core outward toward the periphery of the dendrimer and that number indicated by a superscript to the right of its chemical symbol.

Example 12

Preparation of Si
[$CH_2CH_2SiMe\{CH_2CH_2SiMe_2CH_2CH_2SiMe_2C_5H_4(C_5H_5)TiCl_2\}_2$]$_4$ The same procedure as already described in the foregoing Example 7 was used in the reaction of 1.084 g (3.254 mmol) of $Me_2(CH_2=CH)SiC_5H4(C_5H_5)TiCl_2$ with 0.4109 g (0.407 mmol) of $Si[CH_2CH_2SiMe\{CH_2CH_2SiMe_2H)_2]_4$ in 5 mL of THF in the presence of 80 μL of the Karstedt catalyst solution. After the reaction mixture had been stirred at 60° C. for 72 h, it was filtered through Celite™. Removal of volatiles at reduced pressure left a red solid of melting point 65–67° C.; 1.34 g (9OP6). Anal. Calcd. for $C_{156}H_{260}C_{16}Si_{21}Ti_8$: C, 50.97; H, 7.13. Found: C, 50.83; H, 7.38. $^1H$ NMR ($CDCl_3$): δ –0.100 (s, 12H, $Si^3CH_3$), 0.05–0.63 (m, 35H, $Si^2CH_3$, $Si^4CH_3$, $SiCH_2$), 6.54 (m, 10H, $C_5H_5$), 6.60 (m, 4H, $C_5H_4$), 6.84 (m, 4H, $C_5H_4$). $^{13}C$ (1H) NMR ($CDCl_3$): δ –6.36 ($Si^2CH_3$), –4.24 ($Si^3$ $CH_3$), –2.61 ($Si^4$ CH3), 2.43 ($Si^1CH_2$), 4.52 ($Si\_\underline{C}H_2CH_2Si\_$), 4.81 ($Si^3CH_2\underline{C}H_2Si^2$) 6.67 ($Si^3\underline{C}H_2CH_2Si^4$), 6.88 ($Si^2CH_2\underline{C}H_2Si^3$), 9.01 ($Si^3CH_2\underline{C}H_2Si^4$), 120.1 ($C_5H_5$), 121.24 ($C_5H_4$ ($C_5H_4$)), 128.87 ($C_5H_4$), 131.97 ($C_5H_4$). $^{29}Si$ {$^1H$} NMR ($CDCl_3$): δ –2.73 ($Si^4$), 5.41 ($Si^3$), 7.44 ($Si^2$), 8.91 ($Si^1$). For the NMR analysis, Si atoms are numbered from the core outward toward the periphery of the dendrimer and that number indicated by a superscript to the right of its chemical symbol.

Example 13

Preparation of Si
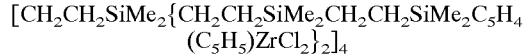
[$CH_2CH_2SiMe_2\{CH_2CH_2SiMe_2CH_2CH_2SiMe_2C_5H_4(C_5H_5)ZrCl_2\}_2$]$_4$ The same procedure as already described in the foregoing Example 7 was used in the reaction of 0.6164 g (1.637 nunol) of $Me_2(CH_2=CH)SiC_5H_5(C_5H_5)ZrCl_2$ with 0.2068 g (0.205 mmol) of $Si[CH_2CH_2SiMe\{CH_2CH_2SiMe_2H\}_2]H_4$ in 1 mL of THF in the presence of 60 μL of the Karstedt catalyst solution. After the reaction mixture had been stirred at 50° C. for 12 h, removal of volatiles at reduced pressure left 0.823 g (approximately 100%) of a light brown, waxy compound of melting point 70–72° C. Anal. Calcd. for $C_{156}H_{160}Cl_{16}Si_{21}Zr_8$: C, 46.58; H, 6.51. Found: C, 46.00; H, 6.36. $^1H$ NMR ($CDCl_3$): δ –0.102 (s, 12H, $Si^3CH_3$), 0.08–0.63 (m, 35H, $Si^3CH_3$, $Si^4CH_3$, $SiCH_2,SiCH_2$), 6.44 (m, 10H, $C_5H_5$), 6.53 (m, 4H, $C_5H_4$), 6.68 (m, 2H, $C_5H_4$). $^{13}C$ ($^1H$) NMR ($CDCl_3$): δ –6.53 ($Si^2CH_3$), –4.43 ($Si^3CH_3$), –2.88 ($Si^4CH_3$), 2.29 ($Si^1CH_2$), 4.29 ($Si^2CH_2CH_2Si^3$), 4.55

($Si^1CH_2\underline{C}CH_2Si^2$), 6.38 ($Si^3\ \underline{C}H_2CH_2Si^3$), 6.63 ($Si^2CH_2\underline{C}H_2Si^3$), 8.84 ($Si^3CH_2\underline{C}H_2Si^4$), 115.77 ($C_5H_5$), 117.05 ($C_5H_4$), 125.14 ($C_5H_4$), 125.69 ($C_5H_4$), $^{29}Si\ \{^1H\}$ NMR ($CDCl_3$): $\delta_{Si}$ −3.88 ($Si^4$), 5.30 ($Si^3$), 7.36 ($Si^2$), 9.02 ($Si^1$). For the NMR analysis, Si atoms are numbered from the core outward toward the periphery of the dendrimer and that number indicated by a superscript to the right of its chemical symbol.

Example 14

Preparation of Si{$CH_2CH_2SiMe_2CH_2CH_2Sime (C_5H_4)\ ZrCl_2$}$_4$

A 50 mL Schlenk flask was charged with 1.11 g (3.09 mmol) of ($\mu$-Me($CH_2$=CH)Si)($C_5H_4$)$_2$ZrCl$_2$, 0.2911 g (0.77 mmol) of Si($CH_2CH_2SiMe_2H$)$_4$ in 15 mL of THF and 80 gL of the Karstedt catalyst solution. After the reaction mixture was stirred at 60° C. for 24 h, removal of volatiles at reduced pressure left 1.4 g (approximately 100%) of a white solid (dried at 50° C. in vacuo) of melting point 86–88° C. Anal. Calcd. for $C_{68}H_{100}Cl_8Zr_4$: C, 44.90; H, 5.54. Found: C, 44.75; H, 5.67. $^1H$ NMR ($CDCl_3$): $\delta$ 0.046 (s, 6H, $CH_3Si^2$), 0.25–0.90 (m, 7H, $CH_3Si^3$, $Si^1CH_2CH_2Si^2$), 1.02–1.35 (m, 4H, $Si_2CH_2CH_2Si^3$), 5.90–5.97 (m, 4H, $C_5H_4$, 6.94 (m, 4H, $C_5H_4$). C $\{^1H\}$ NMR ($CDCl_3$): $\delta_c$ −7.68 ($Si^3CH_3$), −4.34 ($Si^2CH_3$), 2.81, 3.36, 5.67, 6.94 ($SiCH_2$), 108.78 ($C5H_4$), 113.90 ($C_5H_4$), 115.37 ($C_5H_4$), 127.98 ($C_5H_4$), 129.30 ($C_5H_4$). For the NMR analysis, Si atoms are numbered from the core outward toward the periphery of the dendrimer and that number indicated by a superscript to the right of its chemical symbol.

Example 15

Preparation of Si[$CH_2CH_2SiMe (CH_2CH_2SiMECH_2CH_2SiMe(C_5H_4)_2ZrCl_2)_2$]$_4$ A 20 mL Schlenk flask was charged with 450 mg (1.25 mmol) of (Me($CH_2$=CH)Si($C_5H_4$)$_2$)ZrCl$_2$, 158 mg (0.16 mmol) of Si($CH_2CH_2SiMe(CH_2CH_2SiMeH)_2$)$_4$ in 4 mL of THF and 80 $\mu$L of the Karstedt catalyst. The reaction mixture was stirred at 50° C. for 48 h, and all volatiles were removed at reduced pressure. The white solid that remained was dried in vacuum at 60° C. A yield of 0.60 g (approximately 100%) was obtained. Anal. Calcd. for $C_{148}H_{228}Cl_{16}Si_{21}Zr_8$: C, 45.65; H, 5.90. Found: C, 45.76; H, 6.15. $^1H$ NMR ($CDCl_3$): $\delta$ −0.15 (sg, 15H, $Si^2CH_3,Si^3CH_3$), 0.25–0.90 (sg, 18H, $Si^4CH_3$, $SiCH_2$), 1.00–1.30 (m, 8H, $Si^3(CH_2)_2Si^4$), 5.95 (m, 8H, $C_5H_4$), 6.90 (m, 8H, $C_5H_4$). $^{13}C$ $\{^1H\}$ MM ($CDCl_3$): $\delta_c$ −7.78 (s, $Si^4CH_3$), −6.43 (s, $Si^2CH_3$), −4.37 (s, $Si^3CH_3$), 2.90, 3.18, 4.47, 5.47, 6.00, 6.74 (s, $SiCH_2$), 108.92 (sg, $C_5H_4$, 113.68 (m, $C_5H_4$, 115.07 (s, $C_5H_4$), 127.77 (s, $C_5H_4$), 128.86 (s, $C_5H_4$). For the NMR analysis, Si are numbered from the core outward toward the periphery of the dendrimer and that number indicated by a superscript to the right of its chemical symbol.

Example 16

Preparation of Si[$CH_2CH_2SiMe_2CH_2CH_2SiMe_2 (C_5H_4)(C_5H_5)HfCl_2$]$_4$

A 20 mL Schlenk flask was charged with 1.103 g (2.38 mmol) of 5-dimethylvinylsilylcyclopentadienyl (cyclopentadienyl)hafnium dichloride, 224 mg (0.59 nmol) of Si($CH_2CH_2SiMe_2H$)$_4$, 2.5 mL of THF and 30 gL of the Karstedt catalyst. The reaction mixture was stirred at 50° C. for 12 h, and all volatiles were removed at reduced pressure. The residue was dissolved in 5 mL of toluene and filtered through Florisil™. After the toluene was removed, the remaining light brown, waxy compound was dried in vacuum at 50° C. and had melting point 73–76° C. and yield 1.21 g (91.29.-). Anal. Calcd. for $C72H_{116}Cl_8Si_9Hf_4$: C, 38.74; H, 5.24. Found: C, 38.83; H, 5.35. $^1H$ NMR ($CDCl_3$): $\delta$ −0.087 (s, 6H, $Si^2CH_3$), 0.23–0.60 (m, 14H, $Si^3CH_3$, $SiCH_2$), 6.337 (s, 5H, $C_5H4_5$), 6.436 (m, 2H, $C_5H_4$), 6.594 (m, 2H, $C_5H_4$). $^{13}C\ (^1H)$ NMR ($CDCl_3$): $\delta_c$ −4.37 (s, $Si^2CH_3$), −2.70 (s, $Si^3CH_3$), 2.66 (s, $Si^1\underline{C}H_2CH_2Si_2$), 6.59 S' $Si^2\underline{C}H_2CH_2Si^3$), 6.74 (s, $Si^1CH_2\underline{C}H_2Si^2$), 9.11 (s, $Si^2CH_2\underline{C}H_2Si^3$), 114.53 (s, $C_5H_5$), 115.87 (s, $C_5H_4$) 123.20 (s, $C_5H_4$), 124.19 (s, $C_5H_4$). $^{29}Si\ \{1H\}$ NMR ($CDCl_3$): $\delta$ −4.26 (s, $Si^3(C_5H_4)$, 5.00 (s' $\underline{Si}^2CH_2CH_2Si^3$), 8.60 (s, $\underline{Si}^2CH_2CH_2Si^3$). For the NMR analysis, Si atoms are numbered from the core outward toward the periphery of the dendrimer and that number indicated by a superscript to the right of its chemical symbol.

Example 17

Preparation of Si{$CH_2CH_2SiMe_2CH_2CH_2SiMe_2 (C_5H_4)(C_5H_5)ZrCl_2)_3$}$_4$

A 20 mL Schlenk flask was charged with 773 mg (2.05 mmol) of 5-dimethylvinylsilylcyclopentadienyl (cyclopentadienyl)zirconium dichloride, 222 mg (0.17 nimol) of Si($CH_2CH_2Si(CH_2CH_2SiMe_2H)3$)$_4$, 3 mL of THF and 80 $\mu$L of the Karstedt catalyst. The reaction mixture was stirred at 50° C. for 4 h. Toluene (5 mL) was added to the reaction mixture and the resulting solution was then filtered through Celite™. All volatiles were removed at reduced pressure. A light brown oil remained and was dried at 50° C. in high vacuum with yield 0.90 g (90%). Anal. Calcd. for $C_{224}H_{364}Cl_{24}Si_{29}Zr_{12}$: C, 46.25; H, 6.31. Found: C, 46.53; H, 6.11. $^1H$ NMR ($CDCl_3$): $\delta$ −0.113 (s, 18H, $Si^3CH_3$), 0.10–0.40 (m, s(overlapped), 42H, $Si^4CH_3$, $Si^2CH_2CH_2Si^3$, $Si^3CH_2CH_2Si^4$), 0.47–0.60 (m, 4H, $Si^1CH_2CH_2Si^2$), 6.44 (s, 15H, $C_5H_5$), 6.3 (m, 6 H, $C_5H_4$), 6.68 (m, 6H, $C_5H_4$). $^{13}C$ $\{^1H\}$ NMR ($CDCL_3$): $\delta_c$ −4.31 (S, $Si^3CH_3$), −2.78 (S, $Si^4CH3$), 2.34 (s(overlapped, broad), $Si^1CH_2$, $Si^2CH_2$), 6.33 (s, $Si^3\underline{C}H_2CH_2Si^4$), 6.77 (s, $Si^2CH_2\underline{C}H_2Si^3$), 8.91 (s, $Si^3CH_2\underline{C}H_2Si^4$), 115.83 (s, $C_5H_5$), 117.01 (s, $C_5H_4$), 125.16 (s, $C_5H_4$), 125.73 (s, $C_5H_4$). $^{29}Si\ \{1H\}$ NMR ($CDCl_3$): $\delta_{Si}$ −4.21 (S, $Si^4C_5H_5$), 4.95 (s, $Si^3$), 8.66 (s(overlapped), $Si^1$, $Si^2$). For the NMR analysis, Si atoms are numbered from the core outward toward the periphery of the dendrimer and that number indicated by a superscript to the right of its chemical symbol.

Example 18

Preparation of Si[$CH_2CH_2SiMe_2CH_2CH_2SiMe_2 (C_5H_4)(Me_3SiC_5H_4)RiCl_2$]$_4$ The following example is provided to demonstrate the coupling of a metallocene-containing compound with a Si—H bond and a dendrimer with vinyl groups at its termini to produce the desired metallocene-containing dendrimer.

A 20 mL Schlenk flask was charged with 532 mg (1.40 mmol) of 5-dimethylhydrogensilylcyclopentadienyl (trimethylsilylcyclopentadienyl)titanium dichloride, 168.0 mg (0.35 Tmnol) of Si($CH_2CH_2SiMe_2Vi$)$_4$, where Vi represents a vinyl functional group, 2.5 mL of THF and 70 $\mu$L of the Karstedt catalyst. The reaction mixture was stirred at 50° C. for 4 h, and volatiles were removed at reduced pressure. The red solid that remained was dried in high vacuum, as previously defined, at 60° C. and had a yield of approximately 70% in relation to the reacted vinyl groups of the dendrimer. $^1$H NMR (CDCl$_3$): δ 0.10–0.60 (m, s(overlapped), 20H, SiCH$_3$, SiCH$_2$), 5.60–6.20 (m, ~1H, CH=CH$_2$), 6.50–6.90 (m, 8H, C$_5$H$_4$). For the NMR analysis, Si, atoms are numbered from the core outward toward the periphery of the dendrimer and that number indicated by a superscript to the right of its chemical symbol.

The following Examples 19 and 20 describe preparation of dendrimers suitable for anchoring to a solid phase, such as a refractory oxide.

Example 19

Preparation of Si(CH$_2$CH$_2$SiMe$_2$)$_4$(CH$_2$CH$_2$SiMe$_2$ (C$_5$H4)(C$_5$H$_5$)TiCl$_2$)$_{2.5}$(CH$_2$CH$_2$Si(OMe)$_3$)$_{1.5}$ A 20 mL Schlenk flask was charged with 714 mg (2.14 mmol) of 5-dimethylvinylsilylcyclopentadienyl (cyclopentadienyl)titanium dichloride, 323 mg (0.86 mmol) of Si(CH$_2$CH$_2$SiMe$_2$H)$_4$, 3 mL of THF and 60 gL of the Karstedt catalyst. The reaction mixture was stirred at 40° C. for 0.5 h. and 190 mg (1.285 mmol) of vinyltrimethoxysilane was added to the reaction mixture. The resulting reaction mixture was then stirred at 40° C. for 8 h. All volatiles were removed at reduced pressure. A red, waxy compound remained and had yield 1.22 g (approximately 100%). 15 Anal. Calcd. for C$_{58.5}$H$_{107}$Cl$_{504.5}$Si$_9$Ti$_{2.5}$: C, 49.06; H, 7.53. Found: C, 48.51; H, 7.28. $^1$H NMR (CDCl$_3$): δ −0.10−−0.07 (s(overlapped), 24H, Si$^2$CH$_3$), 0.22–0.63 (m, 47H, Si$^{3.1}$CH$_3$, SiCH$_2$,), 3.552 (s, 13.5H, OCH$_3$), 6.530 (s, 12.5H, C$_5$H$_5$), 6.600 (m, 5H, C$_5$H$_4$), 6.838 (m, 5H, C$_5$H$_4$). $^{13}$C {$^1$H} NMR (CDCl$_3$): δ$_c$ −4.73 (Sg, Si$^2$CH$_3$), −2.90 (Sg, Si$^3$CH$_3$), 0.98 (s, Si$^2$CH$_2$CH$_2$Si(OMe)$_3$), 2.28 (s, Si$^1$CH$_2$CH$_2$Si$^2$), 5.19 (s, Si$^2$CH$_2$CH$_2$Si(OMe)$_3$), 6.33 (sg, Si$^1$CH$_2$CH$_2$Si$^2$, Si$^2$CH$_2$CH$_2$SiC$_5$H$_5$), 8.67 (s, Si$^2$CH$_2$CH$_2$SiC$_5$H$_5$), 50.5 (sg, OCH$_3$), 120.3 (sg, C$_5$H$_4$,C$_5$H$_5$), 128.8–131.8 (sg, C$_5$H$_4$), where "sg" denotes a group of signals and "Me" denotes a methyl group. For the NMR analysis, Si atoms are numbered from the core outward toward the periphery of the dendrimer and that number indicated by a superscript to the right of its chemical symbol.

Example 20

Preparation of Si(CH$_2$CH$_2$SiMe$_2$)$_4$(CH$_2$CH$_2$SiMe$_2$ (C$_5$H$_4$)(C$_5$H$_5$)ZrCl$_2$)$_{2.5}$(CH$_2$CH$_2$Si(OMe)$_3$)$_{1.5}$ A 20 mL Schienk flask was charged with 542 mg (1.44 mmol) of 5-dimethylvinylsilylcyclopentadienyl (cyclopentadienyl)zirconium dichloride, 217 mg (0.58 nunol) of Si(CH$_2$CH$_2$SiMe$_2$H)$_4$, 2 mL of THF and 60 μL of the Karstedt catalyst. The reaction mixture was stirred at 40° C. for 0.5 h. and then 128 mg (0.86 mmol) of vinyltrimethoxysilane was added to the mixture. The resulting reaction mixture was stirred at 40° C. for 8 h. All volatiles were removed at reduced pressure. The residue was dissolved in methylene chloride and filtered through silica gel. After all volatiles were removed, a light brown, waxy compound remained. A yield of 842 mg (95%) was obtained. Anal. $^1$H NMR (CDCl$_3$): δ 0.10–0.10 (s (overlapped), 24H, Si$^2$CH$_3$), 0.22–0.63 (m, 47H, Si$^{3.1}$CH$_3$, SiCH$_2$), 3.56 (s, 13.5H, OCH$_3$), 6.43 (s, 12.5H, C$^5$H$_5$), 6.52 (m, 5H, C$_5$H$_4$), 6.68 (m, 5H, C$_5$H$_4$). For the NMR analysis, Si atoms are numbered from the core outward toward the periphery of the dendrimer and that number indicated by a superscript to the right of its chemical symbol.

The following Examples 21 and 22 demonstrate the use of dendrimers with Group 4 metallocene termini as catalysts.

Example 21

Polymerization of Phenylsilane Induced by Si [CH$_2$CH$_2$SiMe$_2$CH$_2$CH$_2$SiMe$_2$(C$_5$H$_4$)(C$_5$H$_5$)ZrCl$_2$]$_4$ A 25 mL Schlenk flask equipped with a rubber septum was charged with a stir bar, 127 mg (67.4 mmol) of Si(CH$_2$CH$_2$SiMe$_2$CH$_2$CH$_2$SiMe$_2$(C$_5$H$_4$)(C$_5$H$_4$)ZrCl$_2$]$_4$ and 4 mL of toluene. The mixture was cooled to −10° C. and 0.21 mL (0.53 mmol) of a 2.5 m solution of n-butyllithium in hexane was injected by syringe. After stirring for 5 min at 0° C., 2.0 g (18.5 mmol) of phenylsilane, PhSiH$_3$, was injected into the flask, forming a light yellow, clear solution. Vigorous bubbling occurred immediately upon introduction of the phenylsilane. After removal of the ice bath, and within 15 min of being exposed to room temperature, the reaction mixture became red. After stirring for 1 h at room temperature, 4 mL of n-hexane was added and the reaction mixture was filtered through Celite™. Then, all volatiles were removed at reduced pressure leaving a yellow, waxy compound that was dried in vacuum with yield 1.820 g (91.6%). Spectroscopic evidence, including NMR and infrared (IR) spectroscopic data, showed the compound to be a poly(phenylsilane). Anal. Calcd. for H(PhSiH)$_x$H: C, 67.8; H, 5.7. Found: C, 67.2; H, 5.8. $^1$H NMR (CD$_2$Cl$_2$): δ 3.65–5.10 (m (broad), 1H, SiH), 6.50–7.50 (m (broad), 5.8H, C$_6$H$_5$). IR 3065 cm$^{-1}$ (C—H), 2106 cm$^{-1}$ (Si—H).

Example 22

Polymerization of Phenylsilane Induced by Si [CH$_2$CH$_2$SiMe(CH$_2$CH$_2$SiMe$_2$(C$_5$H$_4$)(CH$_5$H$_5$) ZrCl$_2$)$_2$]$_4$ A 25 mL Schlenk flask equipped with a rubber septum was charged with a stir bar, 146 mg (36.3 μmol) of Si[CH$_2$CH$_2$SiMe (CH,CH$_2$SiMe$_2$CH$_2$CH$_2$SiMe$_2$(C$_5$H$_4$)(C$_5$H$_5$)ZrCl$_2$)$_2$]$_4$ and 4 mL of toluene. The mixture was cooled to −10° C. and 0.23 mL (0.57 mmol) of a 2.5 m solution of n-butyllithium in hexane was injected by syringe. After stirring for 7 min at −10° C., 2.1 g (19.4 mmol) of phenylsilane, was injected into the flask, forming a light yellow, clear solution. Vigorous bubbling occurred immediately upon introduction of the phenylsilane. After 10 min, the ice bath was removed, and within 10 min of being exposed to room temperature, the reaction mixture became red. After stirring for 50 min at room temperature, 4 mL of n-hexane was added and the reaction mixture was filtered through Celite™. Then, all volatiles were removed at reduced pressure leaving an orange, waxy compound that was dried in vacuum with yield 1.95 g (95%). Spectroscopic evidence, including NMR and infrared (IR) spectroscopic data, showed the 20 compound to be a poly(phenylsilane). Anal. Calcd. for H(PhSiH)$_x$H: C, 67.8; H, 5.7. Found: C, 67.7; H, 5.8. $^1$H NMR ((CD$_3$)$_2$CO): δ 3.70–5.30 (m (broad), 1H, SiH), 6.60–7.85 (m (broad), 5.2H, C$_6$H$_5$). IR 3065 cm$^{-1}$ (C—H), 2106 cm$^{-1}$ (Si—H)

The following Examples 23–27 are provided to demonstrate the use of the catalysts of the invention for catalysis of olefin polymerization.

Example 23

Homopolymerization of Ethylene

A 250 ml four-necked flask equipped with reflux condenser, magnetic stir bar, inside thermometer, nitrogen inlet/outlet and a gas inlet tube was filled with 100 ml toluene, 0.66 ml MAO solution (10% by weight in toluene)

and 0.5 ml of a 0.002 M solution of (Si[CH$_2$CH$_2$SiMe$_2$CH$_2$CH$_2$SiMe$_2$C$_5$H$_4$(C$_5$H$_5$)ZrCl$_2$]$_4$), described in Example 10, in toluene. This solution was stirred for 20 minutes to activate the catalyst The catalyst solution was then heated to 40° C. and held at this temperature. Ethylene was bubbled through the system for 15 minutes. The reaction was stopped by addition of a 50 ml methanol solution containing 0.5 ml 1 N HCl. The polymer was then filtered and washed several times with methanol. Finally, the polymer was dried in vacuum at 50° C. for 20 hours yielding 1.44 g polyethylene, which translates to a catalyst activity of 5760 kg/mol-hour.

Example 24

Copolymerization of Ethylene with Prolpylene

The polymerization was done as described for Example 23 using 5 ml of 0.002 M solution of (Si[CH$_2$CH$_2$SiMe$_2$CH$_2$CH$_2$SiMe$_2$C$_5$H$_4$(C$_5$H$_5$)ZrCl$_2$]$_4$), described in Example 10, and bubbling a mixture of ethylene/propylene (1:1 by volume), through the system. The polymerization was done at 20° C. for 60 minutes providing 14.6 g of a sticky copolymer, which translates to a catalyst activity of 1460 kg/mol-hour.

Example 25

Homopolymerization of Cyclopentene

A 250 ml two-necked flask equipped with septa, magnetic stir bar, nitrogen inlet and outlet was filled in an inert atmosphere box with 6.5 mg of (Si{CH$_2$CH$_2$SiMe$_2$CH$_2$CH$_2$SiMe(C$_5$H$_4$)$_2$ZrCl$_2$]$_4$), described in Example 14. The catalyst was then dissolved in −20 ml MAO solution. The flask was transferred out of the inert atmosphere box and the homogeneous solution was stirred for 0.5 hours to activate the catalyst.

In a separate Schlenk tube, which was flame dried under nitrogen flow, 30 ml cyclopentene and 10 ml MAO solution were mixed. This solution was transferred in an air tight syringe to the preactivated catalyst/cocatalyst solution. The thus-obtained solution was then stirred for 24 hours at 25° C. After this time period, a solution of 50 ml ethanol containing 20% 1 N HCl was carefully added. The solution was then stirred for 5 hours to remove cocatalyst residues. The white polymer was filtered and washed several times with methanol and then acetone. The polymer was then dried for 24 hours in a vacuum oven at 80° C., yielding 2.5 g of a white crystalline polymer which is insoluble in common solvents at room temperature. The catalyst activity is 29 kg/mol-hour. Differential scanning calorimetry (DSC) shows no melting point before decomposition of the material.

Example 26

Homopolymerization of 1-Hexene

A 250 ml two-necked flask equipped with septa, magnetic stir bar, nitrogen inlet and outlet was filled in an inert atmosphere box with 4.0 mg of (Si[CH$_2$CH$_2$SiMe$_2$CH$_2$CH$_2$SiMe(C$_3$H$_4$)$_2$ZrCl$_2$]$_4$), described in Example 14. The catalyst was then dissolved in −20 ml MAO solution. The flask was transferred out of the inert atmosphere box and the homogeneous solution was stirred for 0.5 hours to activate the catalyst.

In a separate Schlenk-tube, which was flame dried under nitrogen flow, 20 ml 1-hexene and 10 ml MAO solution were mixed. This solution was transferred in an air tight syringe to the preactivated catalyst/cocatalyst solution. The obtained solution was then stirred for 7 days at 25° C. The polymerization was stopped by addition of 50 ml of ethanol. The obtained cocatalyst residues were filtered. The remaining solution was concentrated at the rotavap leading to a clear, low viscosity, atactic polyhexene, which was dried in vacuum at 60° C. for 24 hours. The yield was 4.1 g, which translates 20 to a catalyst activity of 11 kg/mol-hour.

Example 27

Copolymerization of 1-Hexene with Cyclopentene

A 250 ml two-necked flask equipped with septa, magnetic stir bar, and nitrogen inlet and outlet was filled in an inert atmosphere box with 4.0 mg of (Si(CH$_2$CH$_2$SiMe$_2$CH$_2$CH$_2$SiMe(C$_5$H$_5$)$_2$ZrCl$_2$]$_4$), described in Example 14. The catalyst was then dissolved in 20 ml MAO solution. The flask was transferred out of the inert atmosphere box and the homogeneous solution was stirred for 0.5 hours to activate the catalyst.

In a separate Schlenk-tube, which was flame dried under nitrogen flow, 10 ml 1-hexene, 10 ml cyclopentene and 10 ml MAO solution were mixed. This solution was transferred in an air tight syringe to the preactivated catalyst/cocatalyst solution. The thus-obtained solution was then stirred for 4 days at 25° C. After this time period, a solution of 50 ml ethanol containing 20% 1 N HCl was carefully added and stirred for 5 hours to remove cocatalyst residues. The polymer was filtered and washed several times with methanol and acetone. The polymer was then dried for 24 hours in a vacuum oven at 80° C., yielding 3.2 g of a white, wax-type polymer, which translates to a catalyst activity of 15 kg/mol-hour.

Example 28

The following example describes preparation of a cascade dendrimer from (CH$_2$=CH)$_2$MeSiH in THF at low concentration.

Into a 10 mL flask equipped with a stir bar and rubber septum was added 372 mg (3.79 mmol) of (CH$_2$=CH)$_2$MeSiH and 3 mL of THF. Then, 1 drop of the Karstedt catalyst was added. The resulting mixture was stirred at room temperature for 24 hours. The volatiles were removed at reduced pressure at room temperature. A colorless oil remained. A yield of 371 mg, approximately 100%, was obtained. Anal. Calcd. for (C$_5$H$_{10}$Si)$_n$: C, 61.14; H, 10.26. Found: C, 60.91; H, 10.23. $^1$H NMR (C$_6$D$_6$): δ −0.05–0.45 (s(overlapped), 3H, SiCH$_3$) 0.50–1.28 (m, 4H, SiCH$_2$), 5.60–6.40 (m, 3H, CH=CH$_2$).

Example 29

The following example describes preparation of a cascade dendrimer from (CH$_2$=CH)$_2$MeSiH in THF at high concentration.

Into a 10 mL flask equipped with a stir bar and rubber septum was added 375 mg (3.82 mmol) of (CH$_2$=CH)$_2$MeSiH and 0.5 mL of THF. Then, 1 drop of the Karstedt catalyst was added. The reaction started spontaneously and the temperature increased to approximately 50° C. The resulting mixture was kept at approximately 50° C. and stirred for 2 hours. The volatiles were removed at reduced pressure at room temperature. A colorless oil remained. A yield of 375 mg, approximately 100%, was obtained. Anal. Calcd. for (C$_5$H$_{10}$Si)$_n$: C, 61.14; H, 10.26. Found: C, 60.95; H, 10.25. $^1$H NMR (C$_6$D$_6$): δ −0.05–0.35 (s(overlapped), 3H, SiC$\underline{H}_3$), 0.50–1.28 (m, 4H, SiC$\underline{H}_2$), 5.63–6.40 (m, 3H, CH=CH$_2$). Molecular Weight (VPO in benzene): M=738 g/mol.

Example 30

The following example describes preparation of a cascade dendrimer from (CH$_2$=CH)$_2$MeSiH in Et$_2$O.

Into a 10 mL flask equipped with a stir bar and rubber septum was added 750 mg (7.64 mmol) of (CH$_2$=CH)$_2$MeSiH and 0.5 mL of ether. This mixture was stirred in a bath at room temperature. Then, 1 drop of the Karstedt catalyst was added. An exothermic reaction started. The mixture was stirred at 35° C. for 2 hours. The volatiles were removed at reduced pressure at room temperature. A colorless oil remained. A yield of 749 mg, approximately 100%, was obtained. Anal. Calcd. for (C$_5$H$_{10}$Si)$_n$: C, 61.14; H, 10.26. Found: C, 60.97; H, 10.28. $^1$H NMR (C$_6$D$_6$): δ −0.5–0.40 (s(overlapped), 3H, SiC$\underline{H}_3$), 0.45–1.28 (m, 4H, SiC$\underline{H}_2$), 5.63–6.40 (m, 3H, CH=CH$_2$). Molecular Weight (calculated from VPO obtained in Example 5): M=558 g/mol.

Example 31

The following example describes stepwise growth of a cascade dendrimer from (CH$_2$=CH)$_2$MeSiH in Et$_2$O including steps 31A, 31B, and 31C.

Step 31A

Into a 10 mL flask equipped with a stir bar and rubber septum was added 750 mg (7.64 mmol) of (CH$_2$=CH)$_2$MeSiH and 0.5 mL of ether. This mixture was stirred in a bath at room temperature. Then, 1 drop of the Karstedt catalyst was added. An exothermic reaction started. The mixture was stirred at 35° C. for 4 hours. The ether was removed at reduced pressure at room temperature. A colorless oil ("Product 31A") remained. A yield of 750 mg, approximately 100%, was obtained. $^1$H NMR (C$_6$D$_6$): δ −0.05–0.45 (s(overlapped), 3H, SiC$\underline{HH}_3$), 0.50–1.25 (m, 4H, SiC$\underline{H}_2$), 5.63–6.38 (m, 3H, CH=CH$_2$). Molecular Weight (VPO in toluene): M=526 g/mol.

Step 31B

Into a 10 mL flask equipped with a stir bar and rubber septum was added 500 mg of Product 31A dendrimer prepared in the foregoing Step 31A. This mixture was stirred in a bath at 40° C. One drop of the Karstedt catalyst was added and, then, over a 4 hour period, was added 500 mg (5.09 mmol) of (CH$_2$=CH)$_2$MeSiH by syringe. The reaction mixture turned light yellow. This mixture was kept at 50° C. for another 2 hours. The volatiles were removed at reduced pressure at room temperature. A colorless, viscous oil ("Product 4B") remained. A yield of 1.0 g, approximately 100%, was obtained. Anal. Calcd. for (C$_5$H$_{10}$Si)$_n$: C, 61.14; H, 10.26. Found: C, 61.61; H, 10.45. $^1$H NMR (C$_6$D$_6$): δ −0.05–0.45 (s(overlapped), 3H, SiC$\underline{H}_3$), 0.50–1.30 (m, 4H, SiC$\underline{H}_2$), 5.63–6.42 (m, 3H, CH=CH$_2$) Molecular Weight (VPO in toluene): M=831 g/mol.

Step 31C

Using the same procedure and reagent quantities as described above in Step 31B, but substituting Product 31B for Product 31A, a third reaction was carried out. A colorless oil, ("Product 31C"), more viscous than Product 31B remained. A yield of 1.0 g, approximately 100%, was obtained. Anal. Calcd. for (C$_5$H$_{10}$Si)$_n$: C, 61.14; H, 10.26. Found: C, 61.56; H, 10.28. $^1$H NMR (C$_6$D$_6$): δ −0.05–0.45 (s(overlapped), 3H, SiC$\underline{H}_3$), 0.50–1.35 (m, 4H, SiC$\underline{H}_2$), 5.62–6.42 (m, 3H, CH=CH$_2$). $^{13}$C NMR {$^1$H}, (CDCl$_3$): δ −7.00 to −3.00 (SiCH$_3$), 1.0–11.0 (SiCH$_2$), 131.0–133 (SiCH=$\underline{C}$H$_2$), 136.0–140 (Si$\underline{C}$H=CH$_2$). $^{29}$Si NMR {$^1$H}, (CDCl$_3$): δ$_{Si}$ −11.4 to −10.3 (Si(CH=CH$_2$)$_2$), −1.70–0.70 (SiCH=$\underline{C}$H$_2$) 7.80–8.70 (SiCH$_2$CH$_2$Si) Molecular Weight (VPO in toluene): M=886 g/mol.

Example 32

The following example describes preparation of a cascade dendrimer from (CH$_2$=CH)$_3$SiH in Et$_2$O.

Into a 10 mL flask equipped with a stir bar and rubber septum was added 1 mL of ether and 1 drop of the Karstedt catalyst. This mixture was stirred in a bath at 35° C. Then, over a 5 minute period 722 mg (7.00 mmol) of (CH$_2$=CH)$_3$SiH was added slowly by syringe. The mixture was stirred at 35° C. for 6 hours. The volatiles were removed at reduced pressure at room temperature. A colorless, somewhat viscous oil remained. A yield of 770 mg, approximately 100%, was obtained. Anal. Calcd. for (C$_6$H$_{10}$Si)$_n$: C, 65.38; H, 9.14. Found: C, 65.30; H, 9.24. $^1$H NMR (C$_6$D$_6$): δ −0.10–1.40 (m, approx. 2.7H, SiC$\underline{H}_2$), 5.67–6.50 (m, 3H, CH=CH$_2$). $^{13}$C NMR {$^1$H}, (CDCl$_3$): δ$_c$ −1.0–10.5 (SiCH$_3$), 132.0–137.5 (SiCH=CH$_2$). $^{29}$Si NMR {$^1$H}, (CDCl$_3$): δ$_{Si}$ −18.3 to −14.9 (Si(CH=CH$_2$)$_3$), −9.1 to −3.7 (Si(CH=CH$_2$)$_2$), 0.4–5.0 (SiCH=CH$_2$), 10.3–11.4 (SiCH$_2$) Molecular Weight (VPO in toluene): M=531 g/mol.

Example 33

The following example describes preparation of a cascade dendrimer from (CH$_2$=CHCH$_2$)$_2$MeSiH in Et$_2$O.

Into a 10 mL flask equipped with a stir bar and rubber septum was added 813 mg (6.44 mmol) of (CH$_2$=CHCH$_2$)$_2$MeSiH and 0.5 mL of ether. This mixture was stirred at room temperature. Then, 1 drop of the Karstedt catalyst was added. The reaction started spontaneously and the temperature increased. The mixture was stirred at 35° C. for 3 hours. The volatiles were removed at reduced pressure at room temperature. A colorless, highly viscous oil remained. A yield of 812 mg, approximately 100%, was obtained. Anal. Calcd. for (C$_7$H$_{14}$Si)$_n$: C, 66.58; H, 11.18. Found: C, 66.52; H, 11.12. $^1$H NMR(C$_6$D$_6$): δ0.00–0.30 (s(overlapped), 3H, SiC$\underline{H}_3$), 0.60–0.93 (m, 4H, SiC$\underline{H}_2$CH$_2$C$\underline{H}$hd 2Si), 1.38–1.85 (m, 4H, SiC$\underline{H}_2$CH=CH$_2$, SiCH$_2$C$\underline{H}_2$C$\underline{H}_2$Si), 4.90–5.13 (m, 2H, CH$_2$CH=CH$_2$), 5.70–6.02 (m, 1H, CH$_2$C$\underline{H}$=CH$_2$). $^{13}$C NMR {$^1$H}, (CDCl$_3$): δ$_c$ −6.00 to −4.50 (SiCH$_3$), 17.5–19.5 (SiCH$_2$), 21.0–23.0 (SiCH$_2$$\underline{C}$H$_2$CH$_2$Si), 113.0 (SiCH$_2$CH=$\underline{C}$H$_2$), 134.0 (SiCH$_2$$\underline{C}$H=CH$_2$). $^{29}$Si NMR {$^1$H}, (CDCl$_3$): δ$_{Si}$ −1.0–1.5 (SiCH$_2$CH$_2$, SiCH$_2$CH=CH$_2$). Molecular Weight (VPO in benzene): M=3668 g/mol.

Example 34

The following example describes preparation of a cascade dendrimer from (CH$_2$=CHCH$_2$)$_3$SiH in Et$_2$O.

Into a 10 mL flask equipped with a stir bar and rubber septum was added 1 mL of ether and 1 drop of the Karstedt catalyst. This mixture was stirred in a bath at 35° C. Then, over a 5 minute period 841 mg (5.52 mmol) of (CH$_2$=CHCH$_2$)$_3$SiH was added slowly by syringe. The mixture was stirred at 35° C. for 6 hours. The volatiles were removed at reduced pressure at room temperature. A light yellow, viscous oil remained. A yield of 840 mg, approximately 100%, was obtained. Anal. Calcd. for (C$_9$H$_{16}$Si)$_n$: C, 70.97; H, 10.59. Found: C, 71.49; H, 10.98. $^1$H NMR (C$_6$D$_6$): δ 0.65–1.20 (m, 2H, SiC$\underline{H}_2$), 1.40–2.00 (m, approx. 3.5H, SiCH$_2$C$\underline{H}_2$CH$_2$Si, SiC$\underline{H}_2$CH=CH$_2$), 4.90–5.28 (m, 2H, CH$_2$CH=C$\underline{H}_2$), 5.65–6.28 (m, 1H, CH$_2$C$\underline{H}$=CH$_2$).

$^{13}$C NMR {$^1$H}, (CDCl$_3$): δ$_c$ 16.0–19.0 (SiCH$_2$CH$_2$CH$_2$Si), 19.0–21.0 (SiCH$_2$CH=CH$_2$), 112.5–114.0 (SiCH$_2$CH=CH$_2$), 134.0–136.5 (SiCH$_2$CH=CH$_2$). $^{29}$Si NMR {$^1$H}, (CDCl$_3$): δ$_{Si}$ –2.0–1.0 (SiCH$_2$), –9.0 to –10.5 (SiH (weak)). Molecular Weight (VPO in benzene): M=2460 g/mol.

Example 35

The following example describes stepwise growth of a cascade dendrimer from (CH$_2$=CHCH$_2$)$_3$SiH in Et$_2$O including steps 35A, 35B, and 35C.

Step 35A

Into a 10 mL flask equipped with a stir bar and rubber septum was added 1.0 mL of ether and 1 drop of the Karstedt catalyst. Then, over a 5 minute period, was added 0.84 g (5.52 mmol) of (CH$_2$=CHCH$_2$)$_3$SiH by syringe. This mixture was stirred at 45° C. for 6 hours. The ether was removed at reduced pressure at room temperature. A light yellow, viscous oil ("Product 35A") remained. A yield of 839 mg, approximately 100%, was obtained. $^1$H NMR (C$_6$D$_6$): δ 0.55–1.20 (m, 2H, SiCH$_2$), 1.30–2.00 (m, approx. 3.5H, SiCH$_2$CH$_2$CH$_2$Si, SiCH$_2$CH=CH$_2$), 4.85–5.25 (m, 2H, CH$_2$CH=CH$_2$), 5.60–6.25 (m, 1H, CH$_2$CH=CH$_2$). $^{13}$C NMR {$^1$H}, (C$_6$D$_6$): δ $_c$16.5–19.5 (SiCH$_2$CH$_2$CH$_2$Si), 19.5–21.5 (SiCH$_2$CH=CH$_2$), 113.0–114.5 (SiCH$_2$CH=CH$_2$), 134.5–136.0 (SiCH$_2$CH=CH$_2$). $^{29}$Si NMR {$^1$H}, (C$_6$D$_6$): δ$_{Si}$ –2.5–1.0 (SiCH$_2$), –9.0 to –10.5 (SiH (weak)). Molecular Weight (VPO in toluene): M=2555 g/mol.

Step 35B

Into a 10 mL flask equipped with a stir bar and rubber septum was added 504 mg of Product 8A dendrimer prepared in the foregoing Step 8A and 0.2 mL of ether. This mixture was stirred in a bath at 45° C. One drop of the Karstedt catalyst was added and, then, over a 1 hour period, was added 0.84 g (5.52 mmol) of (CH$_2$=CHCH$_2$)$_3$SiH by syringe. This mixture was kept at 45° C. for another 6 hours. The volatiles were removed at reduced pressure at room temperature. A light yellow oil, ("Product 35B"), more viscous than Product 35A, remained. A yield of 1.34 g, approximately 100%, was obtained. Anal. Calcd. for (C$_9$H$_{16}$Si)$_n$: C, 70.97; H, 10.59. Found: C, 71.75; H, 10.86. $^1$H NMR (C$_6$D$_6$): δ 0.55–1.20 (m, 2.3H, SiCH$_2$), 1.30–2.05 (m, approx. 3.7H, SiCH$_2$CH$_2$CH$_2$Si, SiCH$_2$CH=CH$_2$), 4.85–5.30 (m, 2H, CH$_2$CH=CH$_2$), 5.60–6.30 (m, 1H, CH$_2$CH=CH$_2$). $^{13}$C NMR {$^1$H}, (C$_6$D$_6$): δ$_c$ 16.5–19.5 (SiCH$_2$CH$_2$CH$_2$Si), 19.5–21.5 (SiCH$_2$CH=CH$_2$), 113.0–114.5 (SiCH$_2$CH=CH$_2$), 134.5–136.0 (SiCH$_2$CH=CH$_2$). $^{29}$Si NMR {$^1$H}, (C$_6$D$_6$): δ$_{Si}$ –2.5–1.0 (SiCH$_2$), –7.5 to –10.5 (SiH (weak)). Molecular Weight (VPO in toluene): M=5445 g/mol.

Step 35C

Into a 10 mL flask equipped with a stir bar and rubber septum was added 513 mg of Product 35B dendrimer prepared in the foregoing Step 35B and 0.5 mL of ether. This mixture was stirred in a bath at 45° C. One drop of the Karstedt catalyst was added and, then, over a 1 hour period, was added 0.42 g (2.76 mmol) of (CH$_2$=CHCH$_2$)$_3$SiH by syringe. This mixture was kept at 45° C. for another 6 hours. The volatiles were removed at reduced pressure at 50° C. A light brown, soluble gel ("Product 35C") remained. A yield of 0.93 g, approximately 100%, was obtained. $^1$H NMR (C$_6$D$_6$): δ 0.50–1.25 (m, approx. 2.0H, SiCH$_2$), 1.30–2.05 (m, approx. 3.5H, SiCH$_2$CH$_2$CH$_2$Si, SiCH$_2$CH=CH$_2$), 4.85–5.30 (m, 2H, CH$_2$CH=CH$_2$), 5.60–6.40 (m, 1H, CH$_2$CH=CH$_2$). Molecular Weight could not be obtained because the product was not sufficiently soluble.

Example 36

The following example describes quenching of the cascade dendrimer from (CH$_2$=CHCH$_2$)$_2$MeSiH with Me$_3$SiCH=CH$_2$. The two experiments described below were carried out to demonstrate deactivation of remaining Si—H bonds in the dendrimer.

Synthesis 36A—30 Minute Dendrimer Synthesis

Into a 10 mL flask equipped with a stir bar and rubber septum was added 1.22 g (9.66 mmol) of (CH$_2$=CHCH$_2$)$_2$MeSiH, 1.0 mL of ether, and 1 drop of the Karstedt catalyst. This mixture was stirred at 35° C. for 30 minutes. Then, 0.2 mL of Me$_3$SiCH=CH$_2$ was added by syringe. The reaction mixture was stirred for another 2.5 hours. The volatiles were removed at reduced pressure at 50° C. A light yellow, viscous oil, ("Product 36A"), remained. A yield of 1.25 g, approximately 98%, was obtained. $^1$H NMR (C$_6$D$_6$): δ –0.05–0.30 (m, 3.5H, SiCH$_3$, Si(CH$_3$)$_3$), 0.35–1.00 (m, approx. 4.1H, SiCH$_2$SiCH$_2$CH$_2$Si, SiCH$_2$CH$_2$Si), 1.35–1.90 (m, approx. 4.1H, SiCH$_2$CH=CH$_2$, SiCH$_2$CH$_2$CH$_2$Si) 4.85–5.14 (m, 2H, CH$_2$CH=CH$_2$), 5.70–6.20 (m, 1H, CH$_2$CH=CH$_2$).

Synthesis 36B—2 Hour Dendrimer Synthesis

Into a 10 mL flask equipped with a stir bar and rubber septum was added 1.20 g (9.66 mmol) of (CH$_2$=CHCH$_2$)$_2$MeSiH, 1.0 mL of ether, and 1 drop of the Karstedt catalyst. This mixture was stirred at 35° C. for 2 hours. Then, 0.2 mL of Me$_3$SiCH=CH$_2$ was added by syringe. The reaction mixture was stirred for another hour. The volatiles were removed at reduced pressure at 50° C. A light yellow oil, more viscous than Product 36A, remained. A yield of 1.22 g, approximately 98%, was obtained. $^1$H NMR (C$_6$D$_6$): δ 0.05–0.35 (m, 3.3H, SiCH$_3$, Si(CH$_3$)$_3$, 0.45–1.10 (m, approx. 4.2H, SiCH$_2$SiCH$_2$CH$_2$Si, SiCH$_2$CH$_2$Si), 1.35–1.88 (m, approx. 4.25H, SiCH$_2$CH=CH$_2$, SiCH$_2$CH$_2$CH$_2$Si), 4.85–5.13 (m, 2H, CH$_2$CH=CH$_2$), 5.65–6.20 (m, 1H, CH$_2$CH=CH$_2$).

Example 37

The following example describes chemical conversions of a cascade dendrimer prepared from (CH$_2$=CH)$_2$MeSiH.

Conversion 37A

Into a 10 mL flask equipped with a stir bar and rubber septum was added 740 mg of a dendrimer prepared from (CH$_2$=CH)$_2$MeSiH as described in the foregoing Example 3 and 0.5 mL of ether. This mixture was stirred in a bath at room temperature. Then, 0.5 mL (434 mg, 4.59 mmol) of HSiMe$_2$Cl was added. The reaction started spontaneously and the temperature increased. The mixture was stirred at 35° C. for 2 hours. The volatiles were removed at reduced pressure at 50° C. A colorless, viscous oil ("Product 37A") remained. A yield of 1.0 g, approximately 100%, was obtained. $^1$H NMR (CDCl$_3$): δ 0.20–0.02 (s(overlapped), 2.7H, SiCH$_3$), 0.38 (s, 6H, SiCH$_3$Cl), 0.44–1.14 (m, 5.6H, SiCH$_2$).

Conversion 37B–Reduction of Product 10A

Into a 20 mL flask equipped with a stir bar and rubber septum was added 1.0 g of a chlorosilyl group containing Product 37A dendrimer prepared in the foregoing Conversion 37A and 2 mL of ether. This mixture was stirred in a bath at room temperature. Then, 100 mg (2.63 mmol) of LiAlH$_4$, in 3 mL of ether was added slowly by syringe. An exothermic reaction occurred. The mixture was stirred at 35° C. for 2 hours. Then, the reaction mixture was hydrolyzed with 5 mL of 0.5 M HCl. The solution was filtered through Celite™ (Celite 545™), a diatomaceous earth purchased from Fisher Scientific Co., and washed twice with 3 mL of ether. The organic layer was washed with water and separated. After the solution was dried over MgSO$_4$, all volatiles were removed at reduced pressure at 50° C. A colorless, viscous oil remained. A yield of 850 mg, approximately 94.4%, was obtained. Anal. Calcd. for $(C_7H_{18}Si_2)_n$: C, 53.08; H, 11.45. Found: C, 53.60; H, 11.36. $^1$H NMR (CDCl$_3$): δ 0.00–0.35 (s(overlapped), 9.7H, SiC$\underline{H}_3$), 0.48–1.35 (m, 8.7H, SiC$\underline{H}_2$), 4.10–4.27 (m, 1H, Si$\underline{H}$). Molecular Weight (VPO in benzene): M=905 g/mol.

Synthesis 37C—Preparation of a Dichlorozirconocene complex [—MeSi(CH$_2$CH$_2$—)(CH$_2$CH$_2$SiMe$_2$CH$_2$CH$_2$SiMe$_2$C$_5$H$_4$](C$_5$H$_5$)ZrCl$_2$]$_n$ approximately 6)

Into a 20 mL flask equipped with a stir bar and rubber septum was added 244 mg (0.65 mmol) of [(CH$_2$=CH)Me$_2$SiC$_5$H$_4$] (C$_5$H$_5$)ZrCl$_2$, 102 mg (approximately 0.65 mmol) of a Si—H group-containing dendrimer prepared in Conversion 10B, 0.5 mL of THF and 1 drop of the Karstedt catalyst solution. This mixture was stirred at 50° C. for 6 hours. Then, all volatiles were removed at reduced pressure, and the residue was washed twice with 1 mL of hexane. The light brown, waxy product was dried in vacuum at 40° C. A yield of 330 mg, 95.4%, was obtained. Anal. Calcd. for $(C_{21}H_{36}Cl_2Si_3Zr)_n$: C, 47.15; H, 6.78. Found: C, 48.26; H, 6.78. $^1$H NMR (CDCl$_3$): δ −0.15–0.15 (s(overlapped), 11H, SiC$\underline{H}_3$), 0.31 (s, 6H, CpSiC$\underline{H}_3$), 0.32–1.10 (m, approx. 12H, SiC$\underline{H}_2$), 6.46 (s, 5H, C$_5$H$_5$), 6.57 (m, 2H, C$_5$H$_4$), 6.73 (m, 2H, C$_5$H$_4$). $^{13}$C NMR {$^1$H}, (CD$_2$Cl$_2$): δ$_c$ −7.0–0.0 (SiCH$_3$), 4.0–10.0 (SiCH$_2$), 116.3 (C$_5$H$_5$), 117.7 (C$_5$H$_4$), 125.7 (C$_5$H$_5$), 126.0 (C$_5$H$_5$). $^{29}$Si NMR {$^1$H}, (CD$_2$Cl$_2$): δ$_{Si}$ −3.99 (SiCp), 5.11 (Si(CH$_3$)$_2$), 6.0–8.0 (SiCH$_3$, CH$_2$Si).

Example 38

The following example is provided to demonstrate the polymerization of ethylene using the zirconocene complex prepared in Synthesis 37C of the foregoing Example 37.

A 250 mL three-necked flask equipped with reflux condenser, magnetic stir bar, inside thermometer and a gas inlet tube was filled with 100 mL of toluene, 0.66 mL MAO solution (10% in toluene) and 0.5 mL of a 2×10$^{-3}$ M solution of [—MeSi(CH$_2$CH$_2$—)(CH$_2$CH$_2$SiMe$_2$CH$_2$CH$_2$SiMe$_2$C$_5$H$_4$](C$_5$H$_5$)ZrCl$_2$]$_n$ (n approximately 6) as described in Synthesis 10C in toluene. This solution was stirred for 20 minutes to activate the catalyst. The catalyst solution was then heated to 45° C. and held at this temperature. Ethylene was bubbled through the system for 15 minutes. The reaction was stopped by addition of 50 mL of a methanol solution containing 0.5 mL of 1 M HCl. The polymer was then filtered and washed several times with 120 mL of methanol. Finally, the polymer was dried in vacuum at 40° C. for 20 hours. A yield of 1.43 g polyethylene which corresponds to a catalyst activity of 5736 kg/mol×hour (956 kg/mol(Zr)×hour) was obtained.

Example 39

The following example describes preparation of a dendrimer starting with a Si(CH=CH$_2$)$_4$ core and subsequent chemical conversions of the dendrimer.

Synthesis 39A—Preparation of the Dendrimer

Into a 10 mL flask equipped with a stir bar and rubber septum was added 209 mg (1.53 mmol) of Si(CH=CH$_2$)$_4$, 2 mL of THF and approximately 1/10 of 775 mg (6.14 mmol) of (CH$_2$CH=CH$_2$)$_2$MeSiH. This mixture was stirred at room temperature. Then, 1 drop of the Karstedt catalyst was added. Over a period of 1 hour, the remainder of the (CH$_2$CH=CH$_2$)$_2$MeSiH was added slowly by syringe at room temperature. Then, the mixture was stirred at 50° C. for 4 hours. All volatiles were removed at reduced pressure at 50° C. A light yellow oil ("Product 39A") remained. A yield of 0.98 g, approximately 100%, was obtained. Anal. Calcd. for $(C_{36}H_{68}Si_5)_n$: C, 67.42; H 10.68. Found: C, 67.29; H, 10.74. $^1$H NMR (C$_6$D$_6$): δ 0.00–0.25 (s (overlapped), 3H, SiC$\underline{H}_3$), 0.50–0.85 (m, 4H, SiC$\underline{H}_2$C$\underline{H}_2$Si), 1.02–1.20 (m, approx. 1H, 20 CH$_2$C$\underline{H}_2$CH$_2$ (byproduct of addition to allyl)), 1.58 (m, 4H, SiC$\underline{H}_2$CH=CH$_2$), 4.83–5.04 (m, 4.8H, CH$_2$CH=C$\underline{H}_2$), 5.70–5.95 (m, approx. 1H, CH$_2$C$\underline{H}$=CH$_2$), 5.95–6.25 (m, approx. 1H, SiCH=CH$_2$). Molecular Weight (VPO in toluene): M=546 g/mol.

Conversion 39B—Addition of Me$_2$SiHCl to Product 39A Dendrimer

Into a 25 mL flask equipped with a stir bar and rubber septum was added 807 mg (1.26 mmol) of "Si[CH$_2$CH$_2$SiMe(CH$_2$CH=CH$_2$)$_2$]$_4$" as already described in Synthesis 39A and 0.5 mL of ether. Then, 2.0 mL, (18.3 mmol) of Me$_2$SiHCl was added slowly. The reaction started spontaneously and the temperature increased. The mixture was stirred at 35° C. for 6 hours. The volatiles were removed at reduced pressure at 50° C. A colorless, viscous oil ("Product 12B") remained. A yield of 1.75 g, approximately 100%, was obtained. $^1$H NMR (CDCl$_3$): δ −0.10–0.15 (s(overlapped), 3H. SiC$\underline{H}_3$), 0.38 (s, 12H, SiC$\underline{H}_3$Cl), 0.50–0.72 (m, 4H, SiC$\underline{H}_2$CH$_2$CH$_2$SiCl), 0.80–1.00 (m, 4H, SiCH$_2$C$\underline{H}_2$CH$_2$SiCl), 1.30–1.50 (m, 4H, SiCH$_2$CH$_2$C$\underline{H}_2$SiCl).

Conversion 39C—Reduction of Product 39B With LiAlH$_4$

Into a 25 mL flask equipped with a stir bar and rubber septum was added 1.70 g (1.22 mmol) of Si[CH$_2$CH$_2$SiMe(CH$_2$CH$_2$CH$_2$SiMe$_2$Cl)$_2$]$_4$" as already described in Conversion 39B and 3 mL of ether. Then, 300 mg (7.90 mmol) of LiAlH$_4$ in 10 mL of ether was added slowly by syringe. A reaction started as the temperature was increased. The mixture was stirred at 35° C. for 4 hours. Then, the reaction mixture was hydrolyzed with 10 mL of 0.5 M HCl. The solution was filtered through Celite™ (Celite 545™), a diatomaceous earth purchased from Fisher Scientific Co., and washed twice with 3 mL of ether. The organic layer was washed with water and separated. After the solution was dried over MgSO$_4$, all volatiles were removed at reduced pressure at 50° C. A colorless, viscous oil ("Product 39C") remained. A yield of 1.15 g, 82%, was obtained. Anal. 4 Calcd. for $C_{52}H_{132}Si_{13}$:C, 55.63; H, 11.85. Found: C, 55.87; H, 11.88. $^1$H NMR (C$_6$D$_6$): δ 0.00–0.38 (s (overlapped), 15H, SiC$\underline{H}_3$), 0.55–1.00 (m, 10H, SiC$\underline{H}_2$), 1.15–1.40 (m, approx. 2H, C$\underline{H}_2$(byproduct)), 1.50–1.90 (SiCH$_2$C$\underline{H}_2$CH$_2$Si), 4.12–4.30 (m, 1H, Si$\underline{H}$). Molecular Weight (VPO in toluene): M=1024 g/mol.

Synthesis 39D—Preparation of a Dichlorozirconocene complex [—MeSi(CH$_2$H$_2$—)(CH$_2$CH$_2$SiMe$_2$CH$_2$CH$_2$SiMe$_2$C$_5$H$_4$] C$_5$H$_5$)ZrCl$_2$]$_n$ (n approximately 6)

Into a 20 mL flask equipped with a stir bar and rubber septum were added 470 mg (1.25 mmol) of (CH$_2$=CH)Me$_2$Si(C$_5$H$_4$)C$_5$H,ZrCl$_2$, 175 mg (0.16 mmol) of "Si[CH$_2$CH$_2$SiMe(CH$_2$CH$_2$CH$_2$SiMe$_2$H)$_2$]$_4$" described already in Conversion 39C, 0.5 mL of THF and 2 drops of the Karstedt catalyst solution. This mixture was stirred at 50° C. for 6 hours. Then, all volatiles were removed at reduced pressure, and the residue was washed twice with 1 mL of hexane. The light brown, waxy product ("Product 39D") was dried in vacuum at 40° C. A yield of 640 mg, 99%, was obtained. Anal. Calcd. for $C_{164}H_{276}Cl_8Si_{21}Zr_8$: C, 51.15; H, 7.22. Found: C, 49.32; H, 7.03. $^1$H NMR (CDCl$_3$) δ −0.09 (s, 12H, Si$^3$ C$\underline{H}_3$), 0.01 (s, 3H, Si$^2$C$\underline{H}_3$), 0.27 (s(overlapped), 12H, Si$^4$C$\underline{H}_3$), 0.25–0.70 (m, 20H, Si C $\underline{H}_2$), 1.25 (m, 4H, CH$_2$C$\underline{H}_2$CH$_2$), 6.44 (s, 10H, C$_5$H$_5$), 6.53 (m, 4H, C$_5$H$_4$), 6.68 (m, 4H, C$_5$H$_4$). C NMR {$^1$H}, (CDCl$_3$): δ −5.70 (Si$^2$CH$_3$), −3.89 (Si$^3$CH$_3$), 2.96 (Si$_4$CH$_3$), 3.5–10.5 (SiCH$_2$), 18.3 (SiCH$_2$C$\underline{H}_2$CH$_2$Si), 115.71 (C$_5$H$_5$), 117.01 (C$_5$H$_4$), 125.08 (C$_5$H$_4$), 125.60 (C$_5$H$_4$).

For the NMR analysis, Si atoms are numbered from the core outward toward the periphery of the dendrimer and that number indicated by a superscript to the right of the Si chemical symbol.

In the foregoing Example 39, the various "Si[ ]$_4$" species are written within quotation marks because their molecular structure is not this regular. By NMR indications, some (CH$_2$CH=CH$_2$)$_2$MeSiH addition occurred to allyl instead of to vinyl groups.

Example 40

The following example is provided to demonstrate the polymerization of ethylene using the zirconocene complex prepared in Synthesis 39D of the foregoing Example 39.

A 250 mL three-necked flask equipped with reflux condenser, magnetic stir bar, inside thermometer and a gas inlet tube was charged with 100 mL of toluene, 0.66 mL MAO solution (10% in toluene) and 0.5 mL of a 0.002 M solution of "Si[CH$_2$CH$_2$CH$_2$SiMe$_2$CH$_2$CH$_2$SiMe$_2$(C$_5$H$_4$) C$_5$H$_5$ZrCl$_2$)$_2$]$_4$" above Example 39 in toluene. This solution was stirred for 20 minutes to activate the catalyst. The catalyst solution was then heated to 45° C. and held at this temperature. Ethylene was bubbled through the system for 15 minutes. The temperature increased to 60° C. spontaneously during the reaction. The reaction was stopped by addition of 50 mL of a methanol solution containing 0.5 mL of 1 M HCl. The polymer was then filtered and washed several times with 200 mL of methanol. Finally, the polymer was dried in vacuum at 40° C. for 20 hours. A yield of 3.10 g polyethylene which corresponds to a catalyst activity of 12400 kg/mol hour (1550 kg/mol(Zr)×hour) was obtained.

In the foregoing Example 40, the various "Si[ ]$_4$" species are written within quotation marks because their molecular structure is not this regular. By NMR indications, some (CH$_2$CH=CH$_2$)$_2$MeSiH addition occurred to allyl instead of to vinyl groups.

Example 41

The following example describes growth of a larger dendrimer than those described in the foregoing examples starting here from a tetrafunctional core.

Into a 25 mL flask equipped with a stir bar and rubber septum was added 1.0 g (1.56 mmol) of Si[CH$_2$CH$_2$SiMe (CH$_2$CH=CH$_2$)$_2$]$_4$, prepared as described in Example 39, 1.0 mL of ether and 1 drop of the Karstedt catalyst. Over a period of 8 hours, 1.575 g (12.47 mmol) of (CH$_2$CH=CH$_2$)$_2$ MeSiH was added slowly by syringe at 40° C. Then, the mixture was stirred at 45° C. for 24 hours. The ether was removed at reduced pressure at 45° C. A light yellow, viscous oil remained. A yield of 2.57 g, approximately 100%, was obtained. $^1$H NMR (C$_6$D$_6$): δ −0.05–0.40 (m, 36H, SiCH3), 0.50–1.30 (m, 48H, SiC$\underline{H}_2$CH$_2$CH$_2$Si, SiC $\underline{H}_2$C$\underline{H}_2$Si), 1.35–1.90 (m, 48 H, SiCH$_2$C$\underline{H}_2$CH$_2$Si,SiC $\underline{H}_2$CH=CH$_2$), 4.95–5.15 (m, 32H, CH$_2$CH=C$\underline{H}_2$), 5.65–6.20 (m, 16H, CH$_2$C$\underline{H}$=CH$_2$). Molecular Weight (by GPC): M$_n$=1611 g/mol, M$_W$=2113 g/mol, M$_w$/M$_n$=1.31 where M$_n$, represents the number average molecular weight and M$_W$ represents the weight average molecular weight.

What is claimed is:

1. An organosilicon dendrimer comprising a dendrimer arm including a metal-containing unit, wherein a metal in the metal-containing unit is a Group 4 metal selected from the group consisting of Ti, Zr, and Hf.

2. The dendrimer of claim 1 wherein said organosilicon is selected from the group consisting of carbosilane, siloxane and hybrids thereof.

3. The dendrimer of claim 1 wherein said dendrimer is further characterized by a dendrimer arm end and said metal-containing unit is located at said dendrimer arm end.

4. The dendrimer of claim 1 wherein said dendrimer is further characterized by a dendrimer core and said dendrimer arm is further characterized by a dendrimer arm end and a dendrimer arm interior intermediate between said dendrimer core and said dendrimer end and wherein said metal-containing unit is located at said dendrimer arm interior.

5. The dendrimer of claim 1 wherein said metal-containing unit is a metallocene unit.

6. The dendrimer of claim 5 wherein said metallocene unit is a bis(cyclopentadienyl) complex further characterized by the formula

wherein Z is selected from the group consisting of chalcogen, halide, alkyl, aryl, and amide substituents, M is said Group 4 metal and

▶ denotes a bond connecting said metallocene unit to said dendrimer arm.

7. The dendrimer of claim 6 wherein said chalcogen substituent is selected from the group consisting of O$_2$CR, OR, O$_3$SCF$_3$ and SR wherein R is an organic substituent selected from the group consisting of alkyl, polyfluoroalkyl, and aryl.

8. The dendrimer of claim 6 wherein said halide is selected from the group consisting of F, Cl, Br and I.

9. The dendrimer of claim 5 wherein said metallocene unit is characterized by the formula

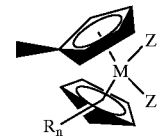

further including an R substituent wherein n is the number of said R substituents and n is an integer in the range of from about 1 to about 5 and R is selected from the group consisting of alkyl and aryl groups and Z is selected from the group consisting of chalcogen, halide, alkyl, aryl and amide substituents.

10. The dendrimer of claim 9 wherein said alkyl group is a methyl group.

11. The dendrimer of claim 9 wherein said aryl group is selected from the group consisting of phenyl and benzyl groups.

12. The dendrimer of claim 5 wherein said metallocene unit is characterized by the formula

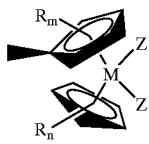

and further includes an R substituent wherein m is the number of said R substituents and m is an integer in the range of from about 1 to about 4, n is the number of said R substituents and n is an integer in the range of from about 1 to about 5 and R is selected from the group consisting of alkyl and aryl groups, and Z is selected from the group consisting of chalcogen, halide, alkyl, aryl and amide substituents.

13. The dendrimer of claim 12 wherein said alkyl group is a methyl group.

14. The dendrimer of claim 12 wherein said aryl group is selected from the group consisting of phenyl and benzyl groups.

15. The dendrimer of claim 5 wherein said metallocene unit further includes a bridging group represented by

and is characterized by the formula

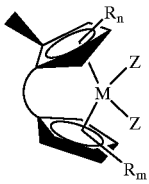

wherein R is selected from the group consisting of alkyl and aryl, m is the number of said R substituents and m is an integer in the range of from about 0 to about 3, n is the number of said R substituents and n is an integer in the range of from about 0 to about 4, and Z is selected from the group consisting of chalcogen, halide, alkyl, aryl and amide substituents.

16. The dendrimer of claim 15 wherein said bridging group is an organic bridging group selected from the group consisting of $CH_2$, $CH_2CH_2$, $CMe_2$, $CH_2CH_2CH_2$, $Me_2CCMe_2$, and $CH=CH$.

17. The dendrimer of claim 15 wherein said bridging group is an organosilicon bridge selected from the group consisting of $SiMe_2$, $SiMe_2CH_2SiMe_2$, $SiMe_2CH_2CH_2SiMe_2$, $Me_2SiSiMe_2$ and $Me_2SiOSiMe_2$.

18. The dendrimer of claim 5 wherein said metallocene unit further includes a functional group represented by

and is characterized by the formula

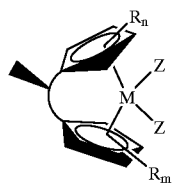

and wherein

is selected from the group consisting of $MeSiCH_2SiMe_2$, $MeSi$, $PhSi$, $MeSiSiMe_2$, $MeSiOSiMe_2$ and $MeSiCH_2CH_2SiMe_2$ groups, R is selected from the group consisting of alkyl and aryl, m is the number of said R substituents and m is an integer in the range of from about 0 to about 4, n is the number of said R substituents and n is an integer in the range of from about 0 to about 4, and Z is selected from the group consisting of chalcogen, halide, alkyl, aryl and amide substituents.

19. The dendrimer of claim 5 wherein said metallocene unit is characterized by the formula

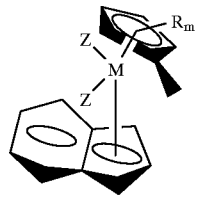

where R is selected from the group consisting of alkyl and aryl, m is the number of said R substituents and m is an integer in the range of from about 0 to about 4.

20. The dendrimer of claim 5 wherein said metallocene unit is a monocyclopentadienyl unit characterized by the formula

wherein Z is selected from the group consisting of chalcogen, halide, alkyl, aryl, and amide substituents, M is said Group 4 metal and

denotes a bond connecting said metallocene unit to said dendrimer arm and R is a group selected from the group consisting of methyl, alkyl, and aryl, and n is an integer in the range of from about 0 to about 4.

21. The dendrimer of claim 5 wherein said metallocene unit is characterized by the formula

wherein Z is selected from the group consisting of chalcogen, halide, alkyl, aryl, and amide substituents, M is said Group 4 metal and

denotes a bond connecting said metallocene unit to said dendrimer arm.

22. The dendrimer of claim 5 wherein said metallocene unit is characterized by the formula

wherein Z is selected from the group consisting of chalcogen, halide, alkyl, aryl, and amide substituents, M is said Group 4 metal,

denotes a bond connecting said metallocene unit to said dendrimer arm, and

represents a group selected from the group consisting of

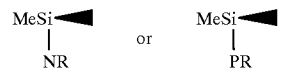

groups, R is selected from the group consisting of methyl, isopropyl, t-butyl, alkyl, phenyl, and aryl, and n is an integer in the range of from about 0 to about 3.

23. The dendrimer of claim 5 wherein said metallocene unit is further characterized by the formula

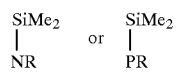

wherein Z is selected from the group consisting of chalcogen, halide, alkyl, aryl, and amide substituents, M is said Group 4 metal,

notes a bond connecting said metallocene unit to said dendrimer arm,

represents a group selected from the group consisting of $$\begin{array}{cc} \text{MeSi}\blacktriangleleft & \text{MeSi}\blacktriangleleft \\ | & \text{or} & | \\ \text{NR} & \text{PR} \end{array}$$

groups, R is selected from the group consisting of methyl, isopropyl, t-butyl, alkyl, and aryl, and is an integer in the range of from about 0 to about 3.

24. The dendrimer of claim 5 wherein said metallocene unit is further characterized by the formula

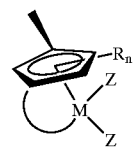

wherein Z is selected from the group consisting of chalcogen, halide, alkyl, aryl, and amide substituents, M is said Group 4 metal,

denotes a bond connecting said metallocene unit to said dendrimer arm,

represents a group selected from the group consisting of

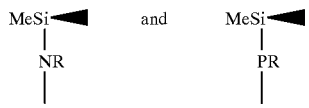

groups, and R is selected from the group consisting of methyl, isopropyl, t-butyl, alkyl, and aryl.

25. The dendrimer of claim 1 further including a solid phase support and wherein said dendrimer is chemically attached to said solid phase support.

26. The dendrimer of claim 1 wherein said dendrimer is characterized by the formula

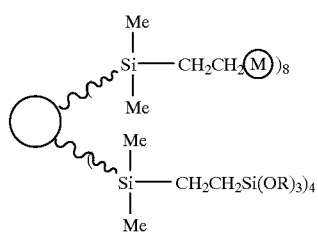

wherein ◯ represents the rest of the dendrimer, ᴡ denotes a bond connecting said dendrimer arm to said dendrimer, R is selected from the group consisting of alkyl, methyl and ethyl groups, Z is selected from the group consisting of chalcogen, halide, alkyl, aryl, and amide substituents wherein Ⓜ is a Group IV metallocene substituent, Ⓜ being formed from a metallocene reagent selected from the group consisting of

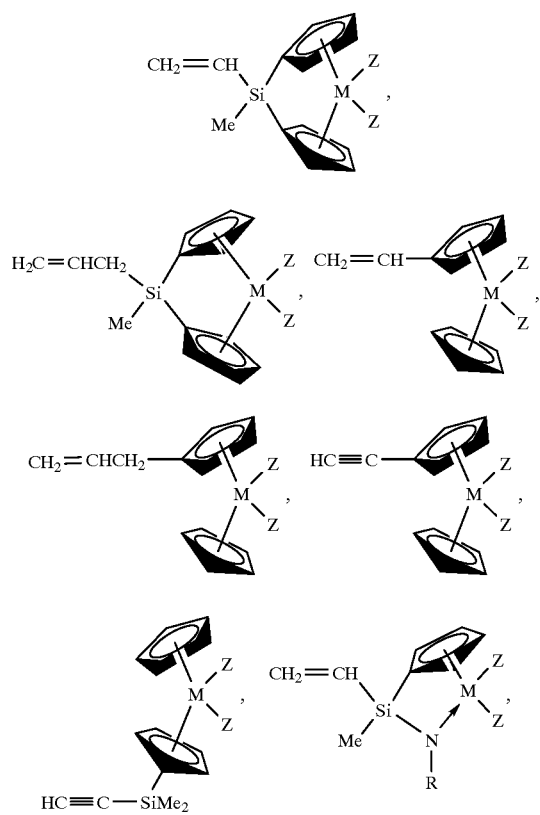

-continued

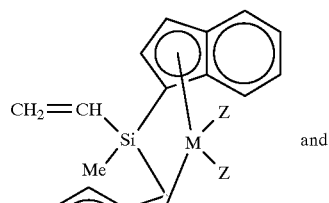

and

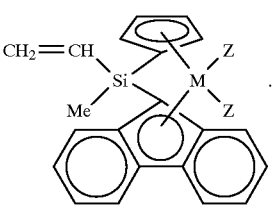

27. The dendrimer of claim 1 wherein said dendrimer includes an anchoring dendrimer arm characterized by the formula

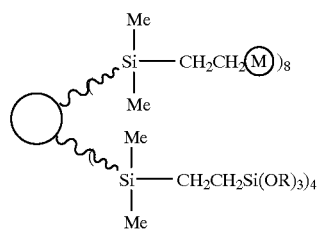

wherein ᴡ denotes a bond connecting said anchoring dendrimer arm to said dendrimer, wherein R is selected from the group consisting of alkyl, methyl, and ethyl.

28. The dendrimer of claim 25 wherein said solid phase support is selected from the group consisting of refractory oxides and insoluble polymers.

29. A method for synthesizing an organosilicon dendrimer comprising steps of:

(a) providing a core molecule further including a reactive functional group;

(b) providing a silicon hydride;

(c) providing a hydrosilylation catalyst;

(d) reacting said silicon hydride with said core molecule in the presence of said hydrosilylation catalyst to produce an intermediate organosilicon dendrimer;

(e) reacting said intermediate organosilicon dendrimer to introduce an unsaturated organic functional group;

(f) repeating steps (b), (c), (d), and (e) n times using said intermediate organosilicon dendrimer as formed in step (e) as said core molecule to produce a $G_n$ generation organosilicon dendrimer wherein n is an integer in the range of from about 1 to about 10 and $G_n$ is the generation number; and (g) reacting said $G_n$ generation organosilicon dendrimer with a Group 4 metal-containing reagent to form an organosilicon dendrimer including a Group 4 metal.

30. The method of claim 29 wherein said $G_n$ generation organosilicon dendrimer further includes a dendrimer arm end and wherein said dendrimer arm end terminates in a Si—H functional group.

31. The method of claim 30 whrein said Si—H functional group is selected from the group consisting of —SiMe$_2$H, —SiMeClH, —SiCl$_2$H, —SiMeH$_2$, —SiR$_2$H, —SiRH$_2$, and —SiRClH where R is selected from the group consisting of alkyl and aryl.

32. The method of claim 30 wherein said step (g) of reacting said $G_n$ generation organosilicon dendrimer with said Group 4 metal-containing reagent further comprises steps of providing a Group 4 metal-containing reagent further including an unsaturated organic functional group and reacting said Si—H functional group with said unsaturated organic functional group by a catalyzed hydrosilylation reaction.

33. The method of claim 29 wherein said metal-containing reagent is selected from the group consisting of metallocene reagents characterized by the formulas

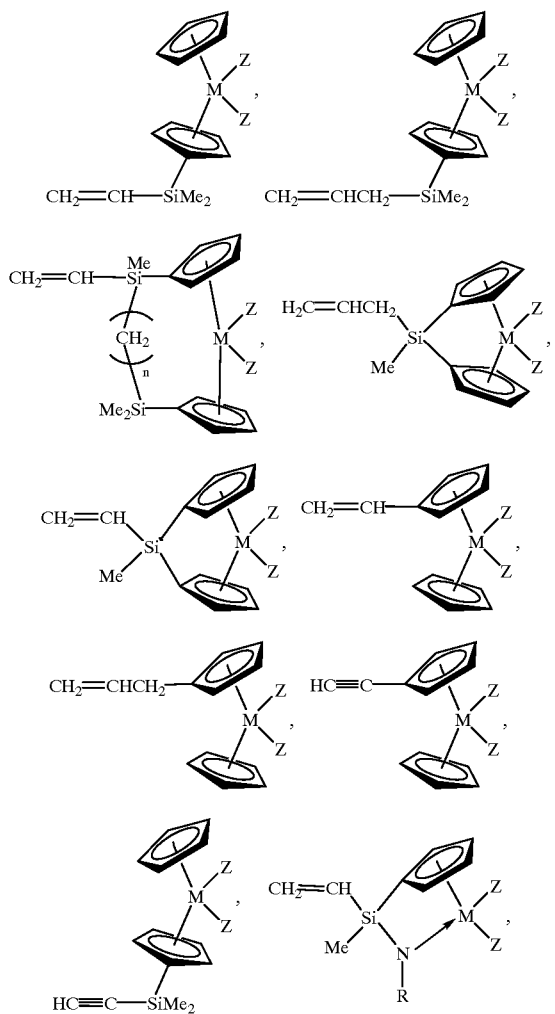

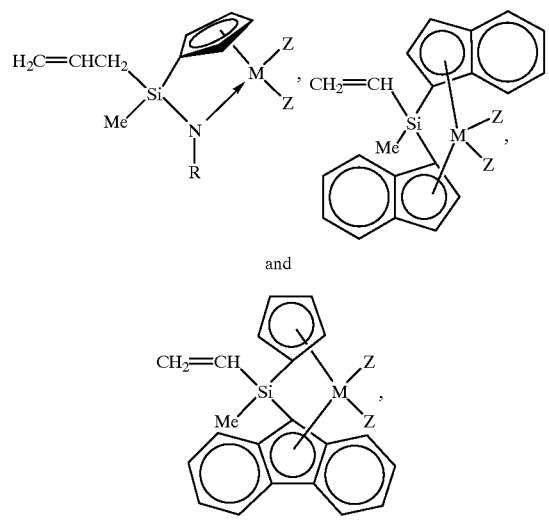

and

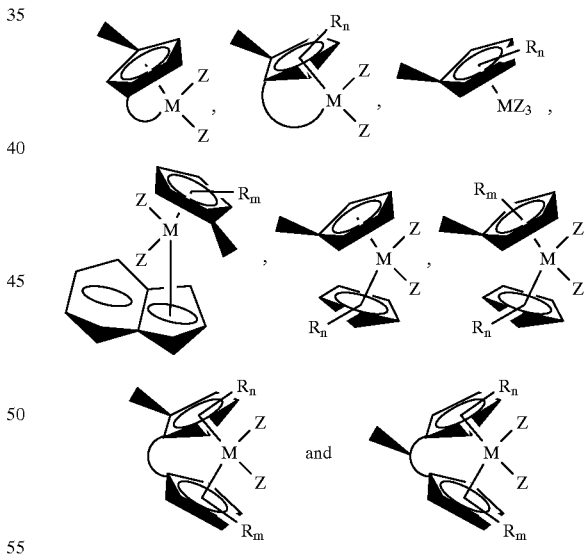

wherein Z is selected from the group consisting of chalcogen, halide, alkyl, aryl, and amide substituents, M is a Group 4 ion, R is selected from the group consisting of methyl, isopropyl, t-butyl, alkyl, and phenyl, and → represents an electron pair donor bond, wherein n is an integer defining a number of CH$_2$ groups and n equals 1–2.

34. The method of claim 29 wherein said metal-containing reagent includes a metallocene substituent selected from the group consisting of metallocene substituents characterized by the formulas R is selected from the group consisting of alkyl and aryl, m is the number of R substituents and m is an integer in the range of from about 0 to about 4, and n is the number of R substituents and n is an integer in the range of from about 0 to about 4, M is said Group 4 metal and Z is selected from the group consisting of chalcogen, halide, alkyl, aryl, and amide substituents.

35. The method of claim 29 wherein said $G_n$ generation organosilicon dendrimer further includes a dendrimer arm end and wherein said dendrimer arm end terminates in a dendrimer unsaturated organic functional group.

36. The method of claim 35 wherein said unsaturated organic functional group is selected from the group consisting of $CH_2=CH$, $CH_2=CHCH_2$, $CH_2=CH(CH_2)_n$ where n is an integer in the range of from about 2 to about 10, $HC\equiv C$, and $HC\equiv C(CH_2)_n$ where n is an integer in the range of from about 1 to about 11.

37. The method of claim 35 wherein in said step (g) of reacting said $G_n$ generation organosilicon dendrimer with said Group 4 metal-containing reagent further includes providing a reagent having a Si—H substituent and reacting said Si—H substituent with said dendrimer unsaturated organic functional group by a catalyzed hydrosilylation reaction.

38. The method of claim 37 wherein said reagent is selected from the group consisting of reagents characterized by the formulas

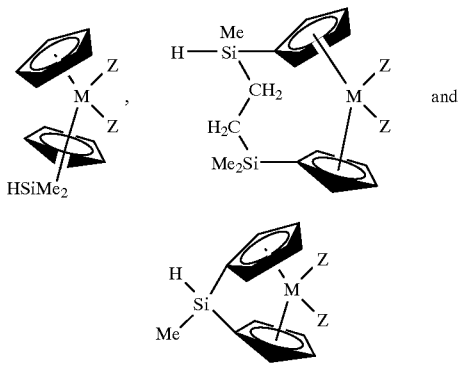

and wherein Z is selected from the group consisting of chalcogen, halide, alkyl, aryl, and amide substituents, and M is said Group 4 metal.

39. The method of claim 29 wherein said metal-containing reagent is characterized by the formula

XV

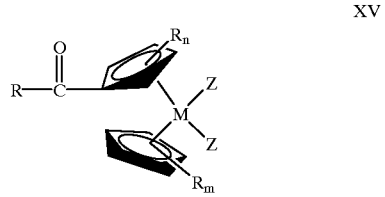

wherein Z is selected from the group consisting of chalcogen, halide, alkyl, aryl, and amide substituents, 10M is said Group 4 metal, R is selected from the group consisting of alkyl, and aryl m is an integer in the range of from about 0 to about 5, and n is an integer in the range of from about 0 to about 4.

40. The method of claim 29 wherein said intermediate organosilicon dendrimer further includes a dendrimer core, a dendrimer periphery and a dendrimer internal site intermediate between said dendrimer core and said dendrimer periphery and step (f) is performed so that a reactive functionality is introduced at said dendrimer internal site, and step (g) further includes reacting said reactive functionality with said Group 4 metal-containing reagent so that said Group 4 metal is introduced at said dendrimer internal site.

41. The method of claim 29 wherein said intermediate organosilicon dendrimer further includes a dendrimer periphery and step (f) is performed so that a reactive functionality is introduced at said dendrimer periphery, and step (g) further includes reacting said reactive functionality with said Group 4 metal-containing reagent so that said Group 4 metal is introduced at said dendrimer periphery.

42. The method of claim 29 wherein said core molecule is a polymer so that a polymeric organosilicon dendrimer is formed according to step (g).

43. A method for synthesizing a Group 4 transition metal-containing organosilicon dendrimer comprising steps of:
(a) providing starting monomers including at least one Si—H bond and at least two functional groups each further including a terminal $=CH_2$ bond;
(b) inducing a hydrosilylation reaction so that said monomers are consumed to produce an intermediate organosilicon dendrimer; and
(c) reacting said intermediate organosilicon dendrimer with a Group 4 metal-containing reagent to form an organosilicon dendrimer including a Group 4 metal.

44. The method of claim 43 wherein said starting monomers are selected from the group consisting of $HSi(CH=CH_2)_3$; $HSi(CH_2CH=CH_2)_3$; $HSi[(CH_2)_nCH=CH_2]_3$ wherein n is an integer in the range of from about 2 to about 20; $R(H)Si(CH=CH_2)_2$; $R(H)Si(CH_2CH=CH_2)_2$; and $R(H)Si[(CH_2)_nCH=CH_2]_2$, wherein n is an integer in the range of from about 2 to about 20, R is selected from the group consisting of methyl and higher alkyl, phenyl and substituted phenyl, halogen, alkoxy, aryloxy and dialkylamino groups.

45. The method of claim 43 wherein said hydrosilylation reaction is induced by exposing said monomers to a reagent selected from the group consisting of transition metal complex catalysts wherein said transition metal is selected from the group consisting of Pt, Pd, Rh, Ru, Ni, and Ti; organic peroxides; azo compounds; and supported transition metal catalysts selected from the group consisting of Pt/charcoal, Pt/asbestos, and Raney Ni.

46. The method of claim 43 wherein said hydrosilylation reaction is induced by exposing said monomers to ultraviolet radiation.

47. The method of claim 43 wherein said hydrosilylation reaction is induced by heating said monomers.

48. The method of claim 43 wherein said hydrosilylation reaction is allowed to proceed until substantially all of said starting monomers have been consumed.

49. The method of claim 43 wherein said intermediate organosilicon dendrimer further includes a dendrimer periphery and said hydrosilylation reaction is allowed to proceed until steric congestion at said dendrimer periphery hinders further growth.

50. The method of claim 43 further including, after step (b), providing additional monomers including at least one Si—H bond and at least two functional groups each further including a terminal $=CH_2$ bond and reacting said additional monomers with said intermediate organosilicon dendrimer.

51. The method of claim 50 wherein said additional monomers have the same chemical composition as said starting monomers.

52. The method of claim 50 wherein said additional monomers have a different chemical composition than said starting monomers.

53. The method of claim 52 wherein said additional monomers are characterized by the formula $H(R)Si[(CH_2)CH=CH_2]_2$ wherein R is selected from the group consisting of $(CH_2)_nCH=CH_2$, alkyl, aryl, halogen, alkoxy, aryloxy, and dialkylamino and n is an integer in the range of from about 0 to about 20.

54. The method of claim 43 wherein said intermediate organosilicon dendrimer further includes a reactive =CH$_2$ group and, after step (b), further including a step of deactivating said reactive =CH$_2$ group.

55. The method of claim 54 wherein said step of deactivating said reactive =CH$_2$ group is accomplished by addition of a silicon hydride of composition R$_2$SiH wherein R is selected from the group consisting of alkyl, aryl, halogen, alkoxy, aryloxy, siloxy, and dialkylamino and mixtures thereof.

56. The method of claim 55 wherein said silicon hydride is selected from the group consisting of Me$_2$SiHCl, MeSiHCl$_2$, HSiCl$_3$, HSi(OEt)$_3$, HSi(OMe)$_3$, HSi(NMe$_2$)$_3$, PhSiHCl$_2$ and HSiMe$_2$OSiMe$_3$.

57. The method of claim 43 wherein step (b) is carried out to produce an intermediate organosilicon dendrimer including a reactive CH=CH$_2$ group and wherein step (c) further includes steps of adding a reagent characterized by the general formula R$_2$SiHX wherein R is selected from the group consisting of Me, Et, higher alkyl, and aryl and X is selected from the group consisting of F, Cl, Br, I and alkoxy and including a Si—X bond; reducing said Si—X bond to produce a reactive Si—H bond; further reacting said reactive Si—H bond with said Group 4 metal-containing reagent to form said organosilicon dendrimer including a Group 4 metal.

58. The method of claim 43 wherein said Group 4 metal-containing reagent is selected from the group consisting of metallocene reagents characterized by the formulas

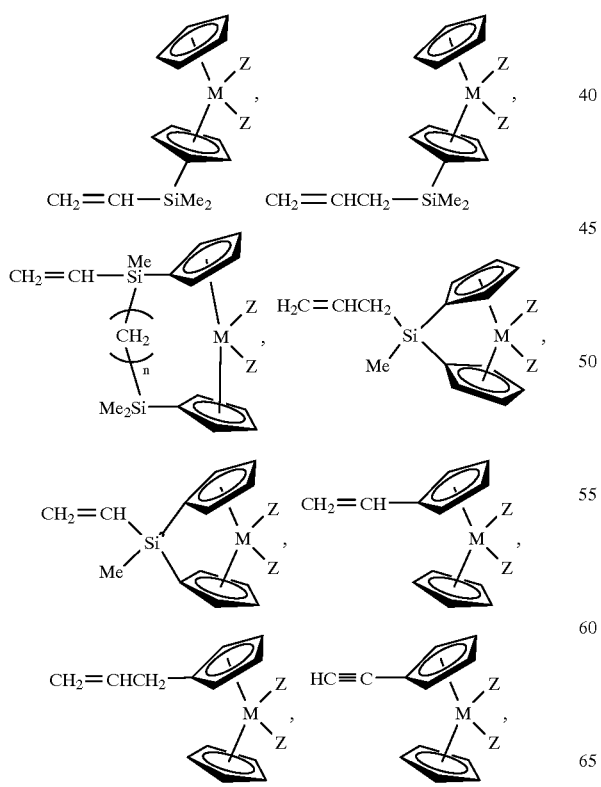

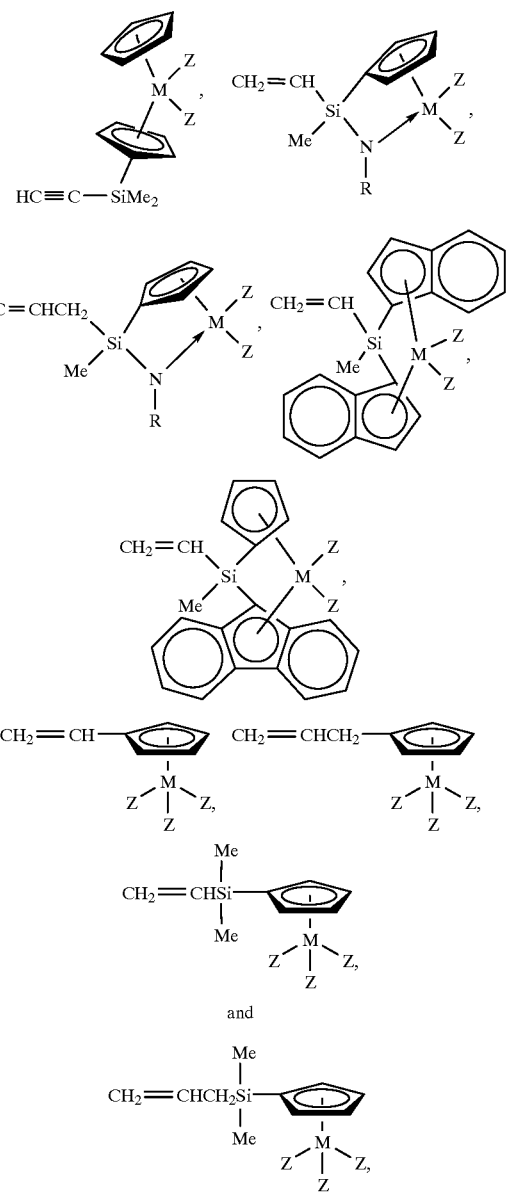

wherein Z is selected from the group consisting of chalcogen, halide, alkyl, aryl, and amide substituents, M is a Group 4 metal, R is selected from the group consisting of methyl, ethyl, isopropyl, t-butyl, alkyl, and phenyl, → represents an electron pair donor bond, and n is an integer defining a number of CH$_2$ groups and n equals 1–2.

59. The method of claim 43 wherein said Group 4 metal-containing reagent is a metallocene substituent selected from the group consisting of metallocene substituents characterized by the formulas

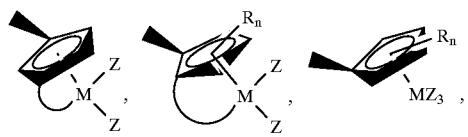

53

-continued

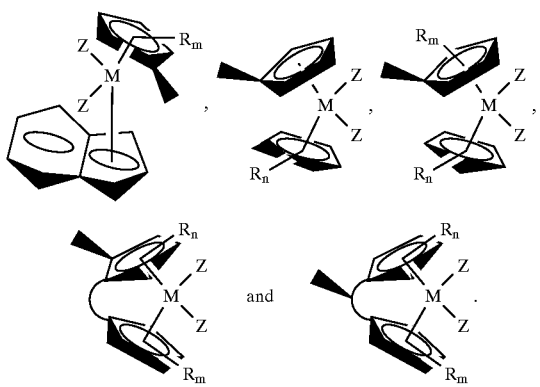

R is selected from the group consisting of alkyl and aryl, M is said Group 4 metal, Z is selected from the group consisting of chalcogen, halide, alkyl, aryl, and amide substituents, m is the number of R substituents and m is an integer in the range of from about 0 to about 4, n is the number of R substituents and n is an integer in the range of from about 0 to about 4, and

▶ denotes a bond connecting said metallocene substituent to said dendrimer.

60. The method of claim 43 wherein said intermediate organosilicon dendrimer contains a =CH$_2$ unit and said Group 4 metal-containing reagent is selected from the group consisting of reagents characterized by the formulas

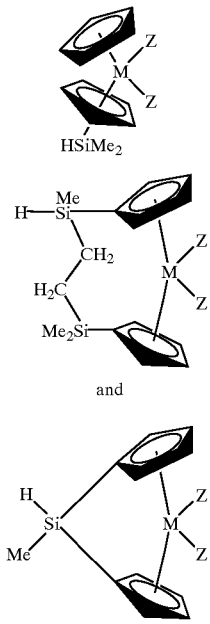

wherein Z is selected from the group consisting of chalcogen, halide, alkyl, aryl, and amide substituents, and M is said Group 4 metal.

61. The method of claim 43 wherein said Group 4 metal-containing reagent is characterized by the formula

54 wherein Z is selected from the group consisting of chalcogen, halide, alkyl, aryl, and amide substituents, M is said Group 4 metal, R is selected from the group consisting of alkyl, and aryl, m is an integer in the range of from about 0 to about 5, and n is an integer in the range of from about 0 to about 4.

62. The method of claim 43 further including a step of providing an OH-containing substrate, and wherein step (b) is carried out to produce an intermediate organosilicon dendrimer including a reactive CH=CH$_2$ group and wherein step (c) further includes steps of adding a reagent characterized by the general formula R$_2$SiHX wherein R is selected from the group consisting of Me, Et, higher alkyl, and aryl and X is selected from the group consisting of F, Cl, Br, I and alkoxy and including a Si—X bond; reducing said Si—X bond to produce a reactive Si—H bond; further reacting said reactive Si—H bond with a deficiency of said Group 4 metal-containing reagent, said Group 4 metal-containing reagent further including a substituent selected from the group consisting of vinyl, allyl and alkynyl, to produce an intermediate product; and reacting said intermediate product with a silane selected from the group consisting of vinyl silane and allyl silane and including an SiX substituent where X is further selected from the group consisting of OMe, OEt, Cl and NMe$_2$ to produce an anchorable organosilicon dendrimer including a Group 4 metal; and reacting said anchorable organosilicon dendrimer including a Group 4 metal with said OH-containing substrate so that said anchorable organosilicon dendrimer including a Group 4 metal is anchored to said OH-containing substrate.

63. A method for synthesizing a Group 4 transition metal-containing organosilicon dendrimer comprising steps of:
  (a) providing a core molecule selected from the group consisting of Si[(CH$_2$)$_n$CH=CH$_2$]$_4$ wherein n is an integer in the range of from about 0 to 20; RSi[(CH$_2$)$_n$CH=CH$_2$]$_3$ wherein n is an integer in the range of from about 0 to 20 and R is selected from the group consisting of alkyl, aryl, halogen, alkoxy and aryloxy; Si[C$_6$H$_4$(CH$_2$)$_n$CH=CH$_2$]$_3$ wherein n is an integer in the range of from about 0 to 20 and C$_6$H$_4$ is selected from the group consisting of para-phenylene and meta-phenylene; and RSi[(CH$_2$)$_n$CH=CH$_2$]$_3$ wherein n is an integer in the range of from about 0 to 20 and R is selected from the group consisting of alkyl, aryl, halogen, alkoxy and aryloxy; and C$_6$H$_4$ is selected from the group consisting of para-phenylene and meta-phenylene;
  (b) adding a first reagent selected from the group consisting of HSi(CH=CH$_2$)$_3$; HSi(CH$_2$CH=CH$_2$)$_3$; HSi[(CH$_2$)$_n$CH=CH$_2$]$_3$, wherein n is an integer in the range of from about 2 to about 20; R(H)Si(CH=CH$_2$)$_2$; R(H)Si(CH$_2$CH=CH$_2$)$_2$; and R(H)Si[(CH$_2$)$_n$CH=CH$_2$]$_2$, wherein n is an integer in the range of from about 2 to about 20, R is selected from the group consisting of methyl and higher alkyl, phenyl and substituted phenyl, halogen, alkoxy, aryloxy and dialkylamino groups to said core to form an intermediate product;

(c) adding additional reagent selected from the group consisting of $HSi(CH=CH_3)_2$; $HSi(CH_2CH=CH_2)_3$; $HSi[(CH_2)_nCH=CH_2]_3$, wherein n is an integer in the range of from about 2 to about 20; $R(H)Si(CH=CH_2)_2$; $R(H)Si(CH_2CH=CH_2)_2$; and $R(H)Si[(CH_2)_nCH=CH_2]_2$, wherein n is an integer in the range of from about 2 to about 20, R is selected from the group consisting of methyl and higher alkyl, phenyl and substituted phenyl, halogen, alkoxy, aryloxy and dialkylamino groups to said intermediate product to form an intermediate organosilicon dendrimer; and (d) reacting said intermediate organosilicon dendrimer with a Group 4 metal-containing reagent to form an organosilicon dendrimer including a Group 4 metal.

64. The method of claim 63 wherein said Group 4 metal-containing reagent is selected from the group consisting of metallocene reagents characterized by the formulas

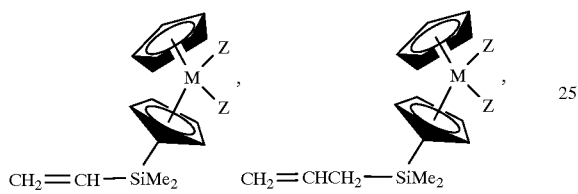
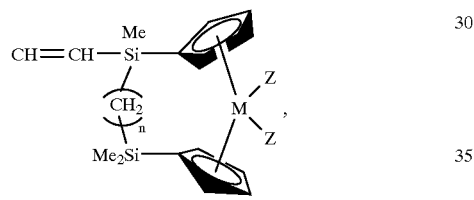
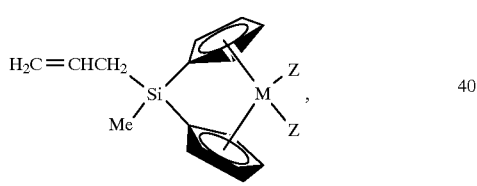
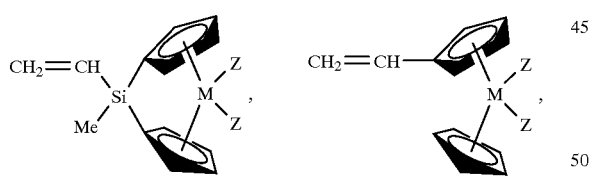
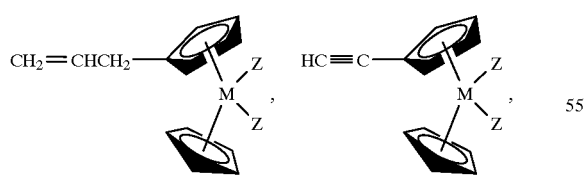
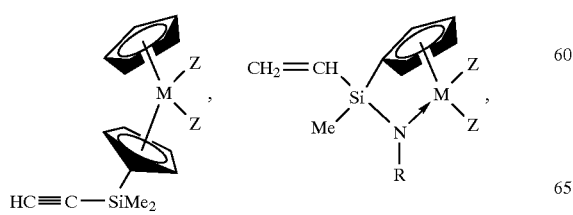

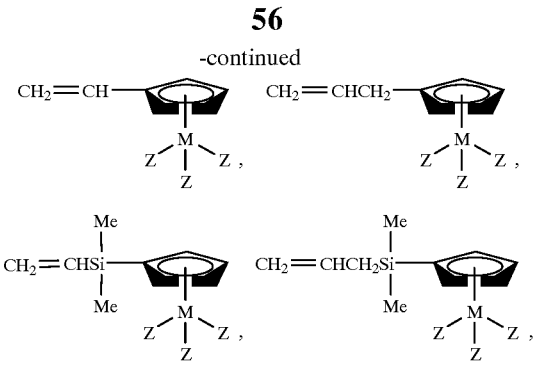
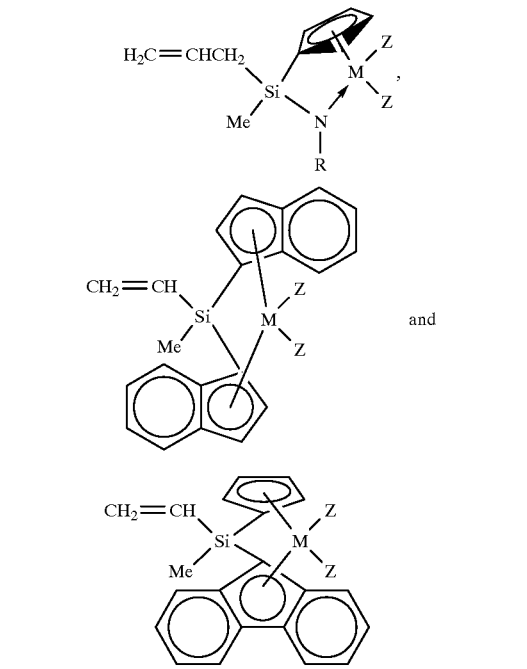

wherein Z is selected from the group consisting of chalcogen, halide, alkyl, aryl, and amide substituents, M is a Group 4 ion, R is selected from the group consisting of methyl, isopropyl, t-butyl, alkyl, and phenyl, n is an integer defining a number of $CH_2$ groups and n=1–2 and → represents an electron pair donor bond.

65. The method of claim 63 wherein said Group 4 metal-containing reagent is a metallocene substituent selected from the group consisting of metallocene substituents characterized by the formulas

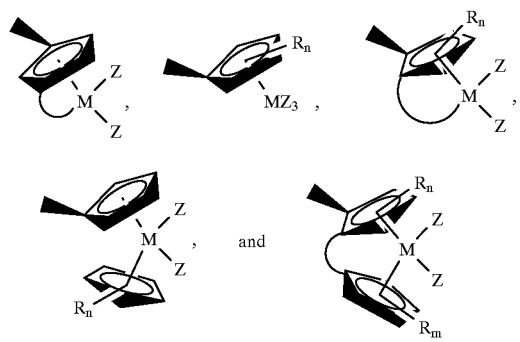

wherein R is selected from the group consisting of alkyl and aryl, m is an integer in the range of from about 0 to about 4, and is an integer in the range of from about 0 to about 4, Z is selected from the group consisting of chalcogen, halide, alkyl, aryl, and amide substituents and ▶ denotes a bond connecting said metallocene substituent to said dendrimer.

66. The method of claim 63 wherein said intermediate organosilicon dendrimer contains a =CH$_2$ unit and said Group 4 metal-containing reagent is selected from the group consisting of reagents characterized by the formulas

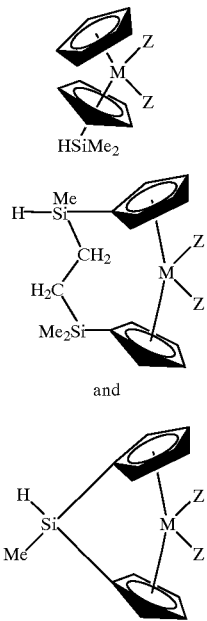

wherein Z is selected from the group consisting of chalcogen, halide, alkyl, aryl, and amide substituents, and M is said Group 4 metal.

67. The method of claim 63 wherein said Group 4 metal-containing reagent is characterized by the formula

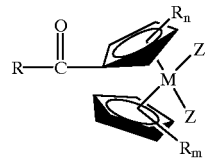

wherein Z is selected from the group consisting of chalcogen, halide, alkyl, aryl, and amide substituents, M is said Group 4 metal, R is selected from the group consisting of alkyl, and aryl m is an integer in the range of from about 0 to about 5, and n is an integer in the range of from about 0 to about 4.

68. The method of claim 63 further including, prior to step (d), a step of reacting said intermediate organosilicon dendrimer formed in step (c) with a reagent characterized by the general formula R$_2$SiHX wherein R is selected from the group consisting of Me, Et, higher alkyl, and aryl and X is selected from the group consisting of F, Cl, Br, I and alkoxy and including a Si—X bond; reducing said Si—X bond to produce a reactive Si—H bond; and further reacting said reactive Si—H bond with said Group 4 metal-containing reagent to form said organosilicon dendrimer including a Group 4 metal.

69. The method of claim 63 further including steps of
(e) providing an OH-containing substrate;

(f) reacting said intermediate organosilicon dendrimer with a reagent selected from, the group consisting of HSiX$_3$ and HSiRX$_2$, where X is selected from the group consisting of Cl, Br, I, OMe, OEt, Oalkyl, Oaryl, and NMe$_2$ and R is selected from the group consisting of Me, Ph, alkyl, and aryl to produce an anchorable dendrimer; and (g) exposing said anchorable dendrimer to said OH-containing substrate so that said anchorable dendrimer is anchored to said substrate.

70. A method for synthesizing a Group 4 transition metal-containing organosilicon dendrimer comprising steps of:

(a) providing a core molecule selected from the group consisting of Si[(CH$_2$)$_n$CH=CH$_2$]$_4$ wherein n is an integer in the range of from about 0 to 20; and RSi[(CH$_2$)$_n$CH=CH$_2$]$_3$ wherein n is an integer in the range of from about 0 to 20 and R is selected from the group consisting of alkyl, aryl, halogen, alkoxy and aryloxy;

(b) reacting said core molecule with a first reagent characterized by the formula [CH$_2$=CH(CH$_2$)$_n$]$_2$C$_6$H$_5$SiH, wherein n is an integer in the range of from about 0 to 20 to form an intermediate product;

(c) reacting said intermediate product with a second reagent selected from the group consisting of [CH$_2$=CH(CH$_2$)$_n$]$_3$SiH; and [CH$_2$=CH(CH$_2$)$_n$]$_2$SiRH, wherein R is alkyl and n is integer in the range of from about 0 to 20 to form an intermediate dendrimer including reactive dendrimer arm ends;

(d) adding a third reagent characterized by the formula R$_2$SiHX wherein X is selected from the group consisting of F, Cl, Br and I, and R is an alkyl group to react with said reactive dendrimer arm ends to form peripheral Si—X dendrimer arm ends wherein X is selected from the group consisting of F, Cl, Br, and I;

(e) reducing said peripheral Si—X dendrimer arm ends to form Si—H peripheral dendrimer arm ends;

(f) reacting said Si—H peripheral dendrimer arm ends with a reagent including a terminal olefin group to form a second intermediate dendrimer;

(g) reacting said second intermediate dendrimer with HX, wherein X is selected from the group consisting of O$_3$SCF$_3$ and Br, to form a dendrimer having a Si—X internal functionality;

(h) reacting said dendrimer having a Si—X internal functionality with a reducing agent to form a dendrimer having a Si—H internal functionality;

(i) reacting said dendrimer having a Si—H internal functionality with a Group 4 metal-containing reagent to form an organosilicon dendrimer including a Group 4 metal.

71. The method of claim 70 wherein said Group 4 metal-containing reagent is selected from the group consisting of metallocene reagents characterized by the formulas

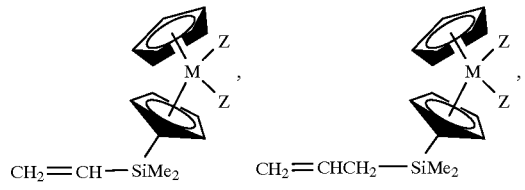

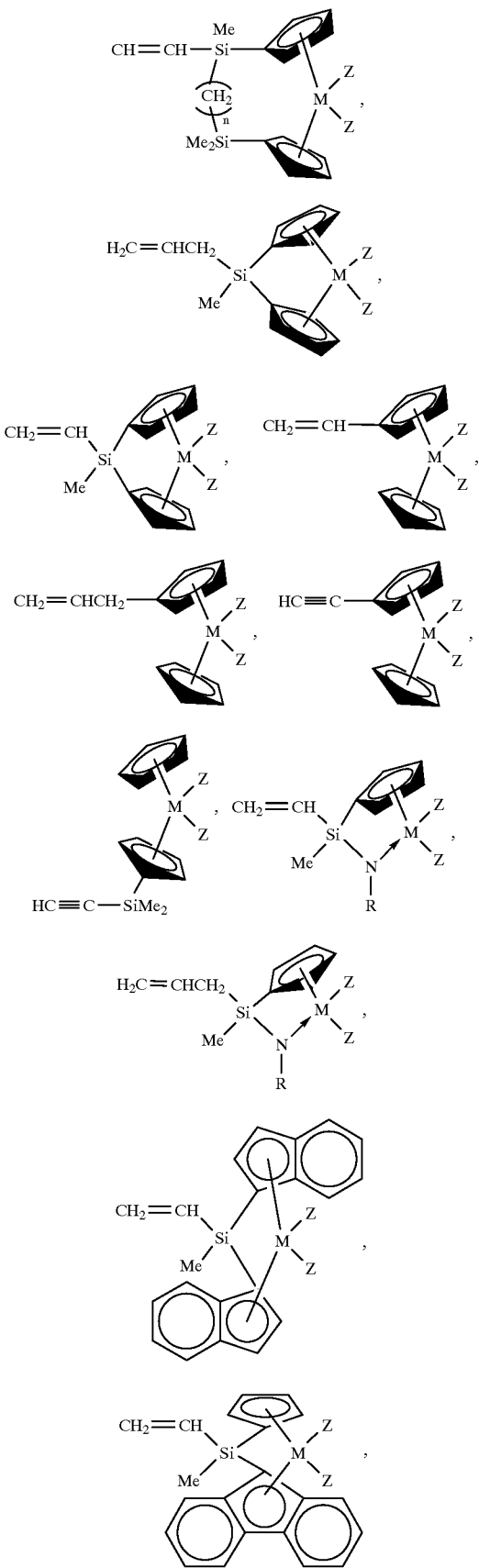

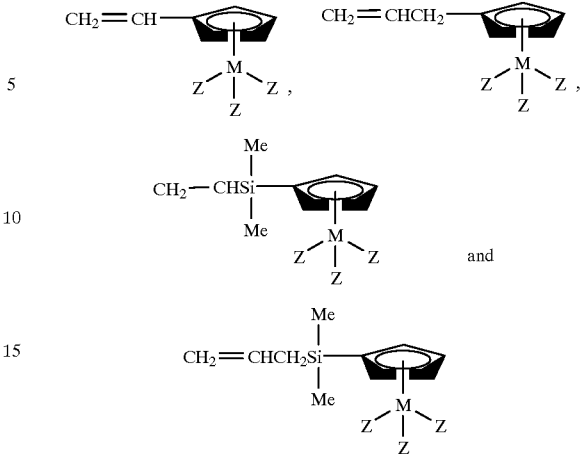

wherein Z is selected from the group consisting of chalcogen, halide, alkyl, aryl, and amide substituents, M is a Group 4 metal, R is selected from the group consisting of methyl, ethyl, isopropyl, t-butyl, alkyl, and phenyl, n is an integer defining a number of $CH_2$ groups and n=1–2 and → represents an electron pair donor bond.

72. A method for synthesizing a Group 4 transition metal-containing organosilicon dendrimer comprising steps of:

(a) providing a core molecule selected from the group consisting of $Si[(CH_2)_nCH=CH_2]_4$ wherein n is an integer in the range of from about 0 to 20; and $RSi[(CH_2)_nCH=CH_2]_3$ wherein n is an integer in the range of from about 0 to 20 and R is selected from the group consisting of alkyl, aryl, halogen, alkoxy and aryloxy;

(b) reacting said core molecule with $[CH_2=CH(CH_2)_n]R_2SiH$ wherein R is selected from the group consisting of methyl and alkyl groups to form an intermediate product and n is an integer in the range of from about 0 to about 20;

(c) reacting said intermediate product with $[CH_2=CH(CH_2)_n]_2C_6H_5SiH$ wherein n is an integer in the range of from about 0 to about 20 to form a second intermediate product;

(d) reacting said second intermediate product with a reagent selected from the group consisting of $[CH_2=CH(CH_2)n]_3SiH$ and $[CH_2=CH(CH_2)_n]_2RSiH$ wherein R is alkyl and n is an integer in the range of from about 0 to 20 to form an intermediate dendrimer including reactive dendrimer arm ends;

(e) adding a second reagent characterized by the formula $R_2SiHX$ wherein R is an alkyl group and X is selected from the group consisting of F, Cl, Br and I to react with said reactive dendrimer arm ends to form peripheral Si—X dendrimer arm ends wherein X is selected from the group consisting of F, Cl, Br, and I;

(f) reducing said peripheral Si—X dendrimer arm ends to form Si—H peripheral dendrimer arm ends;

(g) reacting said Si—H peripheral dendrimer arm ends with a reagent including a terminal olefin group to form a second intermediate dendrimer;

(h) reacting said second intermediate dendrimer with HX, wherein X is selected from the group consisting of $O_3SCF_3$ and Br, to form a dendrimer having a Si—X internal functionality;

(i) reacting said dendrimer having a Si—X internal functionality with a reducing agent to form a dendrimer having a Si—H internal functionality;

(j) reacting said dendrimer having a Si—H internal functionality with a Group 4 metal-containing reagent to form an organosilicon dendrimer including a Group 4 metal.

73. A method for synthesizing a Group 4 transition metal-containing organosilicon dendrimer comprising steps of:

(a) providing a core molecule selected from the group consisting of $Si[(CH_2)_nCH=CH_2]_4$ wherein n is an integer in the range of from about 0 to 20; and $RSi[(CH_2)_nCH=CH_2]_3$ wherein n is an integer in the range of from about 0 to 20 and R is selected from the group consisting of alkyl, aryl, halogen, alkoxy and aryloxy;

(b) reacting said core molecule with a first reagent characterized by the formula $[CH_2=CH(CH_2)_n]_2C_6H_5SiH$, wherein n is an integer in the range of from about 0 to 20 to form an intermediate product;

(c) reacting said intermediate product with a second reagent selected from the group consisting of $[CH_2=CH(CH_2)_n]_3SiH$; and $[CH_2=CH(CH_2)_n]_2SiRH$, wherein R is alkyl and n is an integer in the range of from about 0 to 20 to form an intermediate dendrimer including reactive dendrimer arm ends;

(d) adding a third reagent characterized by the formula $R_2SiHX$ where R is an alkyl group and X is selected from consisting of F, Cl, Br, and I to react with said reactive dendrimer arm ends to form peripheral Si—X dendrimer arm ends wherein X is selected from the group consisting of F, Cl, Br, and I;

(e) alkylating said peripheral Si—X dendrimer arm ends to form a second intermediate dendrimer;

(f) reacting said second intermediate dendrimer with HX, wherein X is selected from the group consisting of $O_3SCF_3$ and Br, to form a dendrimer having a Si—X internal functionality;

(g) reacting said dendrimer having a Si—X internal functionality with a reducing agent to form a dendrimer having a Si—H internal functionality;

(h) reacting said dendrimer having a Si—H internal functionality with a Group 4 metal-containing reagent to form an organosilicon dendrimer including a Group 4 metal.

74. The method of claim 73 wherein said Group 4 metal-containing reagent is selected from the group consisting of metallocene reagents characterized by the formulas

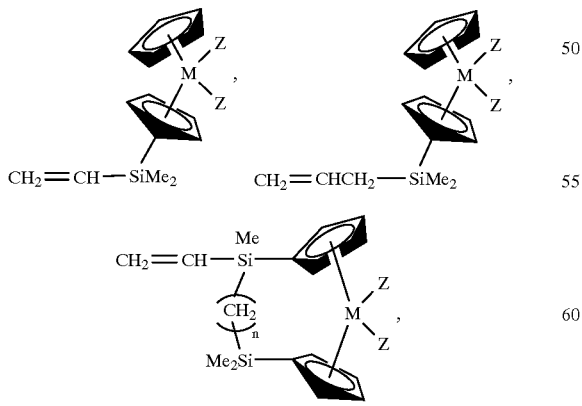

-continued

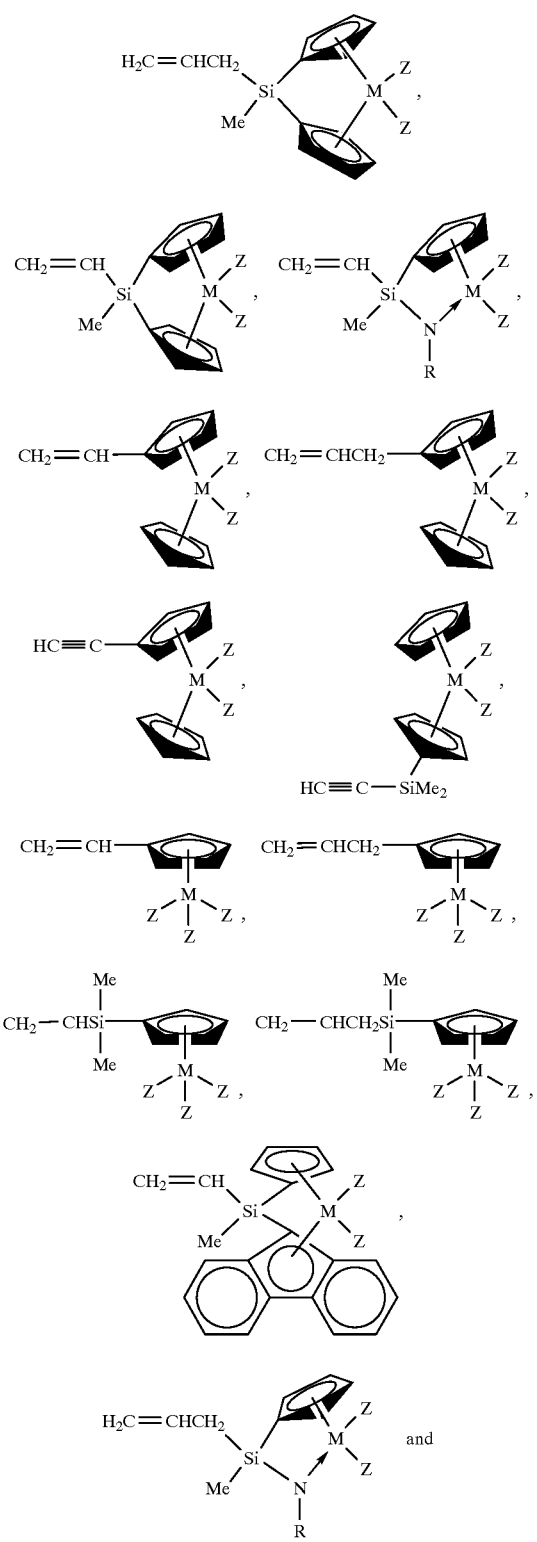

and

-continued

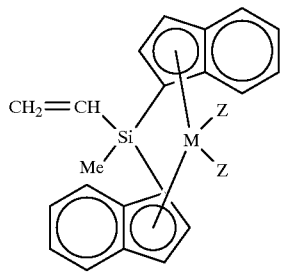

wherein Z is selected from the group consisting of chalcogen, halide, alkyl, aryl, and amide substituents, M is a Group 4 metal, R is selected from the group consisting of methyl, ethyl, isopropyl, t-butyl, alkyl, and phenyl, n is an integer defining a number of $CH_2$ groups and n=1–2 and → represents an electron pair donor bond.

75. A method for synthesizing a carbosilane dendrimer comprising steps of:
   (a) providing starting monomers including at least one Si—H bond and at least two functional groups each further including a terminal $=CH_2$ bond;
   (b) inducing a hydrosilylation reaction so that said monomers are consumed to produce an intermediate organosilicon dendrimer including a reactive $CH=CH_2$ group;
   (c) adding a reagent characterized by the general formula $R_2SiHX$ wherein R is selected from the group consisting of Me, Et, higher alkyl, and aryl and X is selected from the group consisting of F, Cl, Br, I and alkoxy; reducing said Si—X bond to produce a reactive Si—H bond; and
   (d) reacting said reactive Si—H bond with an organic compound including an unsaturated carbon-carbon bond selected from the group consisting of olefinic and acetylenic bonds to form said carbosilane dendrimer.

76. A method for synthesizing a carbosilane dendrimer comprising steps of:
   (a) providing a core molecule selected from the group consisting of $Si[(CH_2)_nCH=CH_2]_4$ wherein n is an integer in the range of from about 0 to 20; and $RSi[(CH_2)_nCH=CH_2]_3$ wherein n is an integer in the range of from about 0 to 20 and R is selected from the group consisting of alkyl, aryl, halogen, alkoxy and aryloxy; $Si[C_6H_4(CH_2)_nCH=CH_2]_4$ wherein n is an integer in the range of from about 0 to 20 and $C_6H_4$ is selected from the group consisting of para-phenylene and meta-phenylene; and $RSi[C_6H_4(CH_2)_nCH=CH_2]_3$ wherein n is an integer in the range of from about 0 to 20 and R is selected from the group consisting of alkyl, aryl, halogen, alkoxy and aryloxy; and $C_6H_4$ is selected from the group consisting of para-phenylene and meta-phenylene;
   (b) adding a first reagent selected from the group consisting of $HSi(CH=CH_2)_3$; $HSi(CH_2CH=CH_2)_3$; $HSi(CH_2)_nCH=CH_2]_3$, wherein n is an integer in the range of from about 2 to about 20; $R(H)Si(CH=CH_2)_2$; $R(H)Si(CH_2CH=CH_2)_2$; and $R(H)Si[(CH_2)_nCH=CH_2]_2$, wherein n is an integer in the range of from about 2 to about 20, R is selected from the group consisting of methyl and higher alkyl, phenyl and substituted phenyl, halogen, alkoxy, aryloxy and dialkylamino groups to said core molecule to form an intermediate product;
   (c) adding additional reagent selected from the group consisting of $HSi(CH=CH_2)_3$; $HSi(CH_2CH=CH_2)_3$; $HSi[(CH_2)_nCH=CH_2]_3$, wherein n is an integer in the range of from about 2 to about 20; $R(H)Si(CH=CH_2)_2$; $R(H)Si(CH_2CH=CH_2)_2$; and $R(H)Si[(CH_2)_nCH=CH_2]_2$, wherein n is an integer in the range of from about 2 to about 20, R is selected from the group consisting of methyl and higher Alkyl, phenyl and substituted phenyl, halogen, alkoxy, aryloxy and dialkylamino groups and $(CH_2=CHCH_2)_2(CH_3)SiH$ to said intermediate product to form an intermediate organosilicon dendrimer including a terminal $CH=CH_2$;
   (d) adding a reagent characterized by the general formula $R_2SiHX$ wherein R is selected from the group consisting of Me, Et, higher alkyl, and aryl and X is selected from the group consisting of F, Cl, Br, I and alkoxy and including a Si—X bond; reducing said Si—X bond to produce a reactive Si—H bond; and
   (e) reacting said reactive Si—H bond with an organic compound including an unsaturated carbon-carbon bond selected from the group consisting of olefinic and acetylenic bonds to form said carbosilane dendrimer.

* * * * *

UNITED STATES PATENT AND TRADEMARK OFFICE
CERTIFICATE OF CORRECTION

PATENT NO. : 5,969,073

DATED : October 19, 1999

INVENTOR(S) : Dietmar Seyferth et al.

It is certified that error appears in the above-identified patent and that said Letters Patent is hereby corrected as shown below:

On the cover page:
[22]  Filed: March 10, 1997

[63]  Continuation-in-part of application No. 08/611,495, Mar. 5, 1996, abandoned, and a continuation-in-part of application No. 08/621,290, Mar. 22, 1996, abandoned.

Column 44, line 6, please delete "notes" and insert therefor -- denotes --

Column 46, lines 25-35, please delete the structure and insert therefor
--

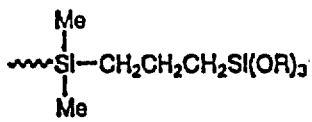

--

UNITED STATES PATENT AND TRADEMARK OFFICE
CERTIFICATE OF CORRECTION

PATENT NO. : 5,969,073
DATED : October 19, 1999
INVENTOR(S) : Dietmar Seyferth et al.

It is certified that error appears in the above-identified patent and that said Letters Patent is hereby corrected as shown below:

Column 55, line 31, please delete "CH = CH" and insert therefor
-- $CH_2 = CH$ --

Column 59, line 4, please delete "CH = CH" and insert therefor
-- $CH_2 = CH$ --

Signed and Sealed this

Fifteenth Day of August, 2000

Attest:

Q. TODD DICKINSON

*Attesting Officer*  *Director of Patents and Trademarks*